United States Patent
Wu et al.

(10) Patent No.: US 9,321,620 B2
(45) Date of Patent: Apr. 26, 2016

(54) ACTIVE STERILIZATION ZONE FOR CONTAINER FILLING

(75) Inventors: Rei-Young Amos Wu, Palatine, IL (US); Gregory Schimmel, Barrington, IL (US); Subodh K. Raniwala, Barrington, IL (US); Michael F. McGowan, Indianapolis, IN (US)

(73) Assignee: STOKELY-VAN CAMP, INC., Chicago, IL (US)

( * ) Notice: Subject to any disclaimer, the term of this patent is extended or adjusted under 35 U.S.C. 154(b) by 1377 days.

(21) Appl. No.: 12/171,052

(22) Filed: Jul. 10, 2008

(65) Prior Publication Data

US 2009/0017747 A1 Jan. 15, 2009

Related U.S. Application Data

(60) Provisional application No. 60/949,149, filed on Jul. 11, 2007.

(51) Int. Cl.
| | |
|---|---|
| B67C 7/00 | (2006.01) |
| F24F 3/16 | (2006.01) |
| B67C 3/22 | (2006.01) |
| A61L 2/08 | (2006.01) |
| B67C 3/24 | (2006.01) |
| B67C 3/26 | (2006.01) |

(52) U.S. Cl.
CPC . *B67C 3/22* (2013.01); *A61L 2/082* (2013.01); *A61L 2/087* (2013.01); *B67C 3/242* (2013.01); *B67C 7/0053* (2013.01); *B67C 7/0073* (2013.01); *A61L 2202/23* (2013.01); *B67C 2003/228* (2013.01); *B67C 2003/2688* (2013.01)

(58) Field of Classification Search
CPC .............. A61L 2/082; F24F 9/00; B67C 3/22
USPC ..................... 454/189, 188; 53/282
See application file for complete search history.

(56) References Cited

U.S. PATENT DOCUMENTS

| | | | | |
|---|---|---|---|---|
| 2,268,290 | A * | 12/1941 | Landis | 298/35 M |
| 3,081,803 | A * | 3/1963 | Frank | 141/181 |
| 3,308,739 | A * | 3/1967 | Gygax | 454/192 |

(Continued)

FOREIGN PATENT DOCUMENTS

| | | |
|---|---|---|
| DE | 29906070 | 9/1999 |
| DE | 19835369 | 10/1999 |

(Continued)

OTHER PUBLICATIONS

Office Action mailed Sep. 24, 2009, for U.S. Appl. No. 12/171,042, 17 pages.

(Continued)

*Primary Examiner* — Alissa Tompkins
*Assistant Examiner* — Phillip E Decker
(74) *Attorney, Agent, or Firm* — James R. Gourley; Brandon V. Zuniga; Carstens & Cahoon, LLP

(57) ABSTRACT

An apparatus for sterile filling of beverage containers has a first module and a second module. The first module rinses and sterilizes empty containers and delivers the sterilized containers to the second module. The second module fills and caps the containers with beverage product at ambient temperature in an active sterilization zone utilizing an e-beam sterilization unit.

13 Claims, 44 Drawing Sheets

(56) References Cited

U.S. PATENT DOCUMENTS

| | | | |
|---|---|---|---|
| 3,363,327 A * | 1/1968 | Harrison et al. | 454/188 |
| 3,473,905 A * | 10/1969 | Jago et al. | 65/27 |
| 3,486,840 A | 12/1969 | Burton | |
| 3,780,308 A | 12/1973 | Nablo | |
| 3,908,719 A | 9/1975 | Berg | |
| 4,093,066 A * | 6/1978 | Mitchell et al. | 198/860.5 |
| 4,296,068 A | 10/1981 | Hoshino | |
| 4,309,388 A | 1/1982 | Tenney | |
| 4,823,680 A * | 4/1989 | Nowotarski | 454/188 |
| 4,944,132 A | 7/1990 | Carlsson | |
| 5,009,654 A | 4/1991 | Minshall | |
| 5,053,196 A | 10/1991 | Ide et al. | |
| 5,060,449 A | 10/1991 | Klarl | |
| 5,129,239 A * | 7/1992 | Thurman | 62/507 |
| 5,493,808 A * | 2/1996 | Munday | 47/60 |
| 5,496,302 A | 3/1996 | Minshall | |
| 5,554,856 A | 9/1996 | Bidnyy | |
| 5,557,109 A | 9/1996 | Bidnyy | |
| 5,581,975 A | 12/1996 | Trebbi et al. | |
| 5,661,305 A | 8/1997 | Lawrence | |
| 5,843,374 A | 12/1998 | Sizer | |
| 5,848,514 A * | 12/1998 | Edwards et al. | 53/53 |
| 5,848,515 A | 12/1998 | Catelli et al. | |
| 5,958,336 A * | 9/1999 | Duarte | 422/24 |
| 6,026,867 A | 2/2000 | Klarl | |
| 6,082,418 A | 7/2000 | Naecker | |
| 6,140,657 A | 10/2000 | Wakalopulos | |
| 6,209,591 B1 | 4/2001 | Taggart | |
| 6,221,216 B1 | 4/2001 | Nablo | |
| 6,239,543 B1 | 5/2001 | Wakalopulos | |
| 6,413,481 B1 * | 7/2002 | Pennekamp et al. | 422/302 |
| 6,426,507 B1 | 7/2002 | Rangwalla | |
| 6,437,344 B1 | 8/2002 | Stawson | |
| 6,468,471 B1 | 10/2002 | Loda | |
| 6,481,468 B1 | 11/2002 | Taggart | |
| 6,486,482 B1 | 11/2002 | Anderberg | |
| 6,576,915 B1 | 6/2003 | McIntyre | |
| 6,610,376 B1 | 8/2003 | Rangwalla | |
| 6,617,596 B1 | 9/2003 | Korenev | |
| 6,623,706 B2 | 9/2003 | Avnery | |
| 6,668,877 B2 | 12/2003 | Fehland et al. | |
| 6,683,312 B2 * | 1/2004 | Yun | 250/455.11 |
| 6,683,319 B1 | 1/2004 | Koenck | |
| 6,690,020 B2 | 2/2004 | Loda | |
| 6,691,747 B1 | 2/2004 | Marcus et al. | |
| 6,702,984 B2 | 3/2004 | Avnery | |
| 6,713,773 B1 | 3/2004 | Lyons | |
| 6,717,154 B2 | 4/2004 | Black | |
| 6,753,535 B2 | 6/2004 | Rose | |
| 6,763,085 B2 | 7/2004 | Hansen | |
| 6,777,689 B2 | 8/2004 | Nelson | |
| 6,783,578 B2 * | 8/2004 | Tillman, Jr. | 96/224 |
| 6,806,476 B2 | 10/2004 | Rose | |
| 6,815,691 B1 | 11/2004 | Loda | |
| 6,833,551 B2 | 12/2004 | Avnery | |
| 6,868,873 B2 | 3/2005 | Frisk | |
| 6,885,011 B2 | 4/2005 | Koenck | |
| 6,885,013 B2 | 4/2005 | Loda | |
| 6,914,253 B2 | 7/2005 | Korenev | |
| 6,919,572 B2 | 7/2005 | Loda | |
| 6,940,076 B2 | 9/2005 | Olson | |
| 7,010,900 B2 | 3/2006 | Grossmann et al. | |
| 7,026,635 B2 | 4/2006 | Rangwalla | |
| 7,067,827 B2 | 6/2006 | Bol | |
| 7,096,896 B2 | 8/2006 | Py | |
| 7,145,155 B2 | 12/2006 | Nablo | |
| 7,162,848 B2 * | 1/2007 | Jacobs et al. | 53/167 |
| 7,183,563 B2 | 2/2007 | Avnery | |
| 7,187,752 B2 | 3/2007 | Kotler | |
| 7,189,978 B2 | 3/2007 | Avnery | |
| RE39,657 E | 5/2007 | Wakalopulos | |
| 7,270,158 B2 | 9/2007 | Py | |
| 7,350,759 B1 | 4/2008 | Gray | |
| 7,357,159 B2 | 4/2008 | Popplau | |
| 7,365,343 B2 | 4/2008 | Thilly | |
| 7,435,981 B2 | 10/2008 | Naka et al. | |
| 7,520,108 B2 | 4/2009 | Kristiansson et al. | |
| 7,574,845 B2 * | 8/2009 | Varhaniovsky | 53/426 |
| 7,703,262 B2 | 4/2010 | Till | |
| 7,749,434 B2 | 7/2010 | Naslund | |
| 7,832,185 B2 * | 11/2010 | Mastio et al. | 53/426 |
| 8,029,725 B2 | 10/2011 | Olsson | |
| 8,132,598 B2 * | 3/2012 | Mastio et al. | 141/51 |
| 8,156,714 B2 | 4/2012 | Munzer | |
| 8,479,782 B2 * | 7/2013 | Mastio et al. | 53/425 |
| 8,511,045 B2 * | 8/2013 | Mastio et al. | 53/167 |
| 2002/0057987 A1 | 5/2002 | Loda | |
| 2002/0092313 A1 | 7/2002 | Brifu | |
| 2003/0194344 A1 | 10/2003 | Brafford | |
| 2005/0135965 A1 | 6/2005 | Williams | |
| 2005/0158218 A1 | 7/2005 | Dumargue | |
| 2005/0173654 A1 | 8/2005 | Usami | |
| 2005/0180877 A1 | 8/2005 | Usami | |
| 2005/0188651 A1 | 9/2005 | Clusserath | |
| 2006/0037286 A1 | 2/2006 | Bernhard | |
| 2006/0159583 A1 | 7/2006 | Naslund | |
| 2006/0163499 A1 | 7/2006 | Echigo | |
| 2006/0192140 A1 | 8/2006 | Nablo | |
| 2006/0258279 A1 * | 11/2006 | Bonnard | 454/55 |
| 2006/0284111 A1 | 12/2006 | Naslund | |
| 2007/0009090 A1 | 1/2007 | Stichelbaut | |
| 2007/0018115 A1 | 1/2007 | Naka | |
| 2007/0040130 A1 | 2/2007 | Nanataki | |
| 2007/0193056 A1 * | 8/2007 | Switalski | 34/88 |
| 2007/0253861 A1 | 11/2007 | Naka | |
| 2007/0253863 A1 | 11/2007 | Iwashita | |
| 2007/0269339 A1 | 11/2007 | Frost | |
| 2007/0283667 A1 | 12/2007 | Kristiansson | |
| 2009/0013645 A1 * | 1/2009 | Mastio et al. | 53/425 |
| 2009/0013646 A1 * | 1/2009 | Mastio et al. | 53/425 |
| 2009/0013647 A1 * | 1/2009 | Mastio et al. | 53/425 |
| 2009/0013648 A1 * | 1/2009 | Mastio et al. | 53/426 |
| 2009/0017747 A1 | 1/2009 | Mastio | |
| 2009/0134338 A1 | 5/2009 | Eguchi et al. | |
| 2009/0196790 A1 | 8/2009 | Sangi | |
| 2009/0277135 A1 * | 11/2009 | Mastio et al. | 53/425 |
| 2010/0193069 A1 | 8/2010 | Ziegler et al. | |
| 2011/0023420 A1 * | 2/2011 | Mastio et al. | 53/471 |
| 2011/0072759 A1 | 3/2011 | Mielnik | |
| 2012/0124941 A1 * | 5/2012 | Mastio et al. | 53/403 |

FOREIGN PATENT DOCUMENTS

| | | | |
|---|---|---|---|
| DE | 19928325 | 12/2000 | |
| DE | 10213343 | 10/2003 | |
| DE | 10341965 | 4/2005 | |
| EP | 0405402 | 1/1991 | |
| JP | 2002114293 | 4/2002 | |
| JP | 2002179191 | 6/2002 | |
| WO | 9847770 | 10/1998 | |
| WO | 2004065283 | 8/2004 | |
| WO | WO 2005/002973 A1 * | 1/2005 | |
| WO | WO2005002973 A1 * | 1/2005 | B65B 55/08 |
| WO | 2005056465 | 6/2005 | |
| WO | 2005108278 | 11/2005 | |
| WO | 2007046213 | 4/2007 | |
| WO | 2008017410 | 2/2008 | |
| WO | 2008019828 | 2/2008 | |
| WO | 2008022740 | 2/2008 | |
| WO | 2008034512 | 3/2008 | |
| WO | 2009000850 | 12/2008 | |

OTHER PUBLICATIONS

Office Action mailed Apr. 30, 2009 for U.S. Appl. No. 12/171,040, 18 pages.

Office Action mailed Apr. 30, 2009 for U.S. Appl. No. 12/171,048, 18 pages.

Office Action mailed Nov. 25, 2009, for U.S. Appl. No. 12/171,040, 11 pages.

Office Action mailed Nov. 25, 2009, for U.S. Appl. No. 12/171,048, 8 pages.

Notice of Allowance mailed Jul. 9, 2010, for U.S. Appl. No. 12/171,042, 8 pages.

(56) References Cited

OTHER PUBLICATIONS

International Search Report for PCT/US2008/069682, dated Oct. 9, 2008.
International Search Report for PCT/US2008/069680, dated Oct. 9, 2008.
International Search Report for PCT/US2008/069678, dated Oct. 9, 2008.
International Search Report for PCT/US2008/069677, dated Oct. 9, 2008.
International Search Report for PCT/US2008/069673, dated Feb. 9, 2010.
Written Opinion for PCT/US2008/069673, dated Feb. 24, 2010.
English Abstract for JP2002179191, 1 page.
English Abstract for JP2002114293, 2 pages.
Mar. 11, 2015—(EP) Office Action—App 08 781 627.8-1707.

* cited by examiner

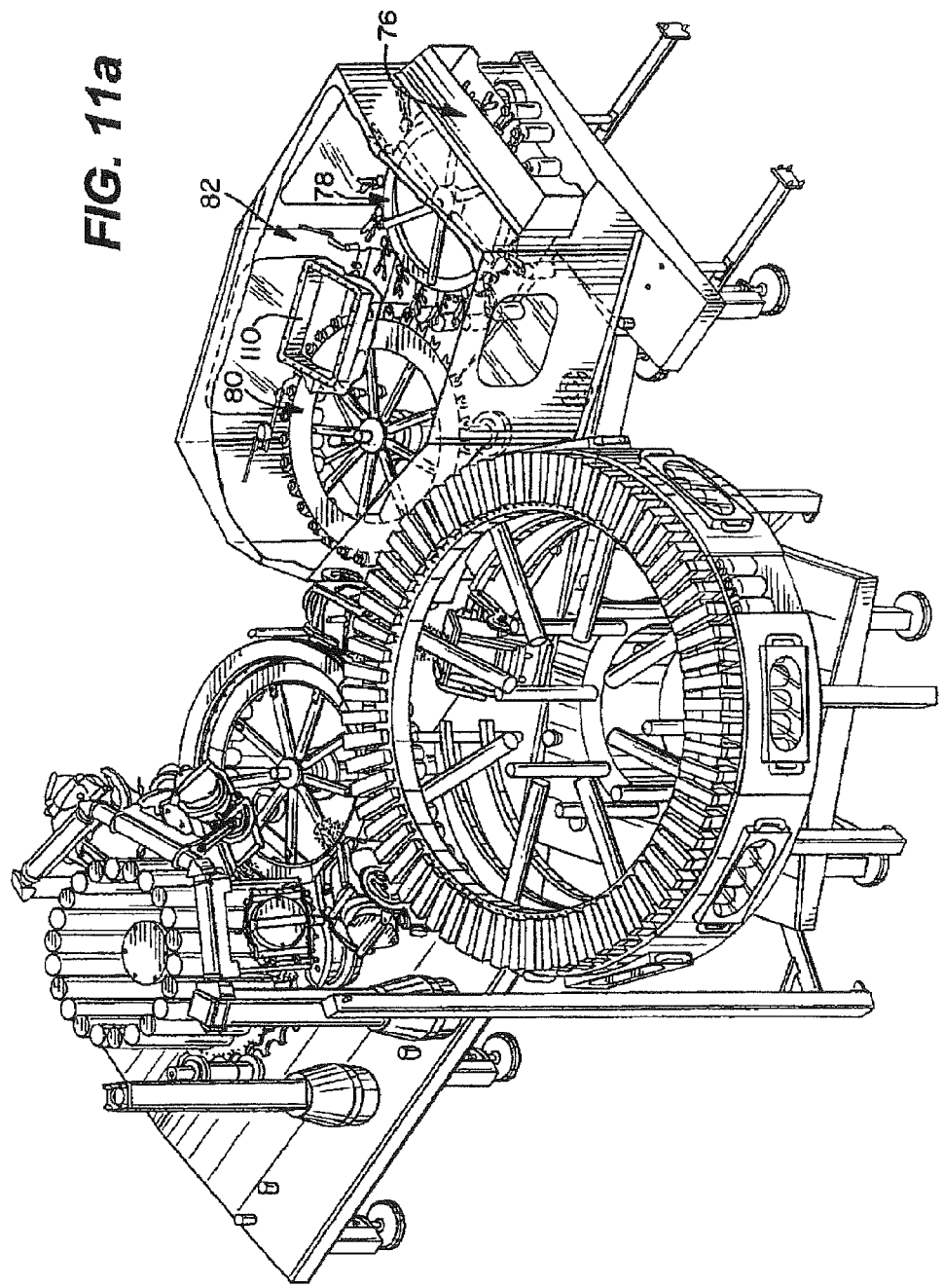

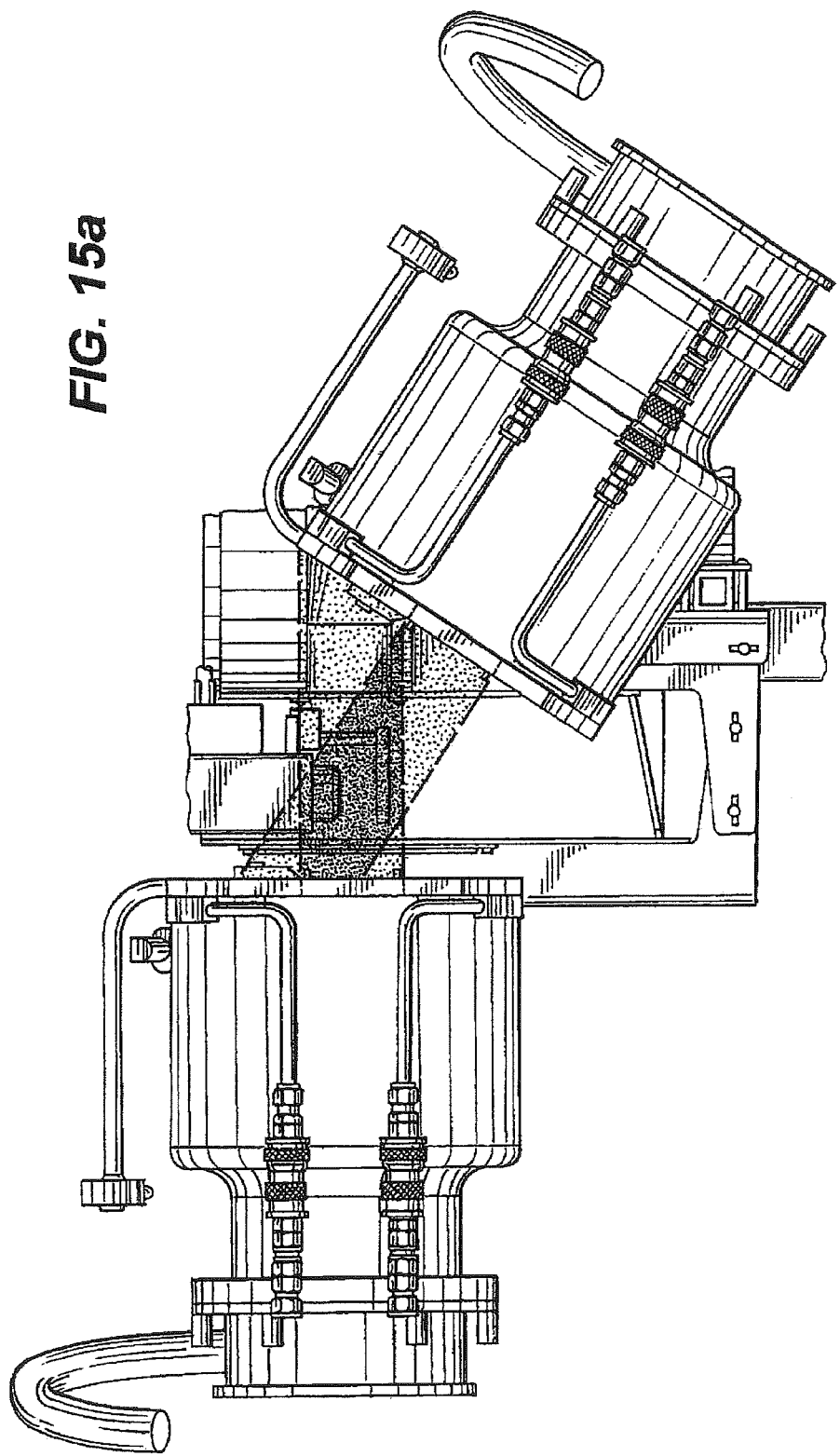

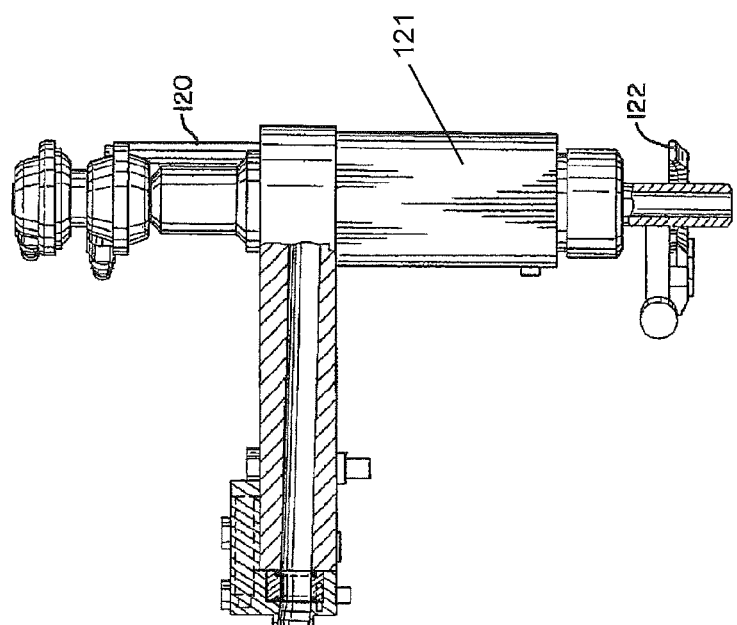
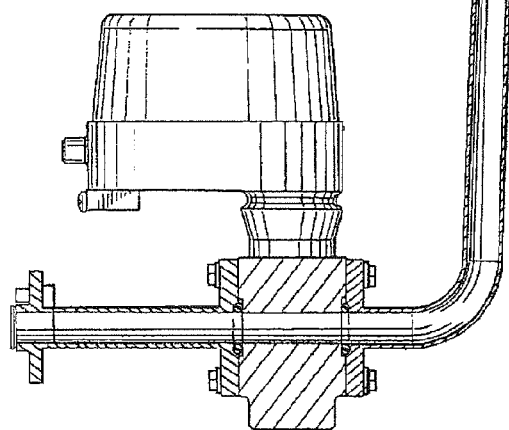
FIG. 42

ACTIVE STERILIZATION ZONE FOR CONTAINER FILLING

RELATED APPLICATIONS

This application claims priority to and the benefit of and is a continuation-in-part of U.S. Application No. 60/949,149 filed on Jul. 11, 2007 entitled "Apparatus and Method for Sterile Filling of Beverage Containers," which is incorporated herein by reference and made a part hereof.

TECHNICAL FIELD

An exemplary embodiment disclosed herein relates to sterile filling of beverage containers, and in particular, an in-line filling apparatus that creates an active sterilization zone in a confined hygienic environment ("CHE") for filling and closing containers.

BACKGROUND OF THE INVENTION

Various types of beverages or products are stored in different types of containers for eventual consumption by consumers. Beverages and other products are typically filled in containers such as thermoplastic or glass liquid containers in an automated filling process. The product, the container, and container closure, such as a cap, must all be sterilized, or free from microorganisms, to provide the consumer with a safe product that has the respective quality attributes expected by the consumer.

Typically containers can be filled with beverages in either a "cold-fill" process or a "hot-fill" process. FIG. 1 discloses a block diagram of one type of container filling and capping apparatus, typically used in a cold-fill process. FIG. 2 shows a process flow diagram of a typical aseptic cold-fill process. In cold-fill applications, the beverage product is heated to an elevated temperature for a specific time interval to kill any microorganisms (referred to as pasteurization) and is then cooled to generally ambient temperatures. Pre-sterilized containers are then filled with the cooled sterilized product in a filler 11 and the containers are capped with pre-sterilized caps by a capper 13.

In order to ensure a safe product for the consumer, the filling area in a cold-fill system must never be contaminated. Operators must wear hygienic suits, and anything that enters into the aseptic chamber must be sterilized. If there is any suspicion that a contaminant has entered the aseptic environment, the process must be shutdown, and the system must be sterilized. Cleaning a contaminated aseptic environment back to aseptic standards, however, is time consuming. All cleaning and sterilization of the associated equipment must occur during a production stoppage, therefore limiting production capability. These factors make aseptic filling lines operationally cumbersome.

In the hot-fill process, the hot beverage itself is used to sterilize the containers at the filling stage. As depicted in FIG. 3, in hot-fill applications, empty containers are initially rinsed and then filled by a filler 11 with a beverage that has been heated to an elevated temperature for sterilization. The hot beverage is not hot enough to affect the container functionality or to deform the container. In a concurrent path, caps are provided and placed on the containers immediately after filling by a capper 13. Once capped, the containers are inverted, such that the caps and the headspaces of the containers are sterilized utilizing the heated product in a cap sterilizer 15. The capped containers are then allowed to cool for further processing in a cooling tunnel 17.

In such hot-fill processes, the containers used must have a robust wall construction that can resist the high temperature of the hot beverage. The overall process requires the container to be able to withstand inversion of the container by grippers, and, therefore, requires the containers to be of a heavier weight thereby increasing material costs. In addition, as the beverage and container are cooled, a vacuum is experienced inside the capped container due to material shrinkage. Because of this vacuum, the container must have vacuum panels to absorb the shrinkage. Finally, since the beverage product must be such that the liquid remains hot for sufficient time to sterilize the container and caps, and then cooled, there is significant energy lost to the environment with the hot-fill process. These factors contribute to considerable material and operational costs of filling containers in a hot-fill process. Similar to the cold-fill process, cleaning of the hot-fill filler/capper equipment requires a stoppage of production, limiting the production capability.

An exemplary embodiment is provided to solve the problems discussed above and other problems, such as limited container design, and to provide advantages and aspects not provided by prior systems of this type. Nevertheless, the exemplary embodiments disclosed can be used to fill the containers described above. Additionally an exemplary embodiment is provided to provide more design freedom than prior systems of this type. A full discussion of the features and advantages of the disclosed exemplary embodiments is deferred to the following detailed description.

SUMMARY OF THE INVENTION

An exemplary embodiment of the invention provides a system and method for sterile filling of containers. This system provides an active sterilization zone in a CHE and includes a first module that may include a container rinser and a container sterilization unit, and a second module that may include a filler assembly and a capper assembly and further having a sterilization unit associated therewith.

According to one exemplary embodiment, the containers are directed via an in-line conveyor assembly through the first module and the second module. Once the containers are de-palletized and directed into the first module via the conveyor assembly, the containers pass through a waterless rinsing station and then are directed to a container sterilization unit having a high-powered electron beam emitter wherein the containers are initially sterilized. The containers are then conveyed to the second module having a filler assembly wherein the containers are filled with a beverage or product under aseptic conditions. The containers are then transferred to the capper assembly. A second sterilization unit is operably associated with the filler assembly and capper assembly in the second module. In one exemplary embodiment, the sterilization unit has low-powered e-beam emitters that provide a sterile environment for the filling and capping of products such as beverages, liquids, or foods, etc. The sterilization unit and other associated structures and systems provide the active sterilization zone in the CHE in which the containers travel. The sterilization technique disclosed herein can be used to sterilize any type of container whether the container is adapted to receive, for example, filtered, preserved, or pasteurized product. The product is maintained at a generally ambient temperature. The sterile filled and capped containers are then directed for further packaging.

A apparatus and method for sterilizing components of a transfer wheel is disclosed. The transfer wheel is configured to transfer open filled containers from a filler assembly to a capping assembly and has an air management system. The system has a conduit for the supply of air in a downward direction past the containers on the transfer wheel. The conduit has an inlet duct adapted to be in communication with the supply of air and has an outlet manifold having an opening and the supply of air is directed through the opening. The outlet manifold has a curved shape, is positioned on a portion of the transfer wheel, has an open bottom section, has a generally horizontal top surface, and has a pair of spaced sidewalls depending from the top surface. A mesh screen is positioned in the opening proximate the top surface. The outlet manifold has a generally inverted U-shaped cross-section.

An apparatus and method for receiving a sterile container and delivering the sterile container to a filler assembly is disclosed. The apparatus has a housing consisting of a container inlet opening, a container outlet opening, and an air inlet opening. A shroud is positioned around the container inlet opening and has an open bottom end. An intake conveyor is positioned in the housing and is adapted to receive the sterile container through the container inlet opening and pass the sterile container to the container outlet opening. An air source is in communication with the air inlet opening, and the housing receives the air, and the air passes from the open bottom end. The air inlet opening is positioned on the ceiling of the housing. The filtered air source pressurizes the housing and can be ULPA/HEPA filtered air. The intake conveyor has an intake wheel consisting of a gripper, and the gripper is adapted to grip a container delivered from a container sterilizer and pass the container to the container outlet opening. The intake conveyor also has a first intake wheel operably associated with a second intake wheel, and the first intake wheel is adapted to receive the container from a container sterilizer and to pass the container to the second intake wheel. The second intake wheel is adapted to pass the container to the container outlet opening. The housing has an access door and a container reject mechanism. Unacceptable containers are removed from the conveyor and can be accessed through the access door. Additionally an air cylinder having one end connected to the housing and another end connected to the access door is provided. The air cylinder is operable to open and close the access door. The housing floor is slanted towards the access door to provide a ramped surface for the unacceptable containers.

Other features and advantages of the invention will be apparent from the following specification taken in conjunction with the following drawings.

BRIEF DESCRIPTION OF THE DRAWINGS

To understand the present invention, it will now be described by way of example, with reference to the accompanying drawings in which:

FIGS. 11 and 11a are a partial perspective views of the second module of the system of an exemplary embodiment;

FIG. 15a is a partial cross-sectional view of filler grippers;

FIG. 42 is a partial cross-sectional view of the filler assembly;

DETAILED DESCRIPTION

Figure 1:
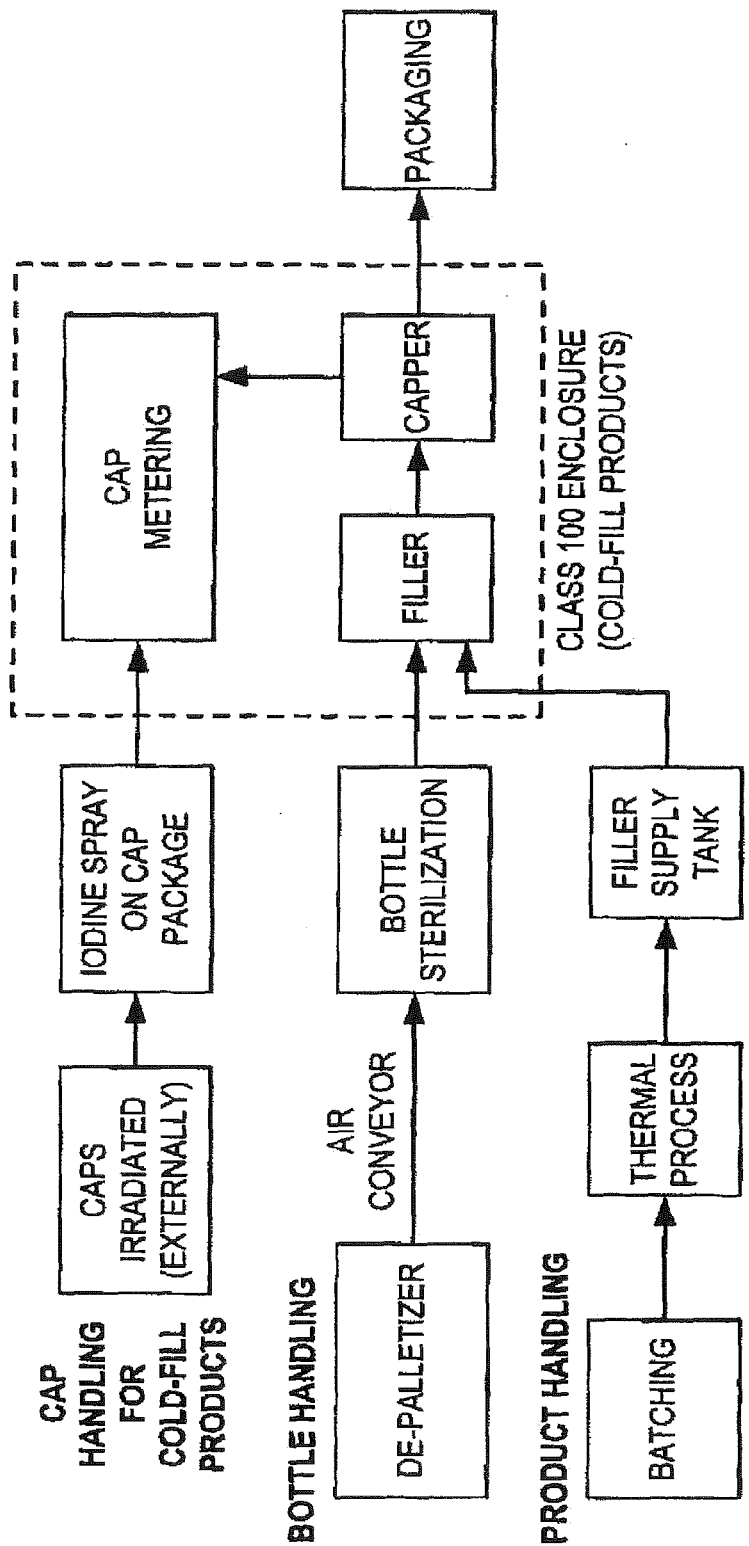
FIG. 1 is a prior art schematic diagram of a container filling process.
Figure 2:
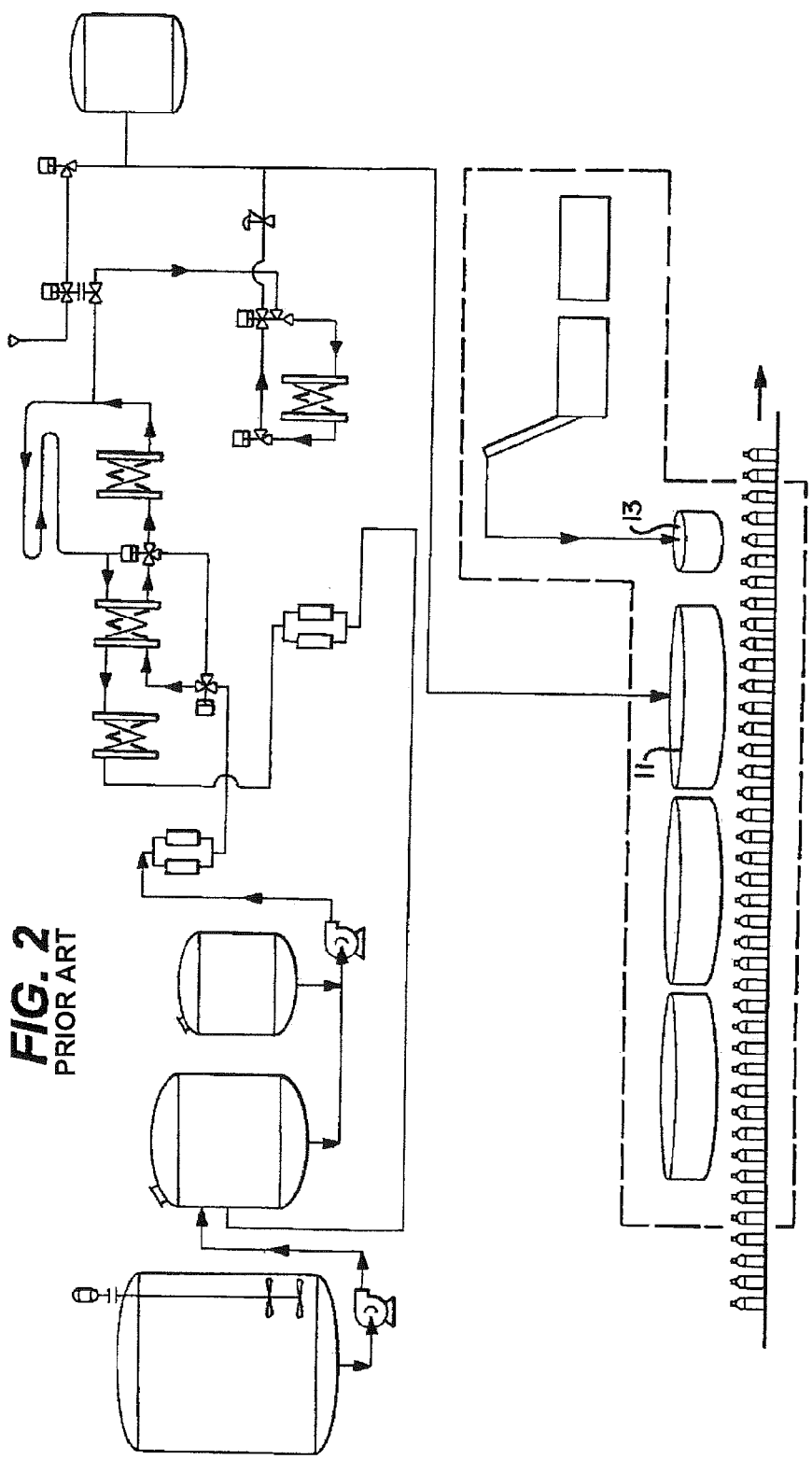
FIG. 2 is a schematic diagram of a conventional aseptic cold-fill container filling process.
Figure 3:
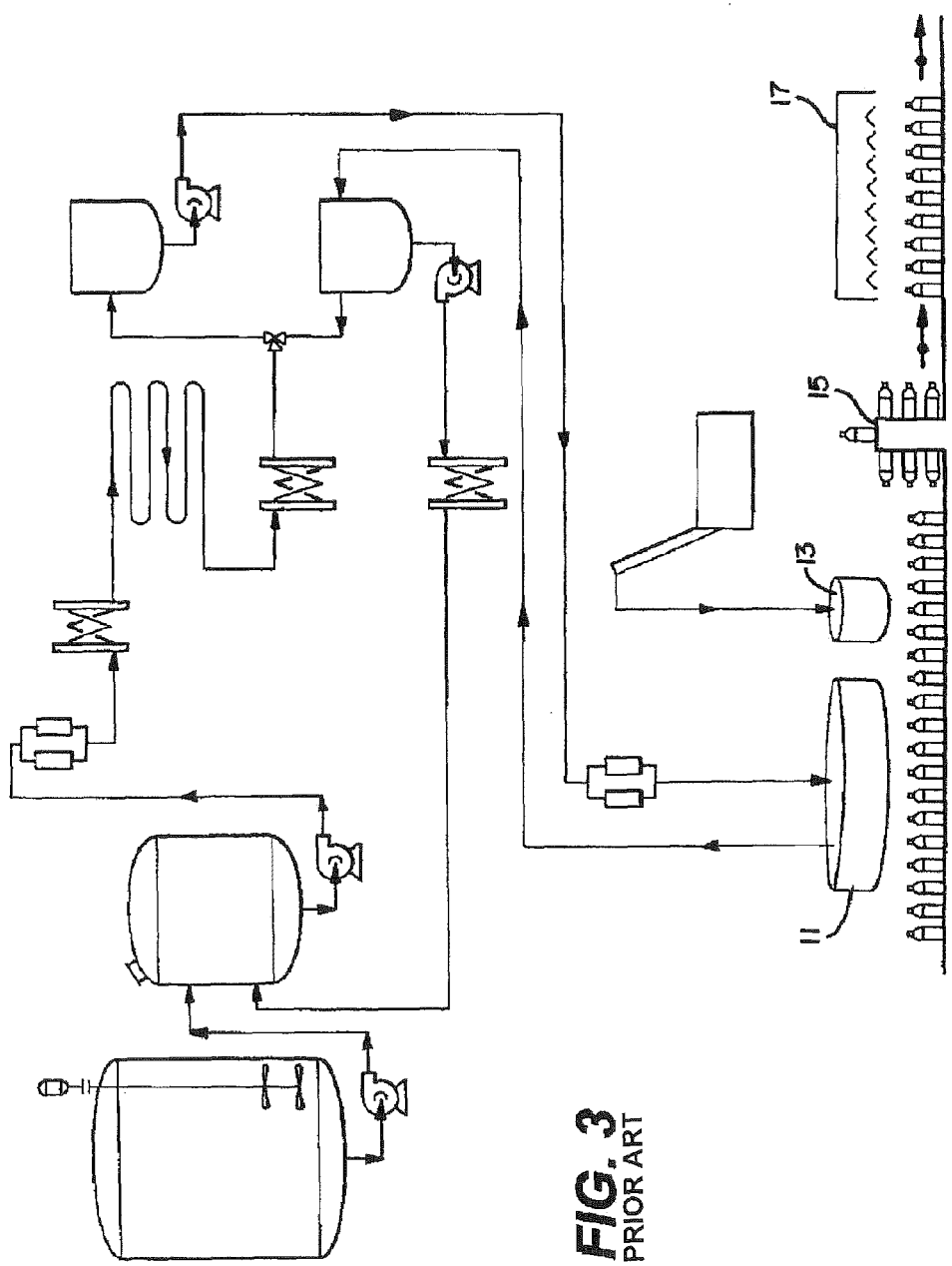
FIG. 3 is a schematic diagram of a conventional hot-fill container filling process.

While this invention is susceptible of embodiments in many different forms, there are shown in the drawings and will herein be described in detail exemplary embodiments of the invention with the understanding that the present disclosure is to be considered as an exemplification of the principles of the invention and is not intended to limit the broad aspect of the invention to the embodiments illustrated.

Figure 4:
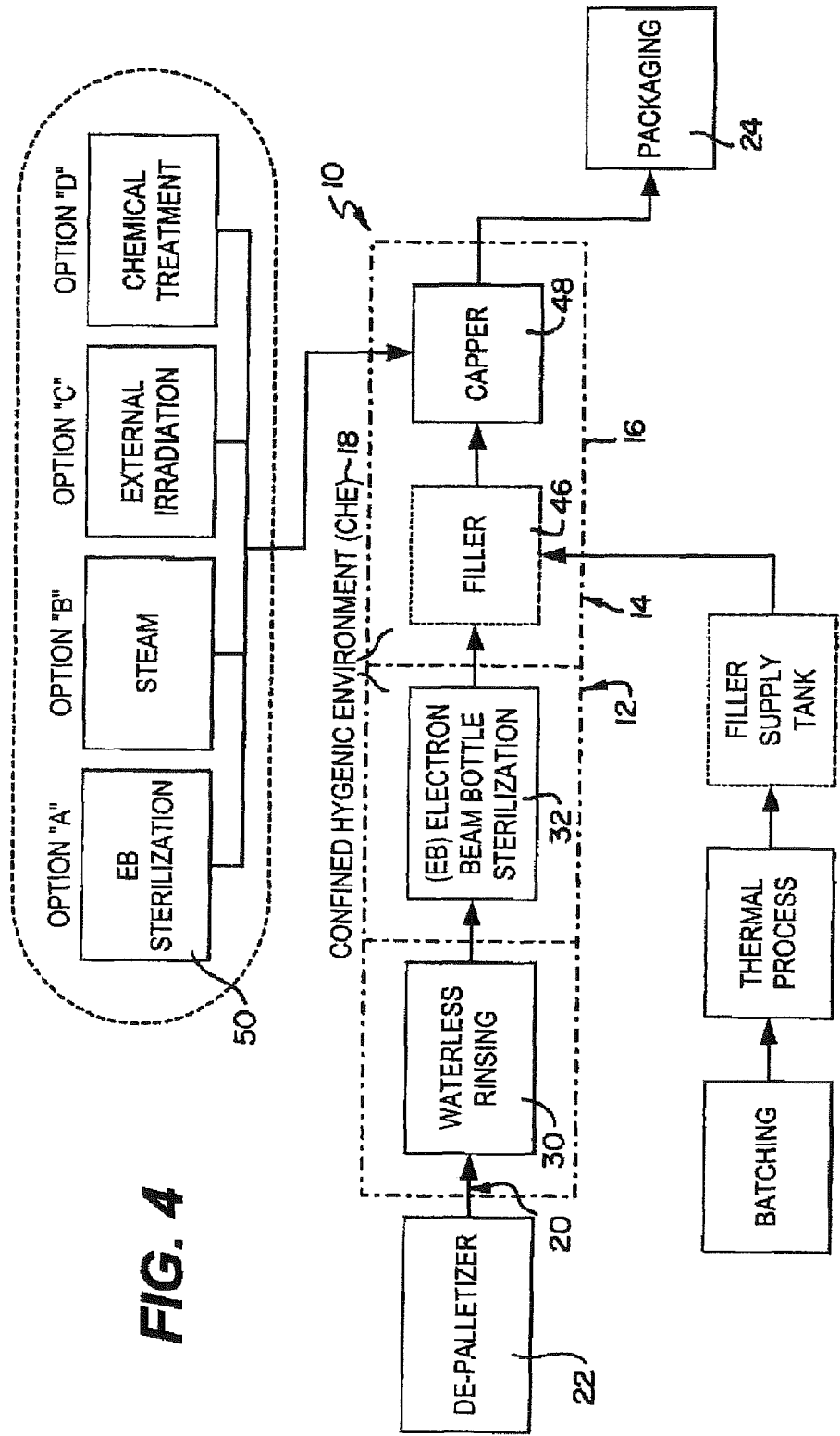
FIG. 4 is a block diagram of an active sterilization ambient-fill process according to an exemplary embodiment.
Figure 5:
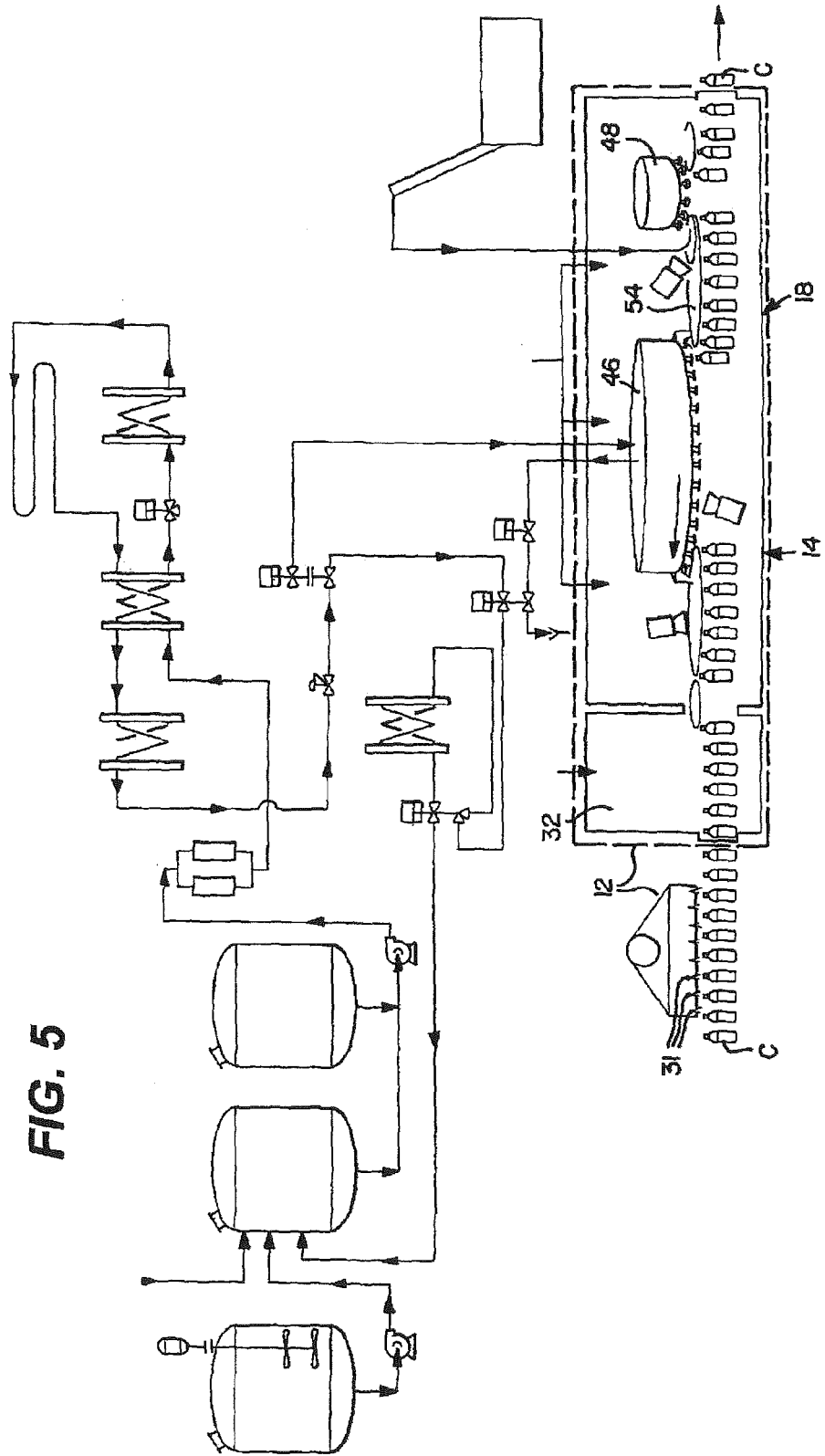
FIG. 5 is a schematic diagram of the active sterilization ambient-fill system/process according to an exemplary embodiment.
Figure 6:
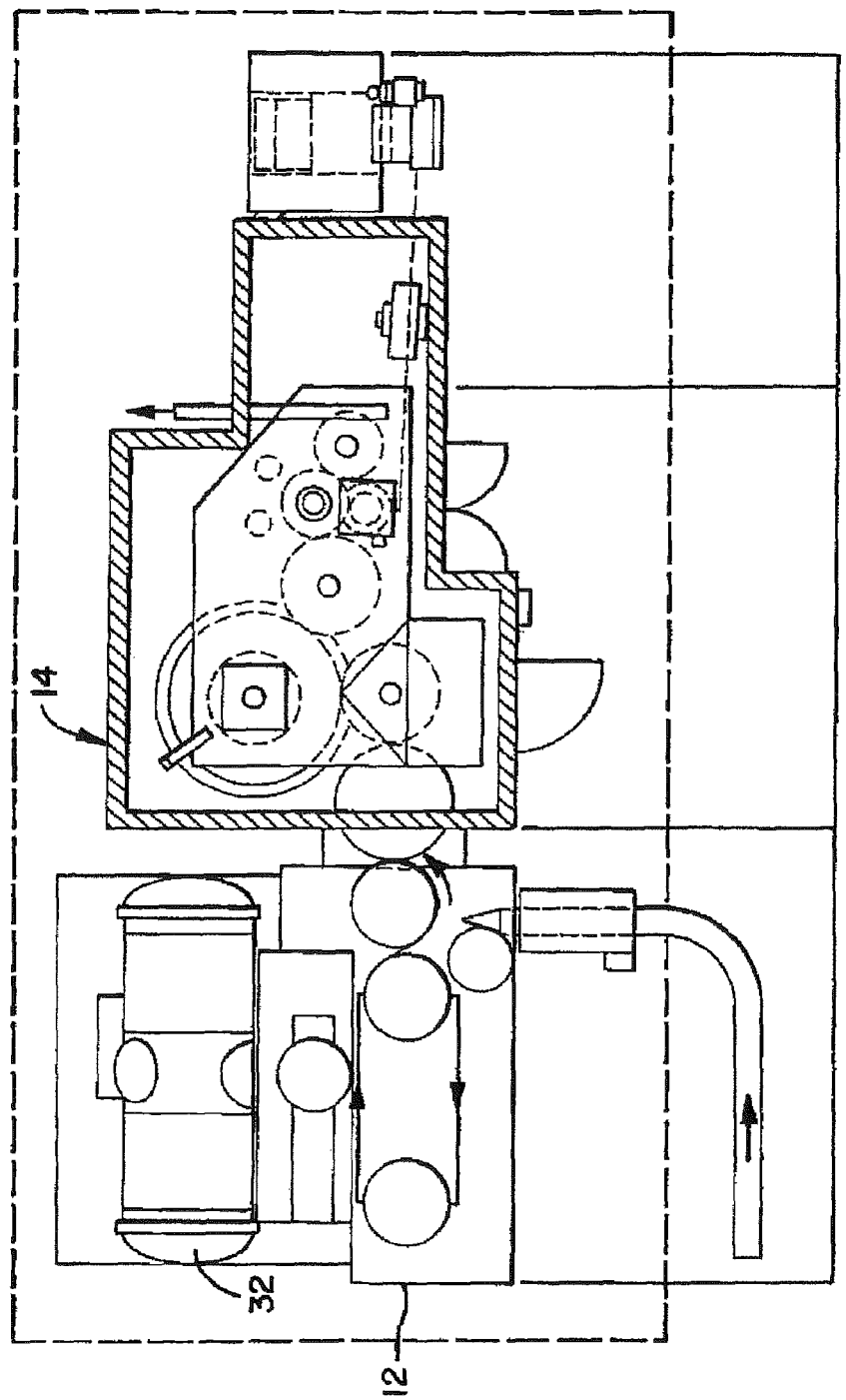
FIG. 6 is a schematic diagram of the active sterilization ambient-fill system/process according to an exemplary embodiment and showing a first module and a second module.

Referring now to the FIGS., and initially to FIGS. 4-6, there is shown an exemplary embodiment of an apparatus for sterile filling of containers, generally designated with the reference numeral 10. In one exemplary embodiment, the containers are beverage containers, although the system 10 can be used in various other container applications requiring sterile filling and closing. The system 10 generally includes a first module, or station 12 and a second module or station 14. The first station 12 and the second station 14 have certain associated structures 16, as explained in greater detail below, that cooperatively define a confined hygienic environment ("CHE") 18. As explained in greater detail below, the CHE 18 can take various forms among the different exemplary embodiments disclosed herein. For example, in one exemplary embodiment, the CHE 18 may be operably associated with the second module 14. An in-line conveyor assembly 20 is utilized as part of the system 10 to transport a plurality of containers C through the first module or station 12 and the second module or station 14 as explained in greater detail below.

Referring to FIG. 4, the first module 12 generally includes a de-palletizer 22, a waterless rinser 30 and a container sterilizer 32. The second module 14 generally includes a filler assembly 46 and a capper assembly 48. In a further exemplary embodiment (depicted schematically in FIG. 10), the second module 14 may further include an e-beam sterilization unit 50, an isolator assembly 52, the filler assembly 46, a transfer mechanism 54, the capper assembly 48, and an environment control system 56. As shown in FIG. 4 and discussed further below, the capper assembly 48 may utilize e-beam sterilization as part of the e-beam sterilization unit 50, however, other sterilization methods may also be employed for the capper assembly including steam, external irradiation and chemical treatment as shown in FIG. 4. FIG. 4 further shows that the product to be injected into the containers C may proceed through batching, a thermal process and to a filler supply tank prior to being delivered to the filler assembly 46. FIG. 5 shows an additional schematic view of the first module 12 and the second module 14 and also shows additional detail regarding the batching process for the beverage product to be injected into the plurality of containers C. The general structures of the first module 12 and the second module 14 will first be described followed by a description of the operation of the first and second modules 12, 14.

Conveyor Assembly

As further shown schematically in FIGS. 4-6, the conveyor assembly 20, is an in-line system capable of transporting a plurality of containers in an automated fashion. The conveyor assembly 20, has conventional structure known in the art and includes structures for general transport as well as gripping structures for moving the containers through the system 10, via generally linear and arcuate paths as necessary. In particular, the conveyor assembly 20, may transport the containers C via the container neck. The conveyor assembly 20 may have a plurality of individual conveyors operably connected to one another to transport containers from the de-palletizer station, designated 22 in FIG. 4, through the system 10, and to further packaging mechanisms, designated 24 in FIG. 4, as desired. It is understood that other components of the first module 12 and the second module 14 may also form a portion of the conveyor assembly 20 such as the various wheels used to transport the containers C through the system 10. In one exemplary embodiment, many portions of the conveyor assembly 20 are rotary-type conveyors. It is understood that other types of conveyors can be employed such as conveyors that transport containers in a linear fashion or indexing arrangement. Alternate conveyor assemblies could also transport containers C via a base of the containers C as opposed to a neck portion.

First Module

As discussed, the first module 12 includes the de-palletizer 22, the waterless rinser 30 and the container sterilizer 32. Empty containers C are typically delivered to the system 10 on pallets. The de-palletizer 22 is a known structure used to remove the empty containers C from pallets and to the conveyor assembly 20. As further shown in FIG. 5, the waterless rinser 30 may include a plurality of air nozzles 31 arranged in series fashion. The waterless rinsing station 30 receives empty containers C from the conveyor assembly 20 and initially rinses the containers C to remove bio-load and foreign matter. The waterless rinser 30 is not considered to be part of the CHE 18 but is helpful to help prevent foreign matter from entering into the CHE 18. As can be appreciated from FIGS. 5 and 6, the conveyor assembly 20 then transports the containers to the container sterilizer 32.

Container Sterilizer

Figure 8:
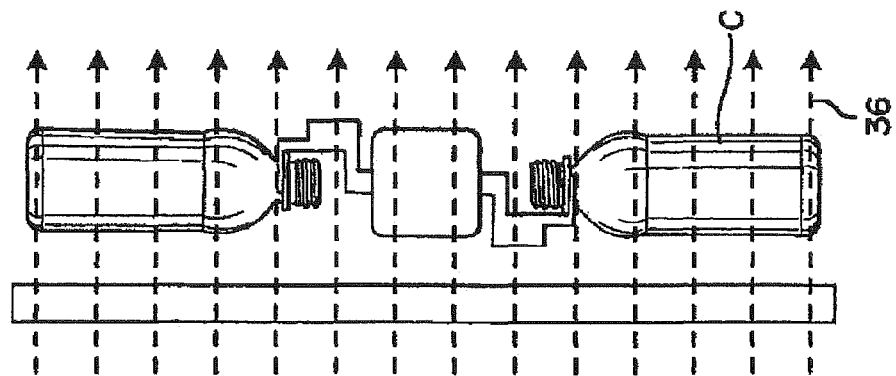
FIG. 8 is a schematic view of two containers in an electron field showing container gripping and container inversion.
Figure 7:
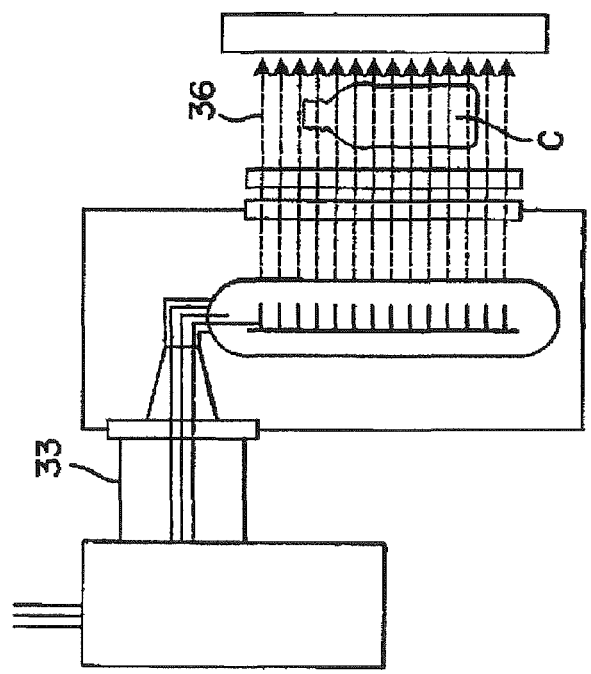
FIG. 7 is a schematic view of a container in an electron field produced by an e-beam emitter/sterilizer.
Figure 9:
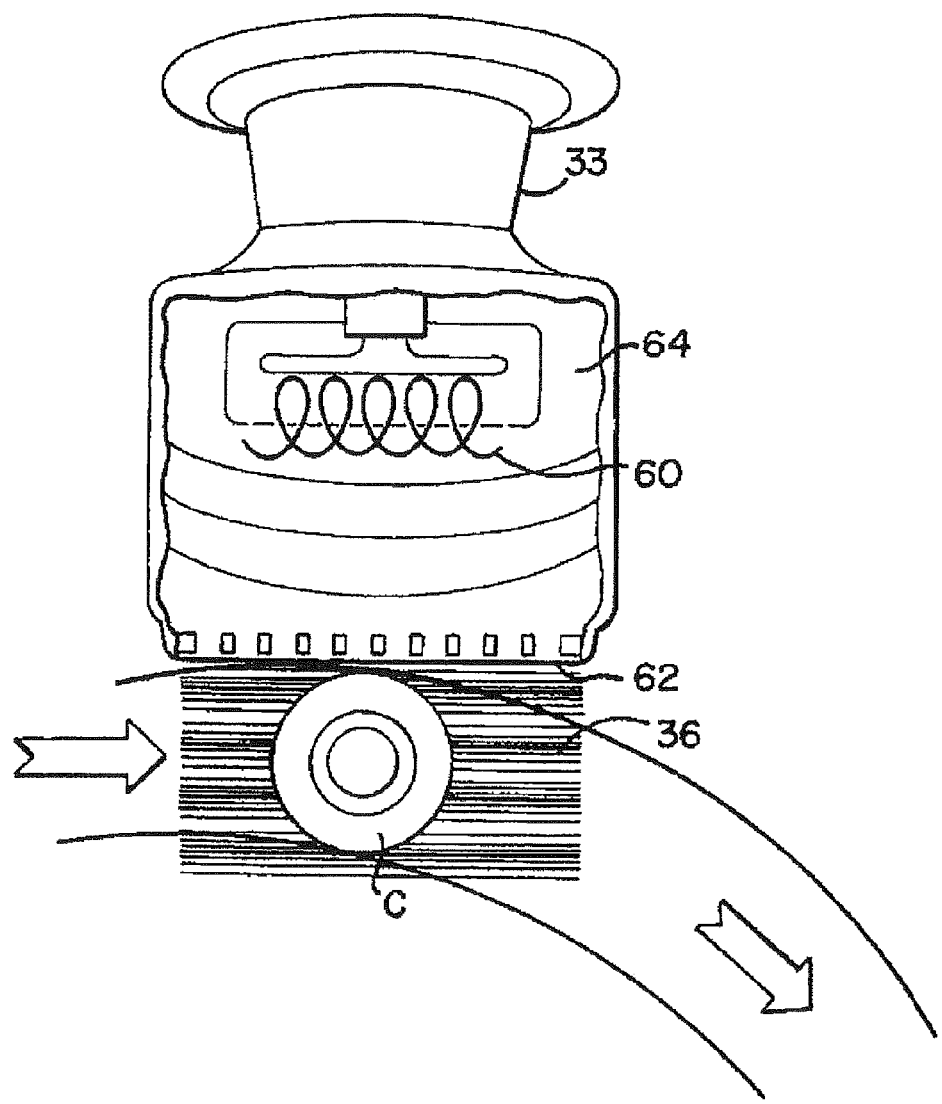
FIG. 9 is a schematic diagram of an e-beam emitter generating an electronic field and a container passing therethrough.

In one exemplary embodiment, the container sterilizer 32 can use e-beam emitters 33 as an electron source to sterilize the containers C. Any known method, however, can be used to sterilize the containers C. The e-beam container sterilizer 32 can include a high-powered electron beam emitter 33, shown in FIGS. 6-9. The container sterilizer 32 accommodates portions of the conveyor assembly 20, for in-line sterilization of the containers C. FIGS. 7-9 schematically show portions of the container sterilizer 32 wherein the e-beam emitter 33 produces an active sterile electron field 36 or e-beam field 36.

Once inside the container sterilizer 32, the containers C can be gripped by the neck of the container C and conveyed through a field of electron beams emitted by the e-beam emitter 33 that form the active sterile field 36. The container C may be inverted and rotated for a second pass through the electron field 36 so that all sides of the container C are assured to pass through the sterile field of electron beams 36 as shown in FIGS. 7 and 9. This insures sterilization of all sides of the container C and any and all cold spots around the finish and bottom of the container C. The sterile field 36 prevents reproduction, stops further multiplication, and ends growth of any remaining bio-load. Preventing reproduction is equivalent to killing the organism. Once the sterilizer 32 sterilizes the containers C, an air purge is provided to remove ozone created inside the container C. The air is exhausted from the module and treated prior to release into the atmosphere. The container sterilizer 32 produces, via the e-beam emitter 33, the active sterile field 36 that encompasses the conveyor pathway in which the container C travels.

E-Beam Generator in Container Sterilizer

FIG. 9 shows a schematic view of one type of electron beam emitter 33. In the electron beam emitter 33, electrons are transferred from a filament 60. The filament 60 is housed in a vacuum chamber 64, for accelerating the electrons. A titanium window 62 is provided that separates the atmosphere 66 and the vacuum chamber 64. The electrons are accelerated through the window 62, and thereby create the active sterile electron field 36, which extends a suitable distance and covers a suitable area to sterilize the containers C. In one exemplary embodiment, the e-beam emitter 33 is designed to provide a radiation dose of approximately 10-15 kGy to all surfaces of each container C, thereby achieving about a 6 log count reduction ("LCR") of microbes on the container surfaces.

Such emitters 33 may be considered high-energy e-beam emitters. The beams, however, can be generated by a suitable e-beam emitter having such energy capabilities. Such a unit is capable of generating electron beams that are of sufficient strength to sterilize the interior and exterior of a container.

The containers C are then transported out of the container sterilizer 32 and to the second module 14. The container sterilizer 32 thus prepares a sterile container C to be delivered to the second module 14 for filling with a product in an active sterilization zone in the CHE 18.

As discussed above, in one exemplary embodiment, the container sterilizer 32 utilizes a high energy e-beam emitter for sterilization. It is understood that the container sterilizer 32 in the first module 12 can utilize other forms of sterilization, for example, irradiation, chemical, or heat/temperature sterilization. Thus, other sterilizing structures and processes can be used to provide a sterile container C to the second module 14.

Second Module 14

Figure 10:
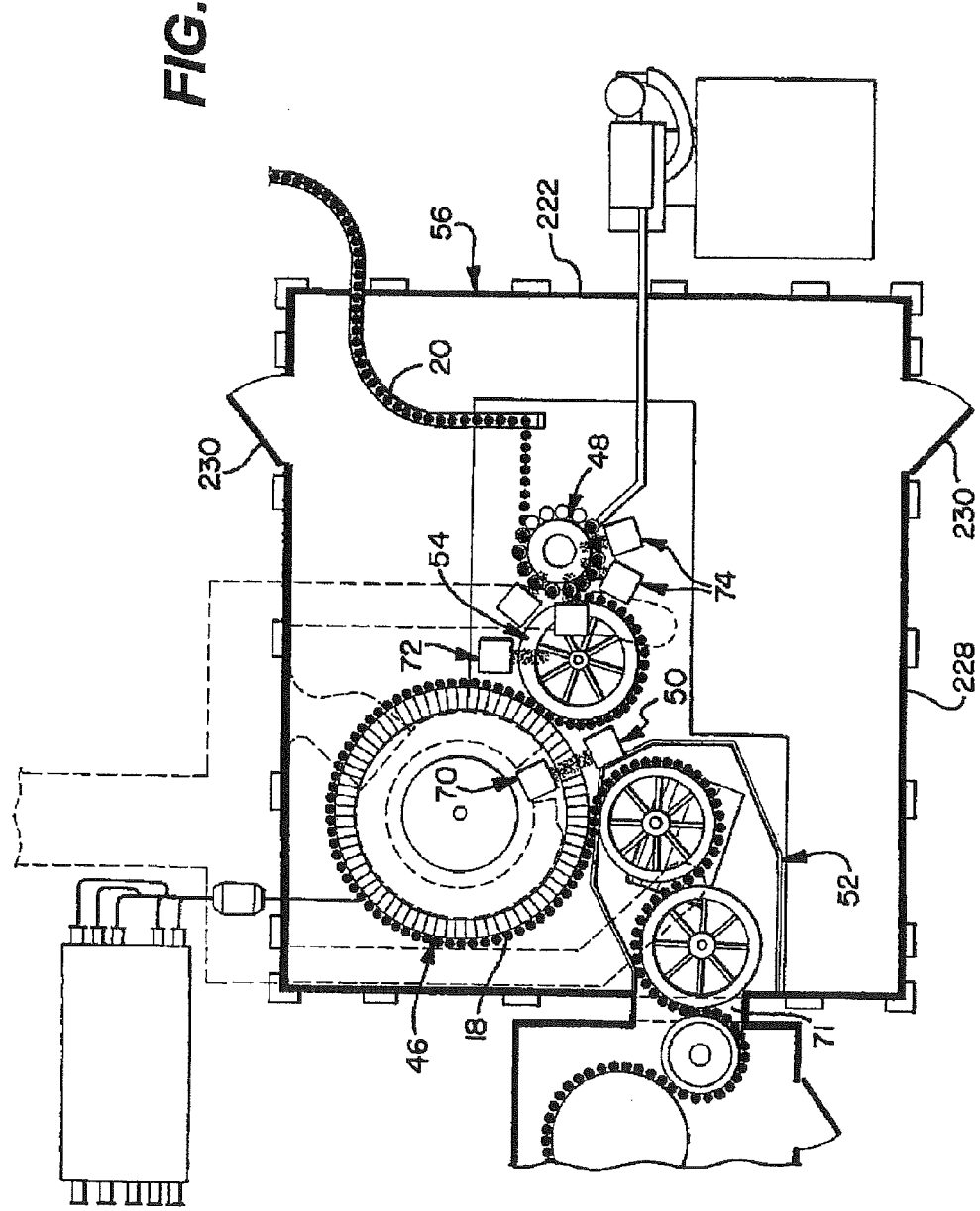
FIG. 10 is a schematic plan view of a second module of the system of an exemplary embodiment.
Figure 11:
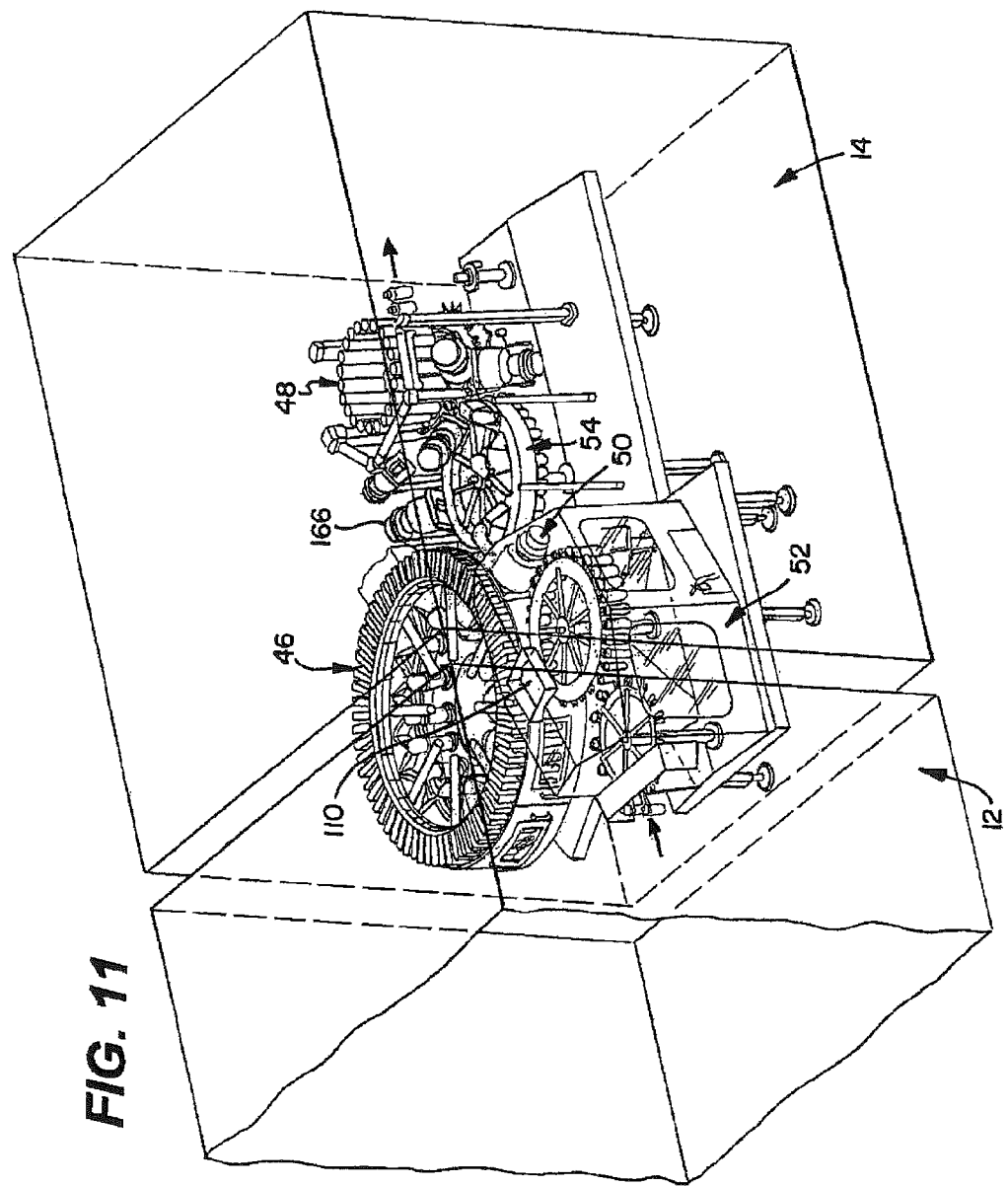

After sterilization of the containers C in the first module 12, the containers C are delivered to the second module 14 for further processing. As discussed, in the second module 14, the containers C are filled with product in an active sterilization zone in the CHE 18, capped and delivered for further packaging. As discussed, in one exemplary embodiment as shown in FIGS. 10 and 11, the second module 14 generally includes the e-beam sterilization unit 50, the isolator assembly 52, the filler assembly 46, the transfer mechanism 54, the capper assembly 48 and the environment control system 56. These components will now be described in greater detail. Portions of the conveyor assembly 20 assist in moving the containers C through the second module 14.

E-Beam Sterilization Unit

Figure 30:
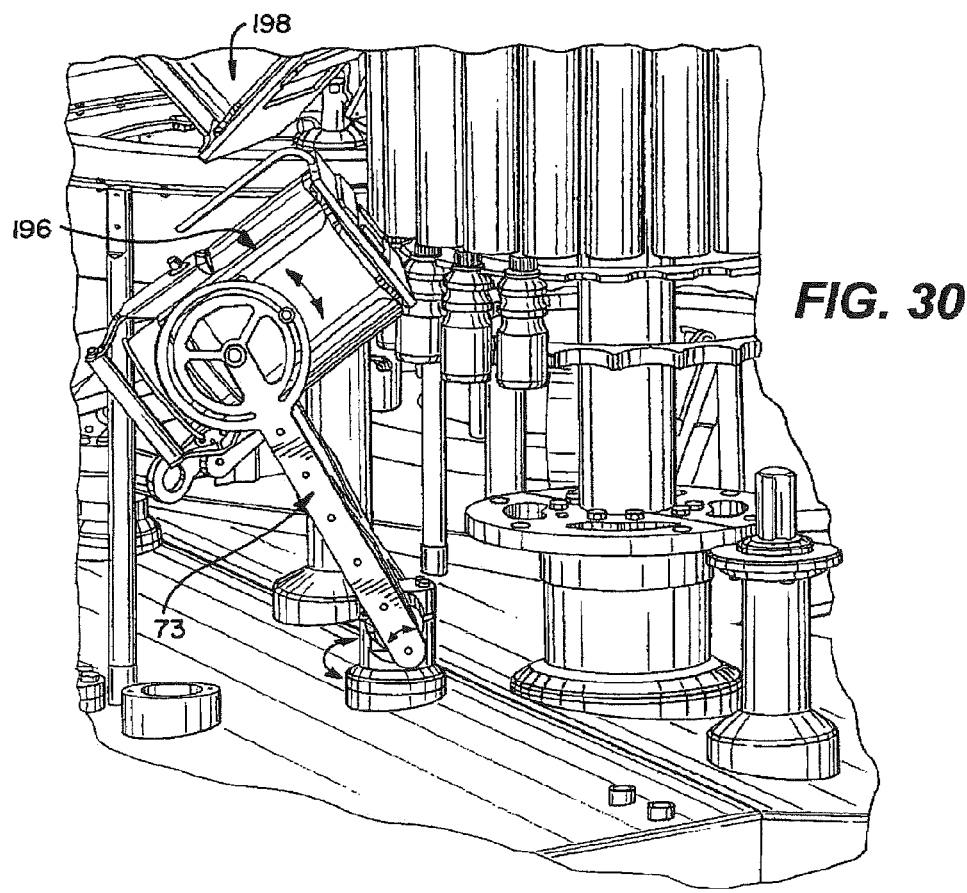
FIGS. 30-32 are partial perspective views showing the capper assembly of the second module.
Figure 31:
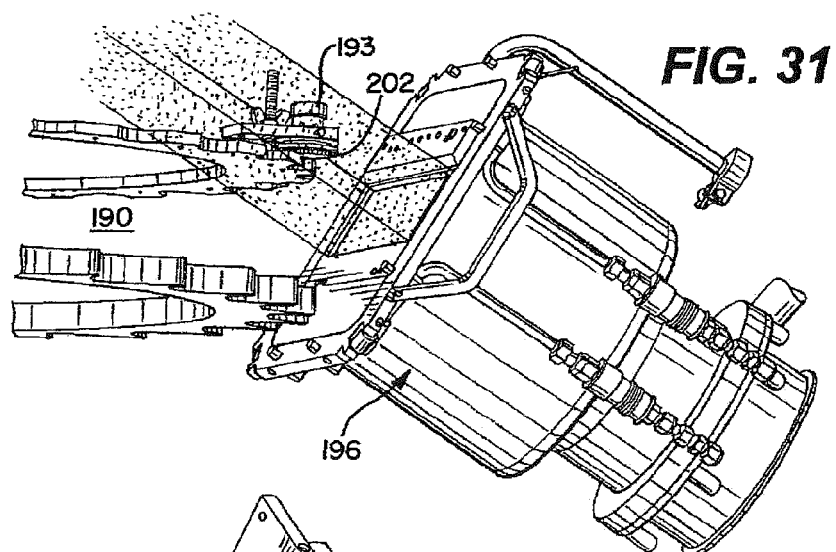

The e-beam sterilization unit 50 includes a plurality of e-beam emitters placed at certain positions and areas within container travel zones within the second module 14 such that only critical machine surfaces, components, and air immediately surrounding the components are subjected to the e-beams and not the beverage product itself. The e-beam sterilization unit 50 forms part of the CHE 18 of the second module 14. In an exemplary embodiment, the e-beam emitters are low-energy e-beam emitters. In a particular embodiment, the e-beam emitters are 150 kV models. It is understood that other suitable e-beams emitters can be used. The e-beam sterilization unit 50 generally includes a filler wheel sterilization unit 70, a transfer mechanism sterilization unit 72, and a capper assembly sterilization unit 74. In one exemplary embodiment, the e-beam emitters have an outlet window 3 in. by 10 in. in size although this size can vary as desired. The e-beam emitters are typically mounted on yokes 73 and are fully articulating in x, y, z axes, as depicted in FIG. 30. The e-beam fields emitted by the e-beam emitters may be configured in a horizontal fashion, vertical fashion or at some other angle as desired. Additional structures regarding these sterilization units will be further described below in conjunction with the other structures of the second module 14. Operation of these e-beam emitters will also be described in greater detail below. As will be appreciated from the description below, the various e-beam emitters sterilize certain components of the second module 14 during operation of the system 10 when containers are being filled and capped. Thus, the e-beam emitters provide active sterilization, or re-sterilization of components as the system 10 operates.

Isolator

Containers C sterilized by the first module 14 are first delivered to the isolator assembly 52 of the second module 14. As shown in FIGS. 10-14, the isolator assembly 52 generally includes an air lock structure 76, a first intake wheel 78, a second intake wheel 80 and a housing 82 having an air system 84 operably associated therewith.

Figure 12:
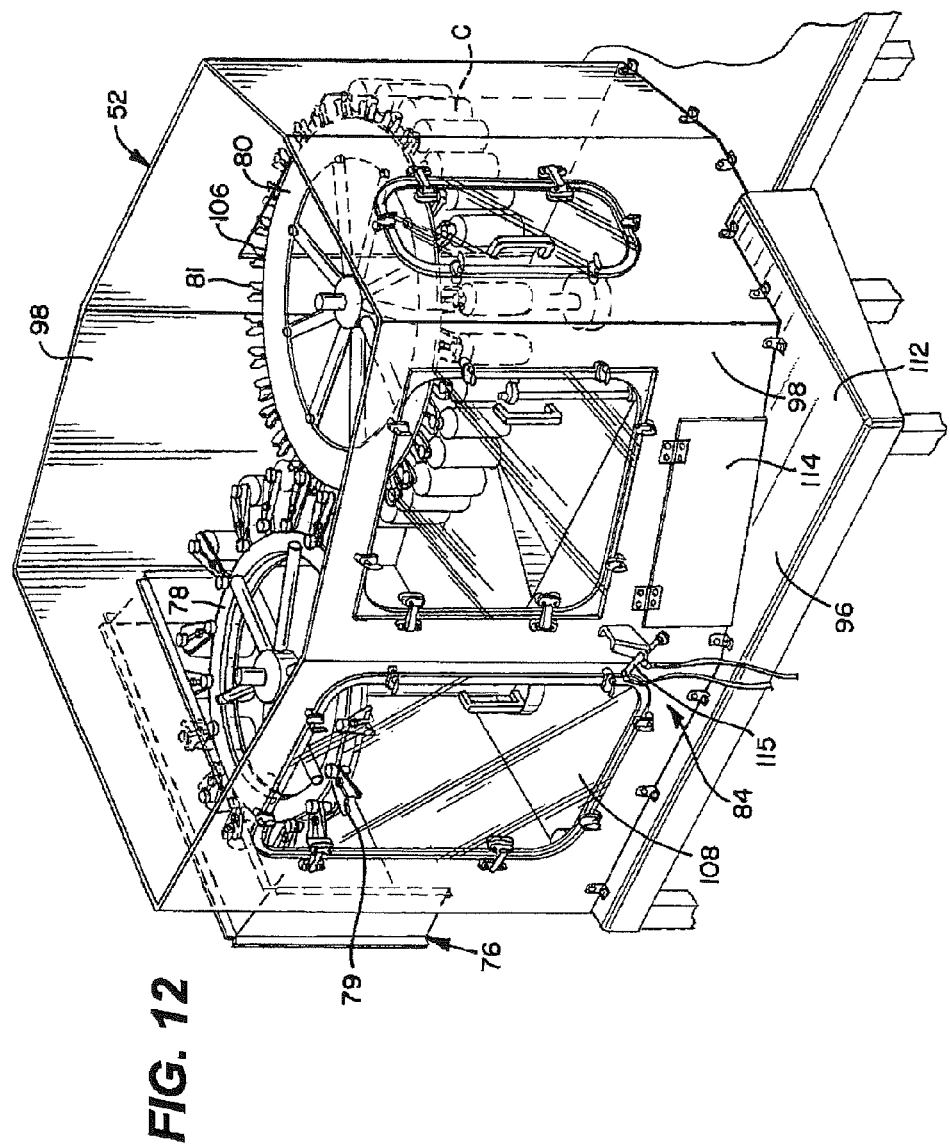
FIG. 12 is a perspective view of an isolator assembly of the second module of the system of an exemplary embodiment.
Figure 14:
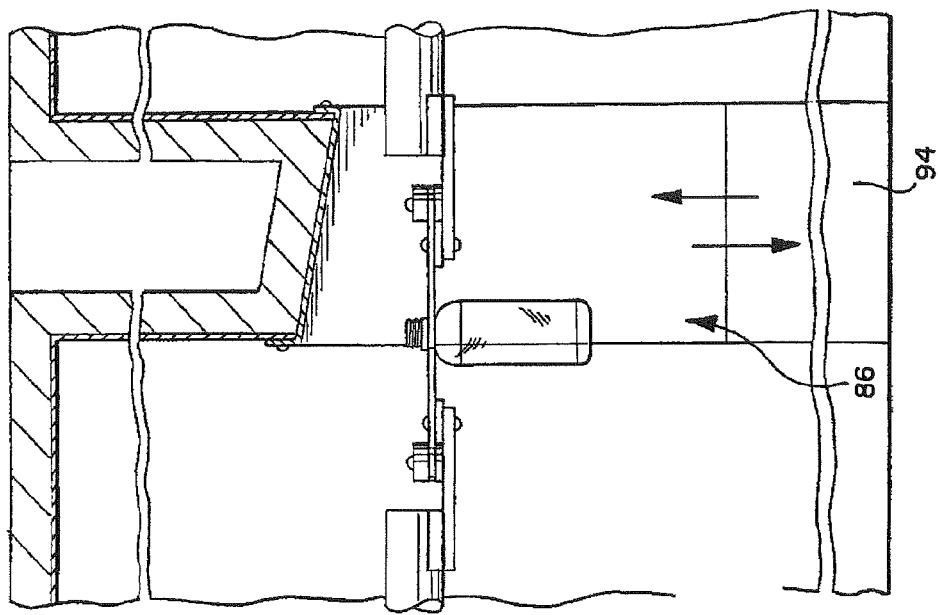
FIG. 14 is a schematic partial cross-sectional view of an interface area between the first module and second module of the system of an exemplary embodiment.
Figure 13:
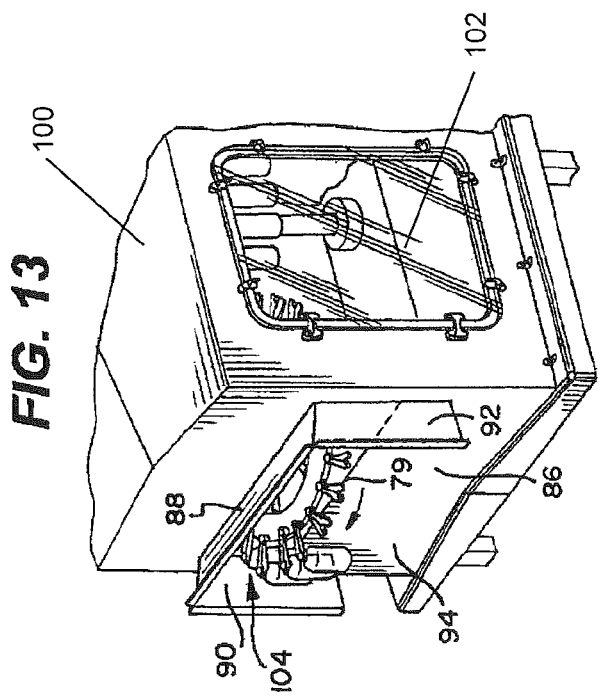
FIG. 13 is a partial perspective view of the isolator assembly.

As shown in FIG. 12-14, the air lock structure 76 is positioned at an interface area 86 between the first module 12 and the second module 14 and, in particular, at the inlet of the isolator assembly 52. The air lock structure 76 has a horizontal wall 88 and first depending wall 90 and a second depending wall 92 and defining an open bottom end 94. The air lock structure 76 provides a shroud structure. The walls 88, 90, 92 are connected to a dividing wall of the first module 12 and, therefore, generally provides a seal around the opening between the first module 12 and the second module 14. The first intake wheel 78 has a plurality of grippers 79 and is positioned such that as the wheel 78 rotates, the grippers 79 are proximate the air lock structure 76. As will be explained in greater detail below, the grippers 79 cooperate with a wheel with grippers of the first module 12 to receive sterile containers C from the first module 12. The second intake wheel 80 has a plurality of grippers 81 and is positioned proximate the first intake wheel 78 and cooperates therewith as described below. It is understood that the first intake wheel 78 and second intake wheel 80 are powered and have appropriate systems for rotation and operation of the respective grippers 79, 81. It is further understood that a single intake wheel could be employed if appropriate sizing and number of grippers was compatible with the size of the filler assembly 46 and transfer wheel associated with the first module 12.

The housing 82 of the isolator assembly 52 has a floor 96, a plurality of sidewall members 98 and top member 100 defining an enclosure 102 that is positioned around the first intake wheel 78 and the second intake wheel 80. One sidewall member 98 has a container inlet opening 104 and is connected to the air lock structure 76 wherein the air lock structure 76 is in communication with the enclosure 102. A second side wall 98 is provided with a container outlet opening 106 positioned proximate the filler assembly 46. The side wall members 98 may have a window 108 for operators to see into the housing 82. The windows 108 each have hinges to allow for easy access to the first intake wheel 78 and the second intake wheel 80. The windows 108 can further have window locks and seals placed around the perimeter of each window 108. The top member 100 has an opening 110 that serves as an air inlet for connection to an air duct of an air management system to be described in greater detail below. The air supply assists in maintaining a positive pressure and downward flow into the housing 82 and out of the open bottom 94 of the air lock structure 76. The floor can have a slanted portion 112 towards one of the sidewall members 98, which may be equipped with an access door 114. The access door 114 may be equipped with an air cylinder 115 operably connected between the sidewall 98 and the door 114 to provide automated opening and closing of the door 114. The sidewall members 98 can be formed from individual layers of lead and plywood with a stainless steel covering. The members 98 may be provided with a rubber seal, which may abut around the air lock structure 76 and against the first module 12 to provide additional sealing. The isolator assembly 52 can be provided with a container reject mechanism associated with the second intake wheel 80. A container reject mechanism is adapted to reject containers unsuitable for filling, such as containers inadvertently deformed during the sterilization process in the first module 12. The container reject mechanism can be provided with a cam that is adapted to open the grippers and a sensing mechanism that is adapted to sense deformed containers.

It is noted that depending on the characteristics of the type of the filler assembly used and the type of first module used, alternative structures to the isolator assembly 52 can be used to transfer containers from the first module to the filler assembly. In this exemplary embodiment a structure or intake conveyor is used to accept a sterile container C from the first module 12 and deliver the container C to the filler assembly 46. The isolator assembly 52 achieves this in the exemplary embodiment as the isolator assembly 52 is in an initial sterile condition and remains in such condition during operation of the system 10.

Filler Assembly 46

The filler assembly 46 includes components to receive the sterile containers C and further to receive a supply of batched, finished product such as a liquid beverage to be injected or filled into the containers C. The filler assembly 46 generally includes a filler wheel 47, the filler wheel sterilization unit 70, and a filler wheel air management/isolation system 118.

Figure 15:
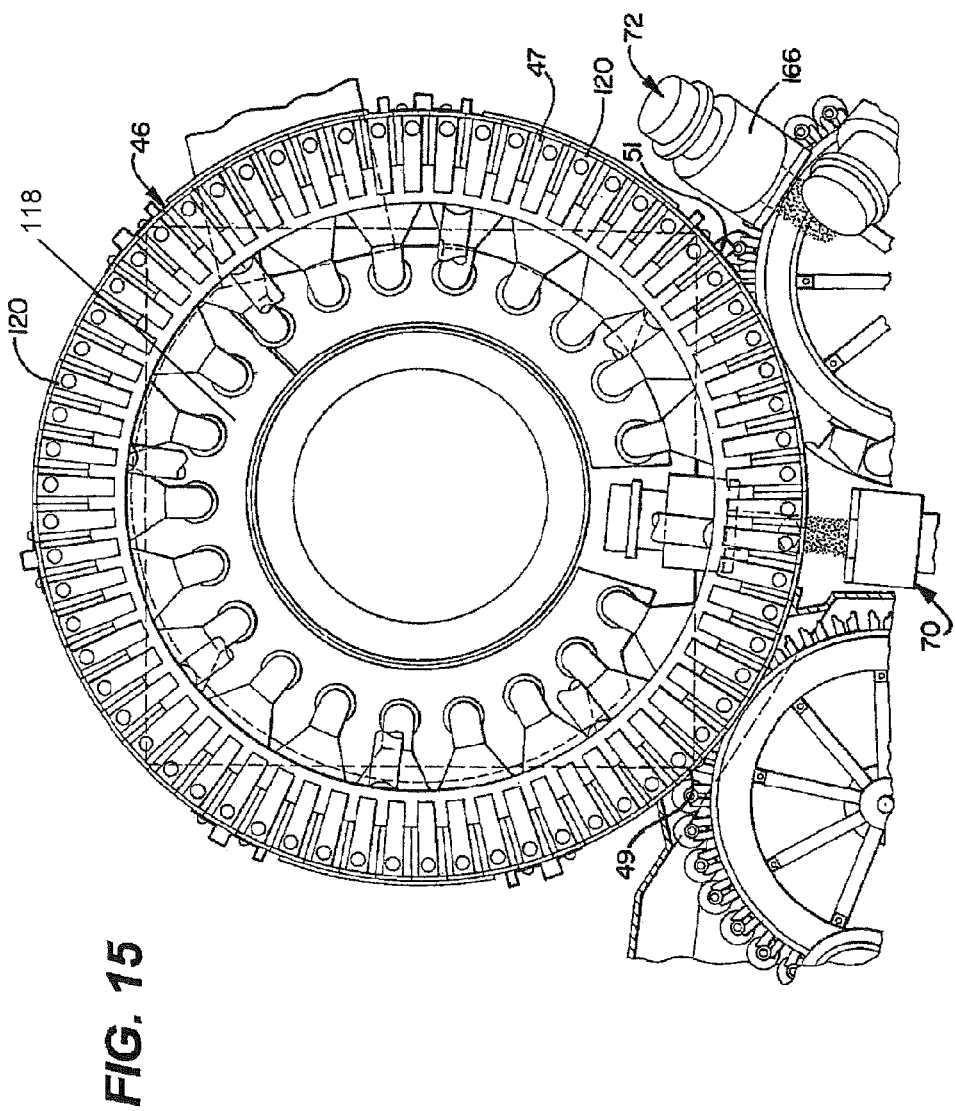
FIG. 15 is a partial plan view of the second module and showing a filler assembly.
Figure 16:
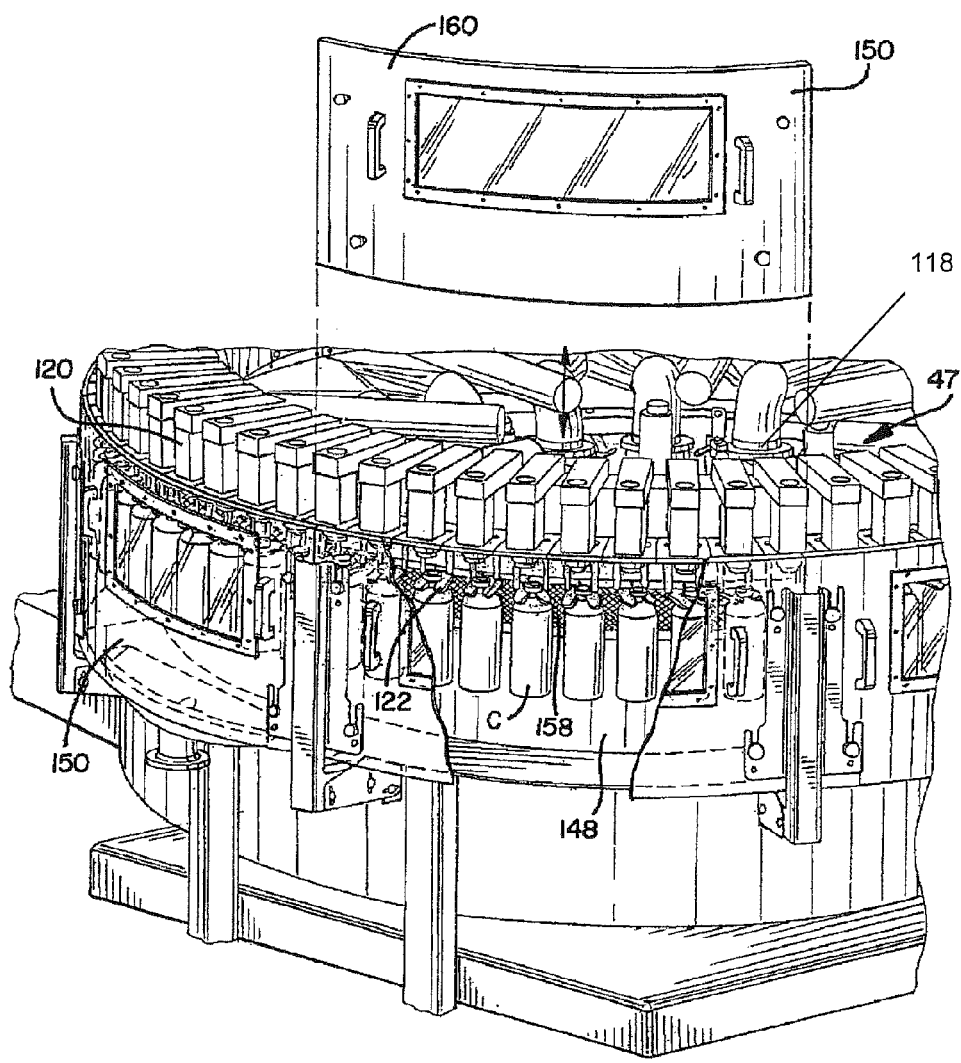
FIG. 16 is a partial perspective view of the filler assembly.

The filler wheel 47 is a generally circular structure and has supporting systems for rotation. As shown in FIGS. 15 and 15a, the filler wheel 47 has a plurality of filler valves 120 positioned generally adjacent one another and at a periphery of the filler wheel 47. The filler valves 120 are operably in fluid communication with the supply of the batched product through suitable conduits, lines, or hoses as is known. In the exemplary embodiment, the filler valves 120 are non-contact valves which do not contact the containers C; however, it is noted that contact valves can be used. The filler wheel 47 further has a plurality of filler grippers 122 corresponding to the number of filler valves 120. The grippers 122 are positioned generally below the filler valves 120 and grip the containers C received from the second intake wheel 80 of the isolator assembly 52. The filler wheel has a container inlet portion 49 and a container outlet portion 51. The filler wheel 47 is generally positioned proximate the second intake wheel 80. While the filler wheel 47 is a rotary mechanism, other types of fillers can be used such as linear fillers.

Figure 41:
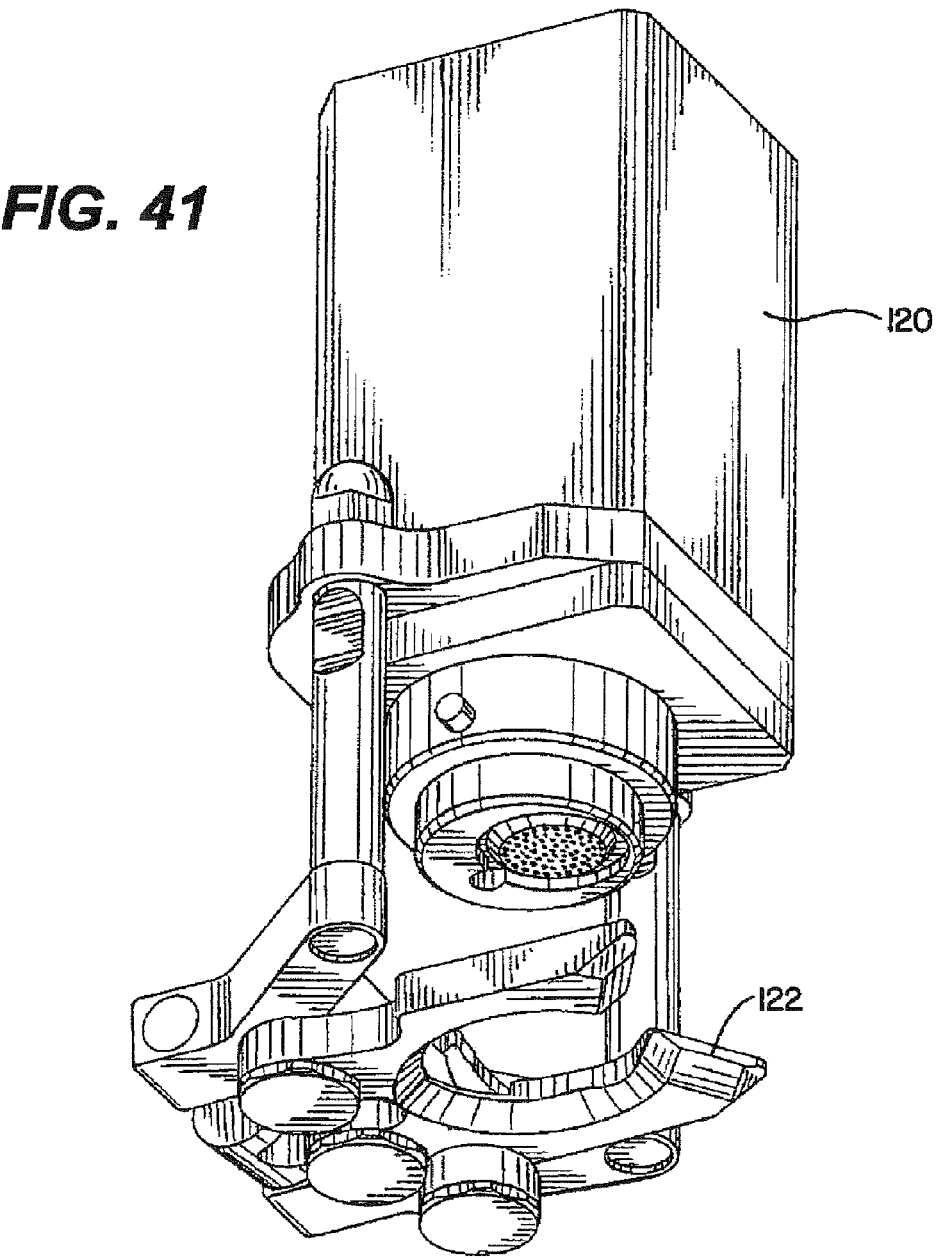
FIG. 41 is a perspective view of a filler valve.

An exemplary filler valve 120 is depicted in FIGS. 41 and 42. As shown in FIG. 41, the filler valve structure generally has reduced sidewall surfaces to reduce shadowing of e-beams during sterilization to permit a more effective active sterilization of the valve. FIG. 42 depicts a partial cross-sectional view of the filler valve 120. The filler valve 120 is provided with a cap mechanism 121 for use in conjunction with a CIP procedure. FIG. 42 also shows the valve 120 having a cap on its distal end used in a clean in place procedure for cleaning the valves prior to operation.

Filler Wheel Sterilization

Figure 17:
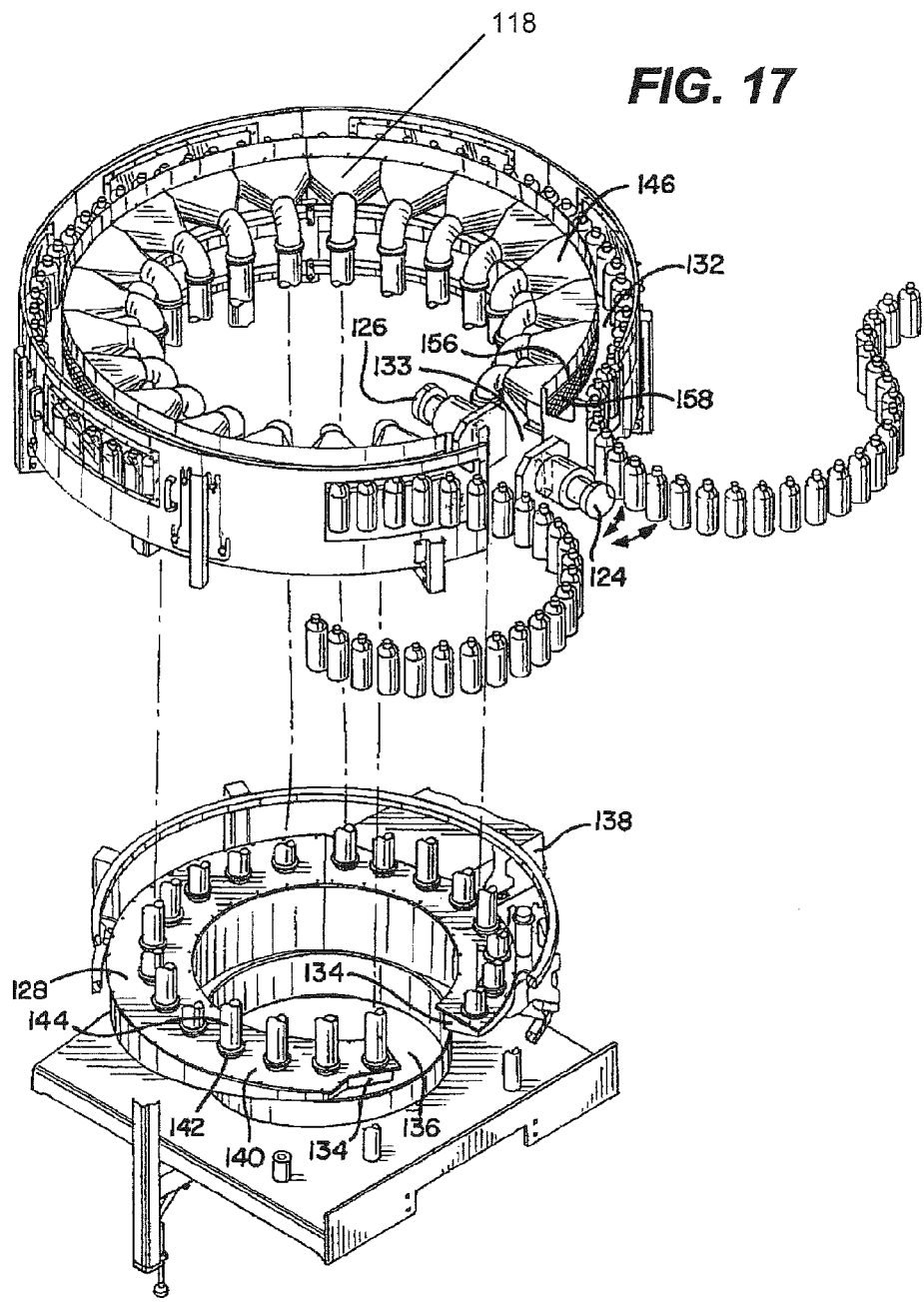
FIG. 17 is an partial exploded view of the filler assembly.
Figure 18:
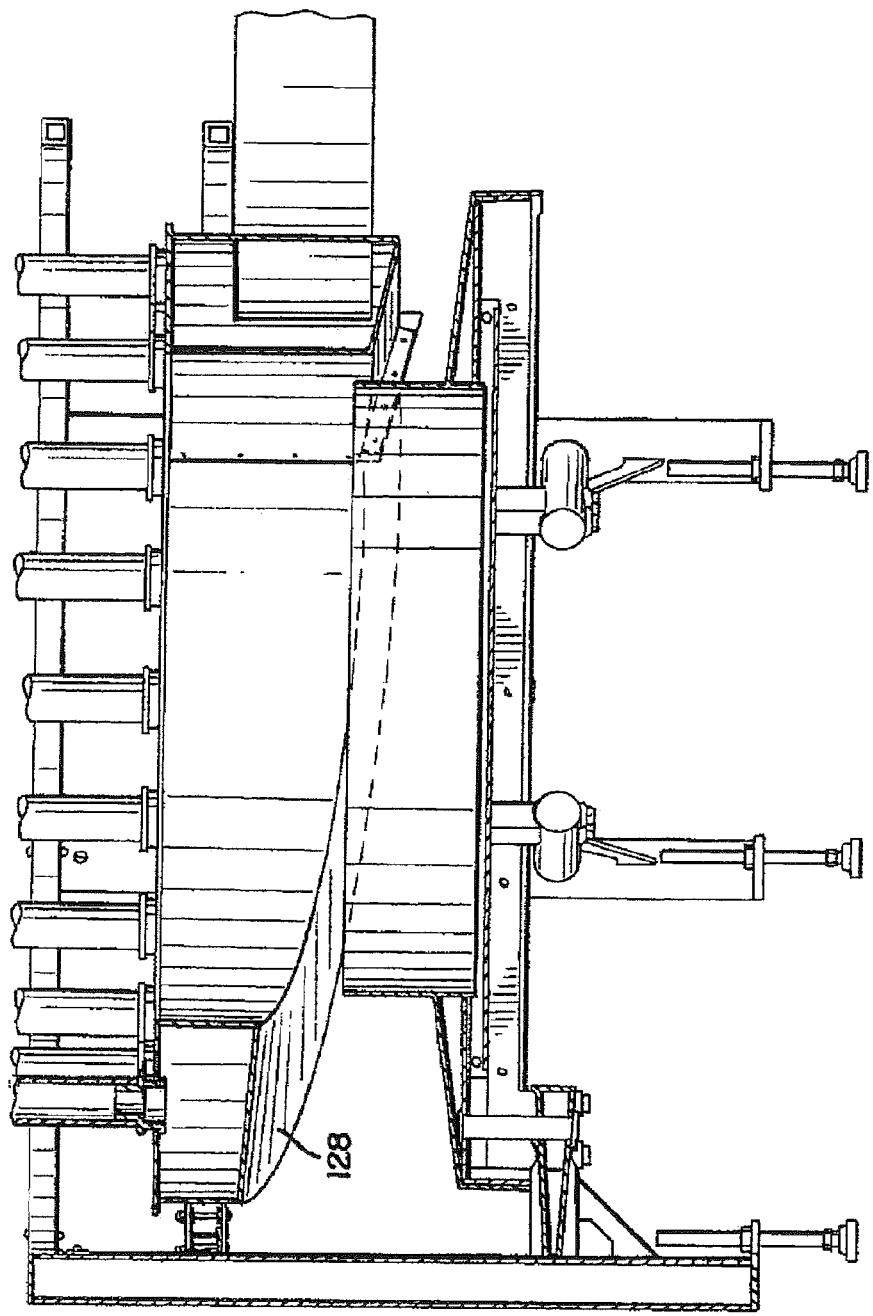
FIG. 18 is partial elevation view of an inlet manifold of an air management system of the filler wheel.
Figure 19:
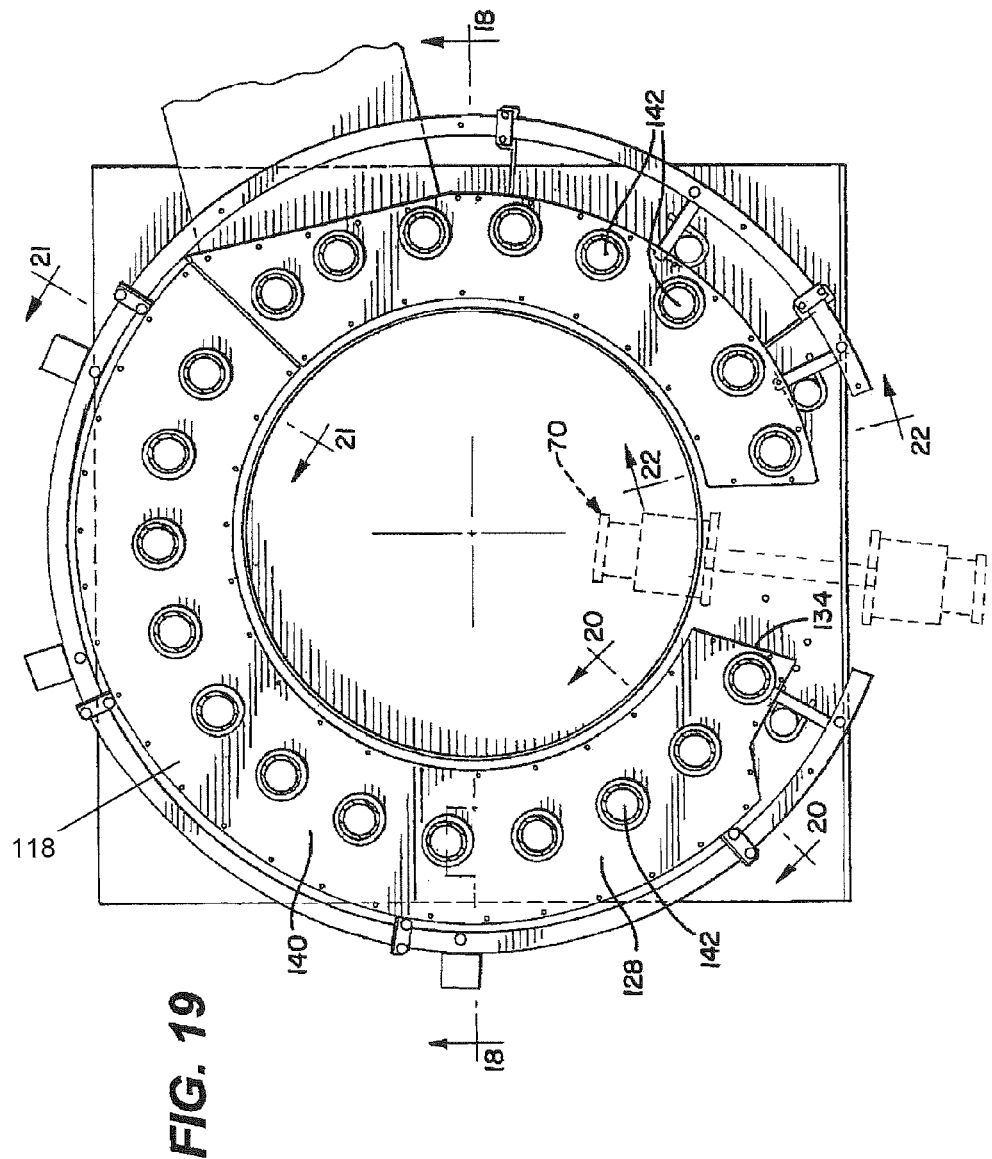
FIG. 19 is a plan view of the inlet manifold of FIG. 18.
Figure 22:
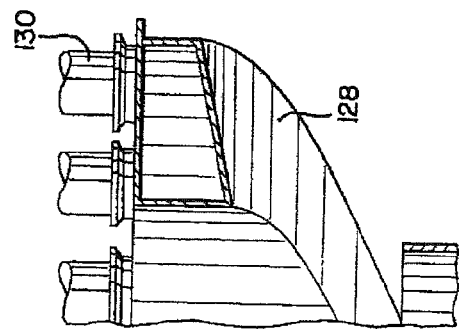
FIGS. 20-22 are partial cross-sectional views of the inlet manifold.
Figure 21:
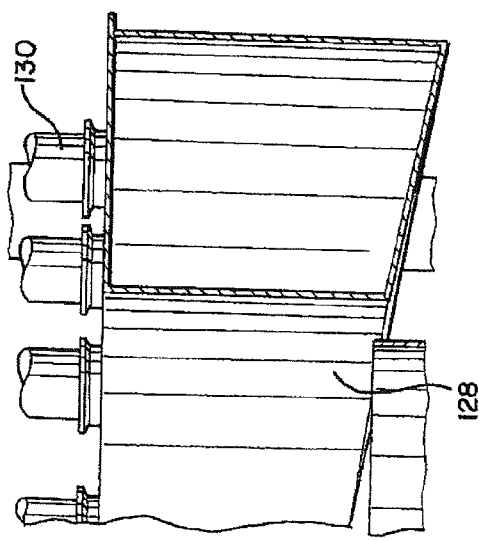
Figure 20:
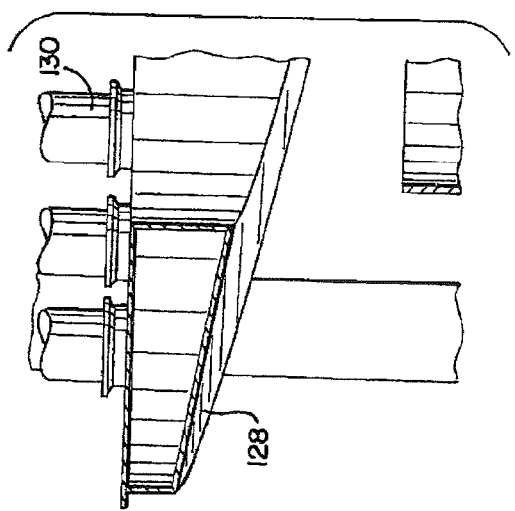
Figure 23:
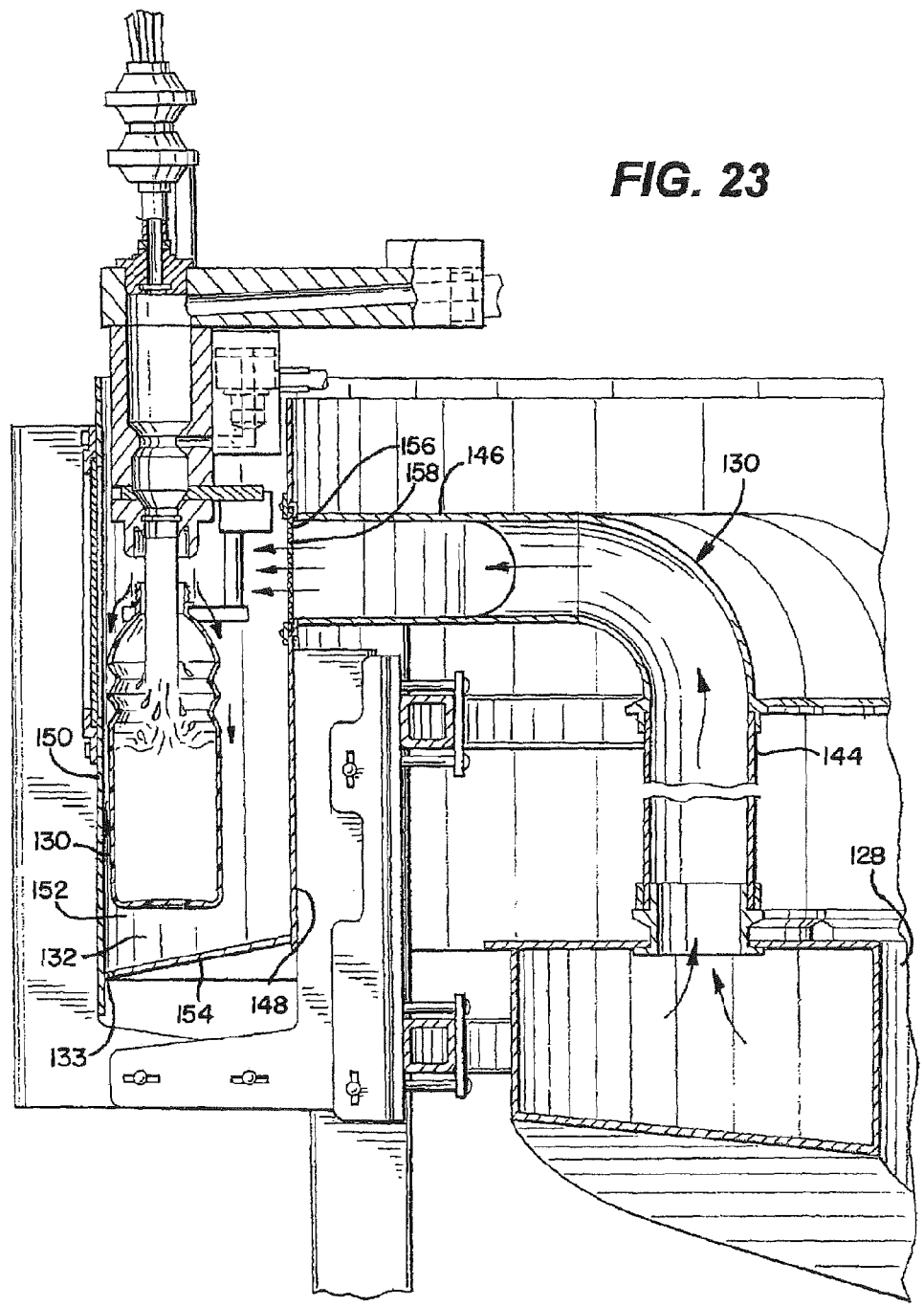
FIG. 23 is a partial cross-sectional view of the filler assembly and showing an air flow path of the filler wheel air management system.

The filler wheel sterilization unit 70 generally includes a first filler wheel e-beam emitter 124 and a second filler wheel e-beam emitter 126. The e-beam emitters 124, 126 provide sterilization during operation of the filler wheel and provide an active sterilization zone. The filler wheel e-beam emitters 124, 126 are positioned proximate the filler wheel 47 between container inlet portion 49 and container outlet portion 51 and within an opening associated with the filler wheel air management system 118 to be described. The e-beam emitters 124,126 are mounted on yokes that are fully-articulating along multiple axes as indicated in FIG. 17. The e-beam emitters 124, 126 are positioned proximate a lower portion of the filler assembly 46 and are directed upwards towards the filler grippers 122, such that they are directed at an underside surface of the filler grippers 122 and filler valves 120. The e-beam emitters 124, 126 emit an electron field and in one exemplary embodiment, the respective electron fields overlap one another as shown in FIG. 15a. As will be described in greater detail below, as the filler wheel 47 rotates, the filler valves 120 and the grippers 122 pass through electron fields to sterilize the valves 120 and grippers 122.

As can be appreciated from FIGS. 10 and 15-17, before the containers C are placed on the filler wheel 47, the filler wheel e-beam emitters 124, 126 sterilize the filler grippers 122 prior to receiving the containers C. In addition, the filler wheel e-beam emitters 124, 126 are positioned such that they also sterilize the filler valves 120 just before the filler valve heads provide product to the containers. Because of the degree of impingement at which the filler wheel e-beam emitters 124, 126 are positioned, the filler valves pass through the electron beam field simultaneously with the grippers 122. This allows the electron beam field to contact each of the filler valves 120, filler valve heads, and grippers. Any microorganisms, therefore, that might be present on the filler valve heads and the grippers are killed, and both will remain sterile. The electron beam zone produced by the filler wheel e-beam emitters 124, 126 fully encompass the heads of the filler valves 120 to sterilize all sides prior to filling. By sterilizing the filler valve heads just before each filling event, it is guaranteed that any microorganisms present on the filler valve head are not transferred to the product. By way of example, in a filler wheel 47 having an approximate seventy-six (76) inch diameter and supporting sixty (60) filler valves, each valve 120 and gripper 122 can be dosed once every six (6) seconds by the filler wheel e-beam emitters 124, 126 in order to accomplish sufficient sterilization. Once the containers C are filled, the containers C are passed off to the transfer mechanism 54 to be described.

Filler Wheel Air System

In an exemplary embodiment, as shown in FIGS. 16-23, the filler wheel 47 is provided with the localized filler wheel air management system 118. The filler wheel air management system 118 generally includes an inlet manifold 128, an intermediate supply section 130 and a generally annular channel 132. As described in greater detail below, the air management system 118 provides a conduit for a supply of air proximate an opening of the container C as the container C is being filled with product by the filler wheel 47.

As shown in FIGS. 17-22, the inlet manifold 128 has a generally curved configuration and may be considered to be horseshoe shaped. As such, the inlet manifold has a pair of ends 134 defining a gap 136 therebetween. The inlet manifold 128 has an opening at an intermediate section that is in communication with an inlet duct 138 that delivers a supply of HEPA filtered air to be described in greater detail below. As further shown in FIGS. 17, 18 and 20-22, the inlet manifold 128 is tapered towards the ends 134 and thus the manifold 128 has a greater volume at locations between the ends 134. The tapered ends assist in keeping air velocities constant in the inlet manifold 128. The inlet manifold has a top surface 140 having a plurality of openings 142. The intermediate supply section 130 has a vertical member 144 having one end connected to the opening 142 and another curved end having a diverging outlet section 146 defining an increased outlet area. It is appreciated that the diverging outlet section 146 will direct a supply of filtered air in a generally horizontal direction.

The annular channel 132 is generally mounted around the filler wheel 47. It is understood that the annular channel 132 has a gap 133 generally defining wherein the containers C enter and exit the annular channel 132. The annular channel 132 has an inner annular wall 148 and an outer annular wall 150. The inner annular wall 148 is spaced from the outer annular wall 150 to define a pathway 152 therebetween. The annular channel 132 further has an annular bottom wall 154. The inner annular wall 148 has an opening 156 wherein the inner annular wall is mounted on the filler wheel 47 wherein the outlet section 146 is aligned with the opening 156 in the inner annular wall 148. As further shown in FIGS. 17 and 23, the inner annular wall 148 has a screen 158 positioned over the opening 156. Any mesh screen or structure that provides a uniform pattern and distribution of air is suitable for covering the opening 156. Moreover, the desired airflow may be accomplished without any structure covering the opening all together. The outer annular wall 150 may be in the form of a plurality of removable segments 160. The removable segments 160 may have windows such that operators can view the containers C in the pathway 152.

As further shown in FIG. 17, it is understood that the intermediate supply section 130 comprises a plurality of supply sections 130. Accordingly, a plurality of vertical members 144 extends upwards from respective openings 142 in the inlet manifold 128. Each diverging outlet section 146 is positioned adjacent one another around the filler wheel 47 wherein the outlets 146 collectively are in communication with the opening 156 in the inner annular wall 148. Smooth connections between adjacent outlet sections 146 assist in maintaining smooth air flow. As will be described in greater detail below, the components of the filler wheel air management system 118 collectively define a conduit for the delivery of filtered air proximate an opening of the containers C as the containers C are being filled by the filler valves 120.

Transfer Mechanism

Figure 25:
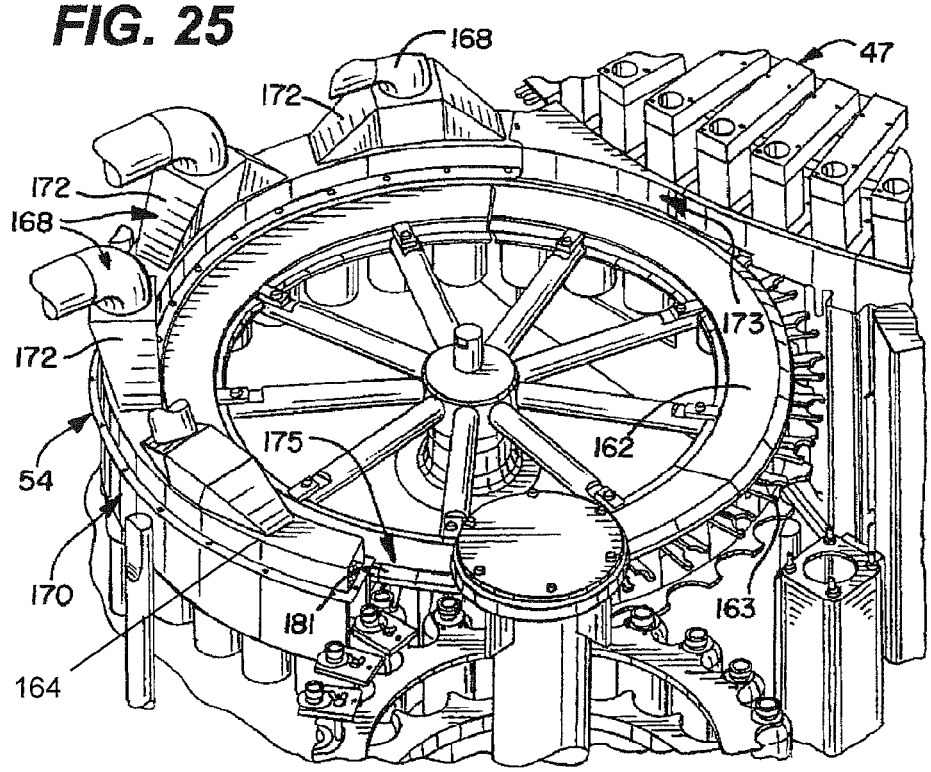
FIG. 25 is a partial perspective view of a transfer mechanism of the second module.
Figure 26:
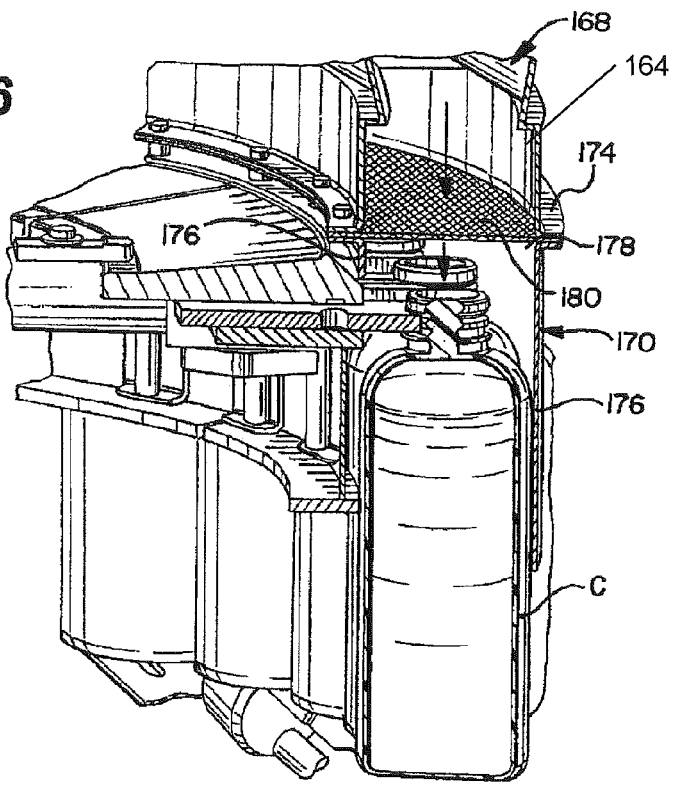
FIG. 26 is a partial cross-sectional view showing air flow of a transfer mechanism air management system.

As shown in FIGS. 25 and 26, the transfer mechanism 54 transfers containers C filled with product from the filler assembly 46 to the capper assembly 48. The transfer mechanism 54 generally includes a transfer wheel 162, the transfer mechanism e-beam sterilization unit 72 and a transfer mechanism air management/isolation system 164.

The transfer wheel 162 is a generally circular structure and has supporting systems for rotation. The transfer wheel 162 has a plurality of grippers 163, a container inlet portion 181 and a container outlet portion 183. The transfer wheel 162 is generally positioned adjacent to the filler assembly 46 such that it can receive filled containers C from the filler assembly 46. However, any suitable transfer mechanism can be used for transferring the filled containers from the filler assembly 46 to the capper assembly 48. For example, a mechanism could be used that transfers containers C from the filler assembly 46 in a linear fashion if desired.

Transfer Wheel Sterilization Unit

In an exemplary embodiment, the transfer mechanism e-beam sterilization unit 72 generally includes a single transfer e-beam emitter 166 positioned adjacent to the transfer wheel 162 between the container inlet portion 181 and the container outlet portion 183 and directed towards the wheel 162. It is understood that additional e-beam emitters could also be utilized with the unit 72. After the containers C have been filled with beverage product, the containers C are transferred to the capper assembly to be sealed with a closure. It is necessary to sterilize the grippers 163 holding a filled, open container C, and the travel zone just above the containers, so that contamination is not introduced onto the container mouth or into the product. Thus, as shown in FIGS. 10 and 11, before receiving the container C from the filler wheel 47, the e-beam field produced by the transfer wheel e-beam emitter 166 sterilizes the grippers 163 located on the transfer wheel 162. In one embodiment, the transfer wheel 162 has a diameter of approximately forty (40) inches. At 600 bpm, therefore, each gripper 163 is dosed by the transfer wheel e-beam emitter 166 approximately once every 2.8 seconds. After sterilization, the grippers 163 on the transfer wheel 162 receive the containers C from the filler assembly 46, and transfer the containers C to the capper assembly 48 to place a cap 202 on each filled container C.

Transfer Mechanism Air Management System

In an exemplary embodiment shown in FIGS. 25 and 26, the transfer wheel 162 is provided with the local air management system 164. The transfer mechanism air management system generally includes an inlet duct 168 and an outlet manifold 170.

The inlet duct 168 generally includes an air line having one end connected to a supply of ULPA/HEPA filtered air. The duct 168 has a diverging outlet end 172 having an increased outlet area. In an exemplary embodiment, the inlet duct 168 comprises a plurality of spaced ducts 168, each having a diverging outlet end 172. The inlet ducts 168 may all be connected to the common filtered air source.

The outlet manifold 170 generally has a top wall 174 and a pair of depending walls 176. The outlet manifold 170 generally has a U-shaped cross section. The top wall 174 has an opening 178 that correspond and are in communication with the diverging outlet ends 172 of the inlet ducts 168. As shown in FIG. 26, a screen 180 is positioned against an underside surface of the top wall 174 and over the openings 178. Again any mesh screen or structure that provides a uniform pattern and distribution of air is suitable for covering the openings 178. Also as stated above with respect to the filler assembly, the desired airflow may be accomplished without any structure covering the openings all together. The outlet manifold 170 has a curved configuration and has a length that covers a portion of the transfer wheel 162. In one exemplary embodiment, the outlet manifold 170 has an inlet end 173 positioned proximate the filler assembly 46 and an outlet end 175 positioned proximate the capper assembly 48. As will be described in greater detail below, the components of the transfer mechanism air management system 164 provides a conduit that delivers filtered air in a downward direction towards the top of the open containers C.

Capper Assembly

Figure 28:
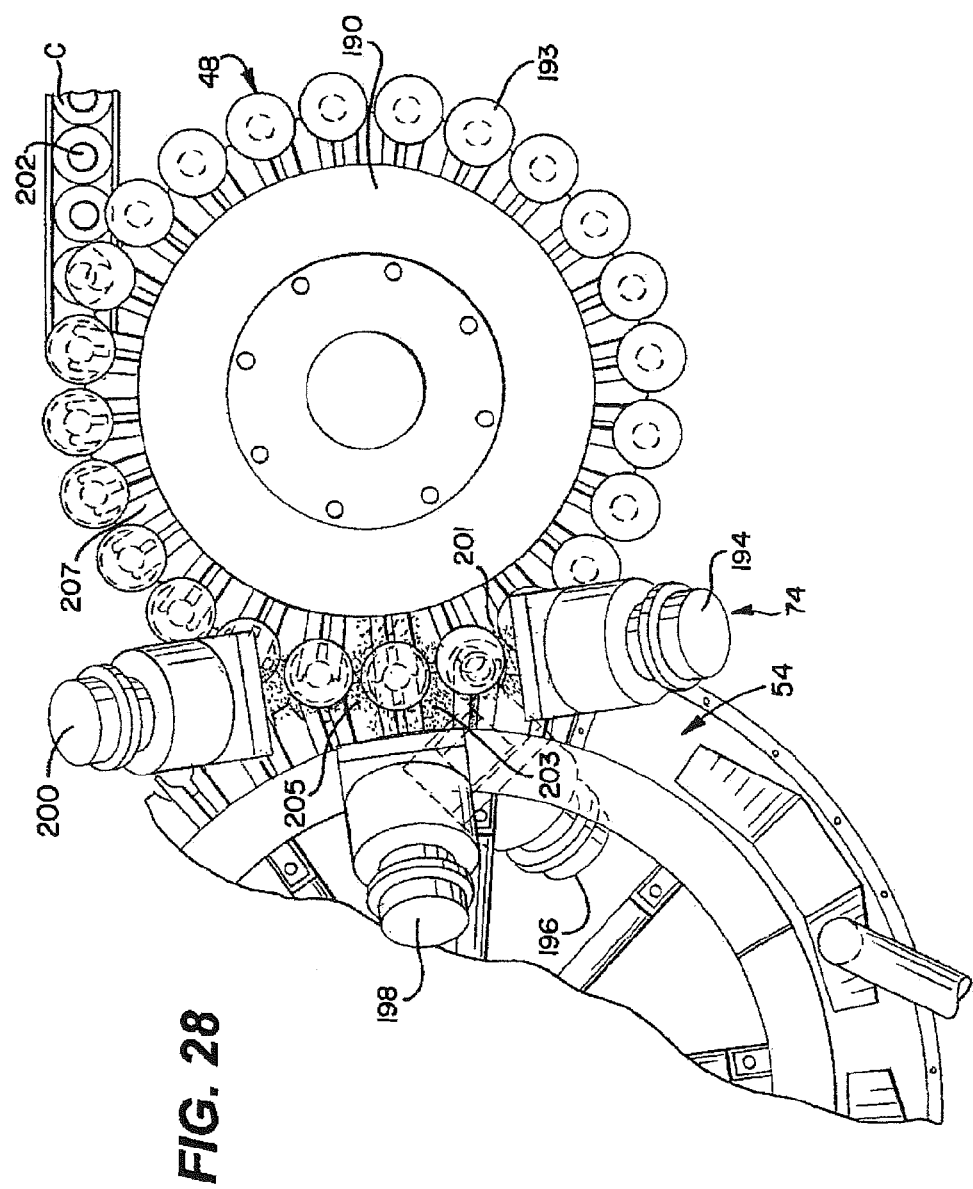
FIG. 28 is a partial plan view showing a capper assembly of the second module.
Figure 29:
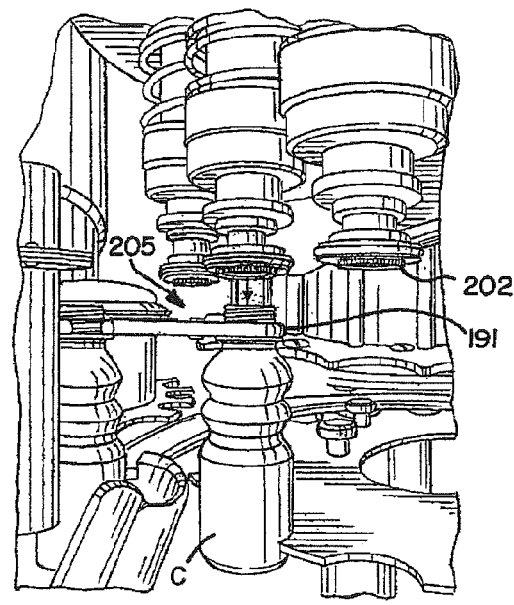
FIG. 29 is another view of the capper assembly of the second module.
Figure 35:
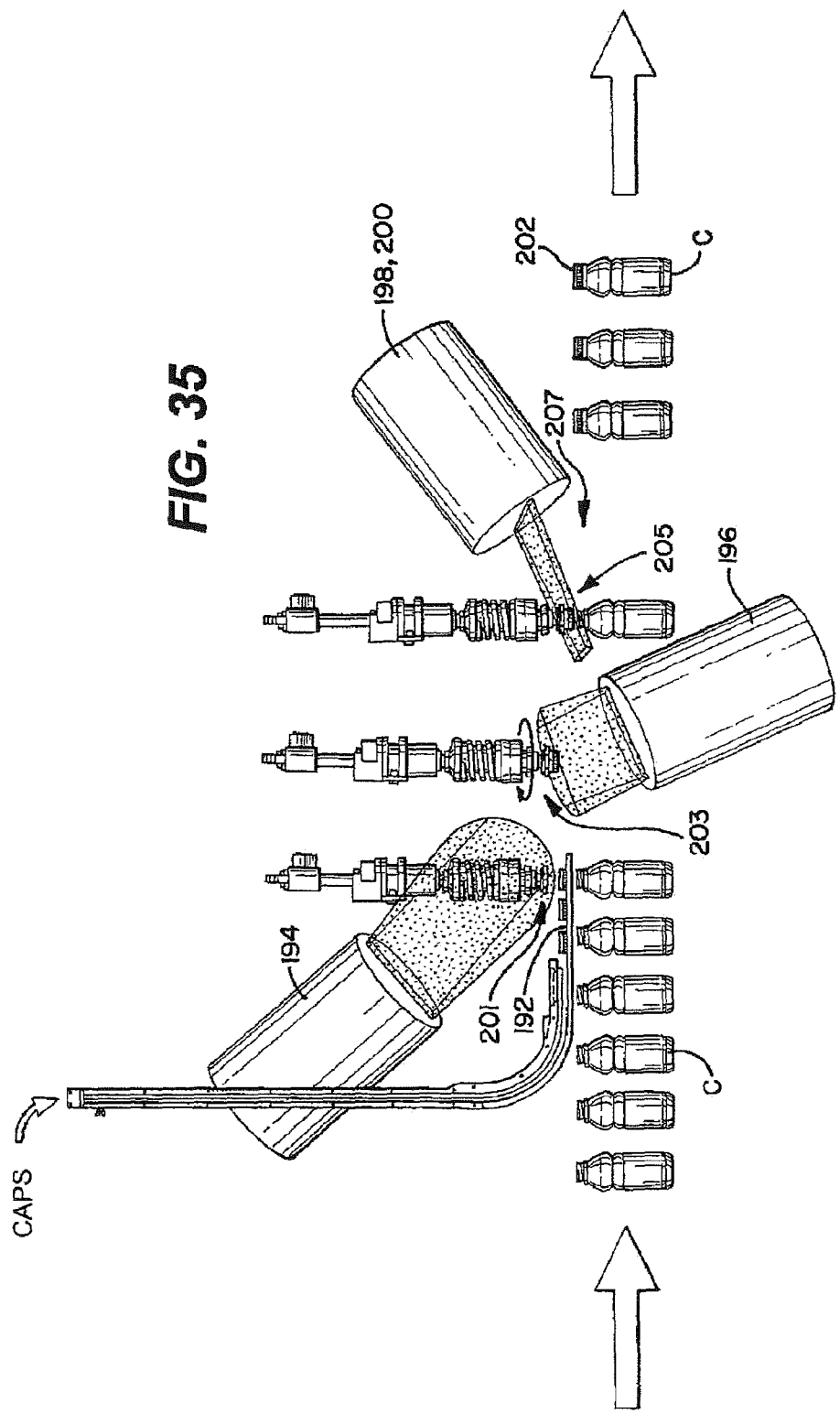
FIG. 35 is a schematic view of e-beam emitters associated with the capper assembly.

As shown in FIG. 29, the capper assembly 48 places a cap on a respective filled container C received from the transfer mechanism 54. This is done while maintaining a sterile environment. As shown in FIGS. 28, 29, and 35, the capper assembly 48 generally includes a capper wheel 190, the capper wheel sterilization unit 74, and a cap loader 192.

The capper wheel 190 is a generally circular structure and has supporting systems for rotation. The capper wheel 190 has a plurality of grippers 191 as well as a plurality of cap chucks 193 designed to receive a cap to be described. The grippers 191 receive the filled containers from the transfer wheel 162. The cap chucks 193 have associated structure to hold caps therein as well as for rotational movement. The capper wheel 190 is generally positioned adjacent to the transfer mechanism 54 and discharges filled and capped containers C for further packaging.

The capper wheel sterilization unit 74 includes a plurality of e-beam emitters, namely: a first cap e-beam emitter 194, a second cap e-beam emitter 196, a third cap e-beam emitter 198 and a fourth cap e-beam emitter 200. The first cap e-beam emitter 194 and the second cap e-beam emitter are positioned generally adjacent one another at a location adjacent the capper wheel 190 where caps are initially installed onto a respective cap chuck 193. The electron fields produced by the emitters 194, 196 may overlap and in conjunction with the rotation of the cap chuck 193, it is assured that all surfaces of the cap will be sufficiently sterilized. The third cap e-beam emitter 198 and the fourth cap e-beam emitter are positioned adjacent a further rotational path of the capper wheel 190 to provide a sterile field that is occupied by the filled container C while a cap is screwed onto the container C, to be described further.

Cap Loader

The cap loader 192 has a slotted plate have structure for rotation of the plate. The slot is dimensioned to receive a cap. A cap chute can be provided to deliver caps to each slot in the plate. As is known, the cap chuck 193 is moved by the capper wheel 190 in operable cooperation with the cap loader 192 wherein a cap is loaded in the cap chuck 193.

Environment Control System

Figure 36:
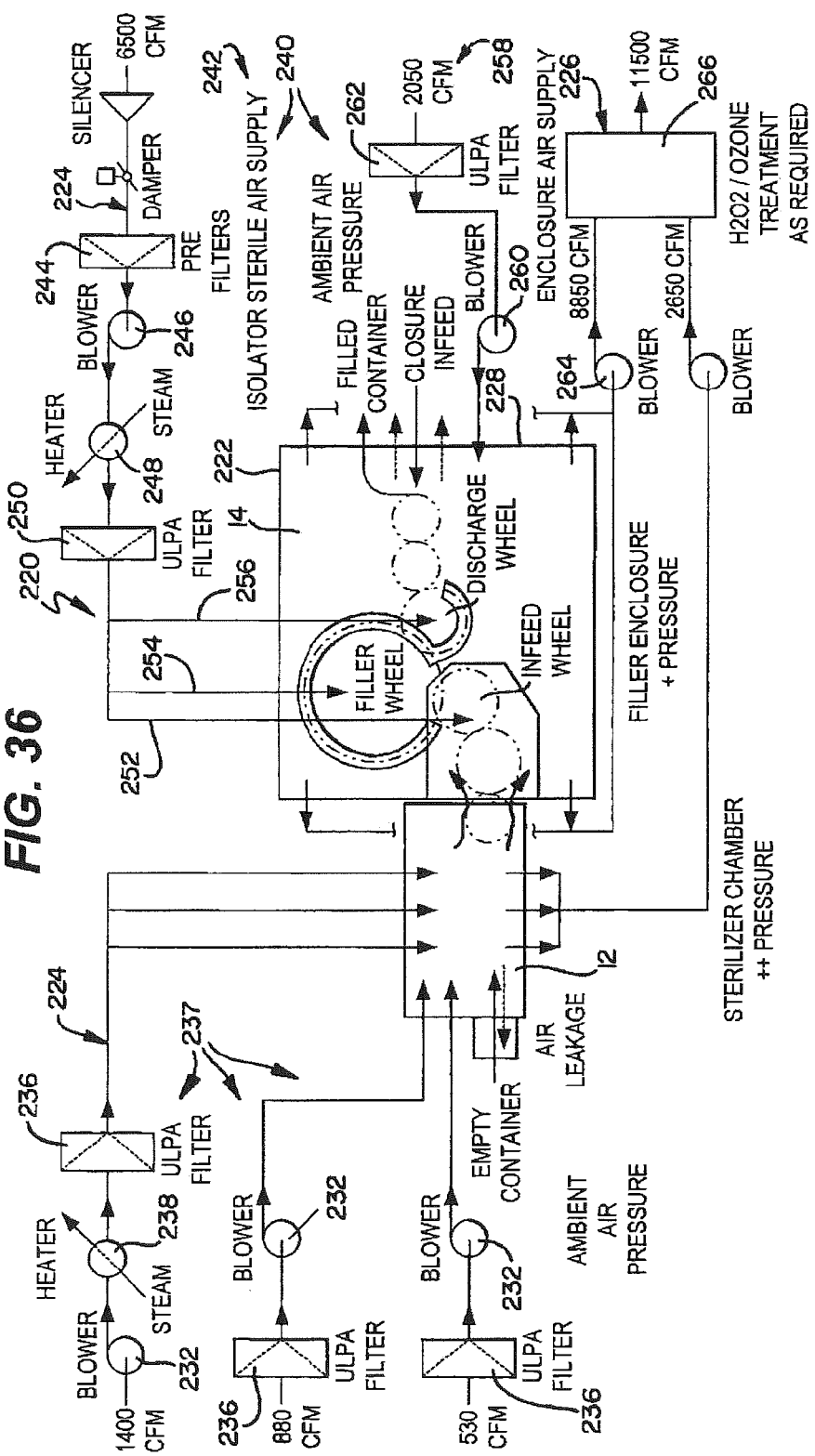
FIG. 36 is a schematic view of an environment control system associated with the first module and second module of the system of the present invention.

As shown in FIG. 36, the system 10 further includes an overall environment control system 220. The system 220 assists with the air management systems discussed above as well as providing additional systems and structures to aid in filling and capping the containers C in an active sterilization zone in the CHE 18. The environment control system generally includes a housing enclosure 222, a filtered air delivery system 224 and an H2O2/Ozone treatment system 226.

The housing enclosure 222 generally encloses the components of the second module 14. As shown in FIGS. 10, 11, 11a, and 36, the housing enclosure 222 has a plurality of walls and barriers 228 positioned around the components of the second module 14. Access doors 230 may be provided for operators or other personnel to gain access to the second module 14. The walls and barriers include x-ray and irradiation shielding such as stainless steel wrapped lead panels reinforced with plywood to prevent operator exposure to the electron beams. In addition, windows (not shown) composed of leaded glass allow the operators to visually inspect operation of the second module. In one exemplary embodiment, the housing enclosure 222 may also be considered a part of the CHE. This structure may be formed such that it may be considered at Class 1000-10,000 enclosure.

The filtered air delivery system 224 comprises a plurality of filtered air sources that direct air to various parts of the system. As further shown in FIG. 36, a first set 232 of filtered air delivery systems 224 is provided to deliver filtered air to the container sterilizer 32. Each system 232 has a blower and ULPA/HEPA filter 236. One of the systems in this set may also include a heated steam source 238. These systems provide ULPA or HEPA filtered air to the container sterilizer 32 thereby maintaining a positive pressure in the sterilizer 32. This air can be vented from the sterilizer 32. A second set 240 of filtered air delivery systems is provided to deliver filtered air to certain components of the second module 14. An isolation sterile air supply system 242 is provided and has a pre-filter 244, a blower 246, a heated steam source 248 and a ULPA/HEPA filter 250. The isolation sterile air supply system 242 has a first output 252, a second output 254 and a third output 256. The first output 252 is connected to the top member opening 110 (FIGS. 11 and 11a) of the isolator 52. The second output 254 is connected to the filler wheel air management system 118. The third output 256 is delivered to the transfer wheel air management system 164. An enclosure air supply system 258 has a blower 260 and a ULPA/HEPA filter 262 to provide filtered air and positive pressure to the housing enclosure 222.

Finally, as further shown in FIG. 36, the H2O2 treatment system 226 has associated blowers 264 and an H2O2 module 266. However, any suitable form of chemical treatment can be used that can remove ozone from the second module. The treatment system 226 is operably connected to both the container sterilizer 32 and the housing enclosure 222. The second module 14 is vented to remove any ozone caused by the emitters, and the air is treated prior to release into the atmosphere.

Overall Operation of the System 10

Overall operation of the system 10 will now be described. It is understood by those skilled in the art that the system 10 has the necessary power sources and associated controllers to effect and control operation of the system 10 as known by those skilled in the art. The components of the first module 12 and the second module 14 are initially set-up wherein the system 10 is ready to receive containers for filling and capping. Moreover, before operation, the system 10 is pre-sterilized using chemicals such as hydrogen peroxide and further in conjunction with the e-beam emitters. Other pre-sterilization techniques could also be used. Thus, prior to operation of the system 10, the system 10 is sterilized to eliminate any contaminants or microbes etc. As will be described below, the structures of the system 10 provide various active sterilization zones and confined hygienic environments during operation of the system 10 as containers C proceed through a path of travel through the system 10.

Operation of the First Module

Figure 32:
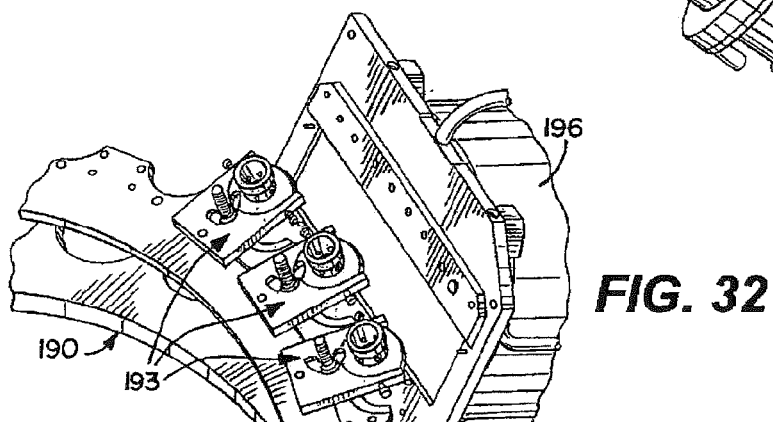
Figure 33:
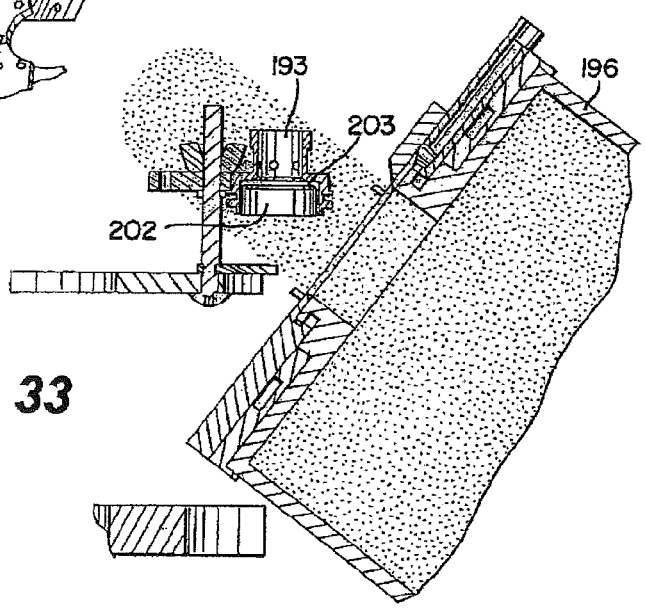
FIG. 33 is a partial cross-sectional view showing the capper assembly of the second module.
Figure 34:
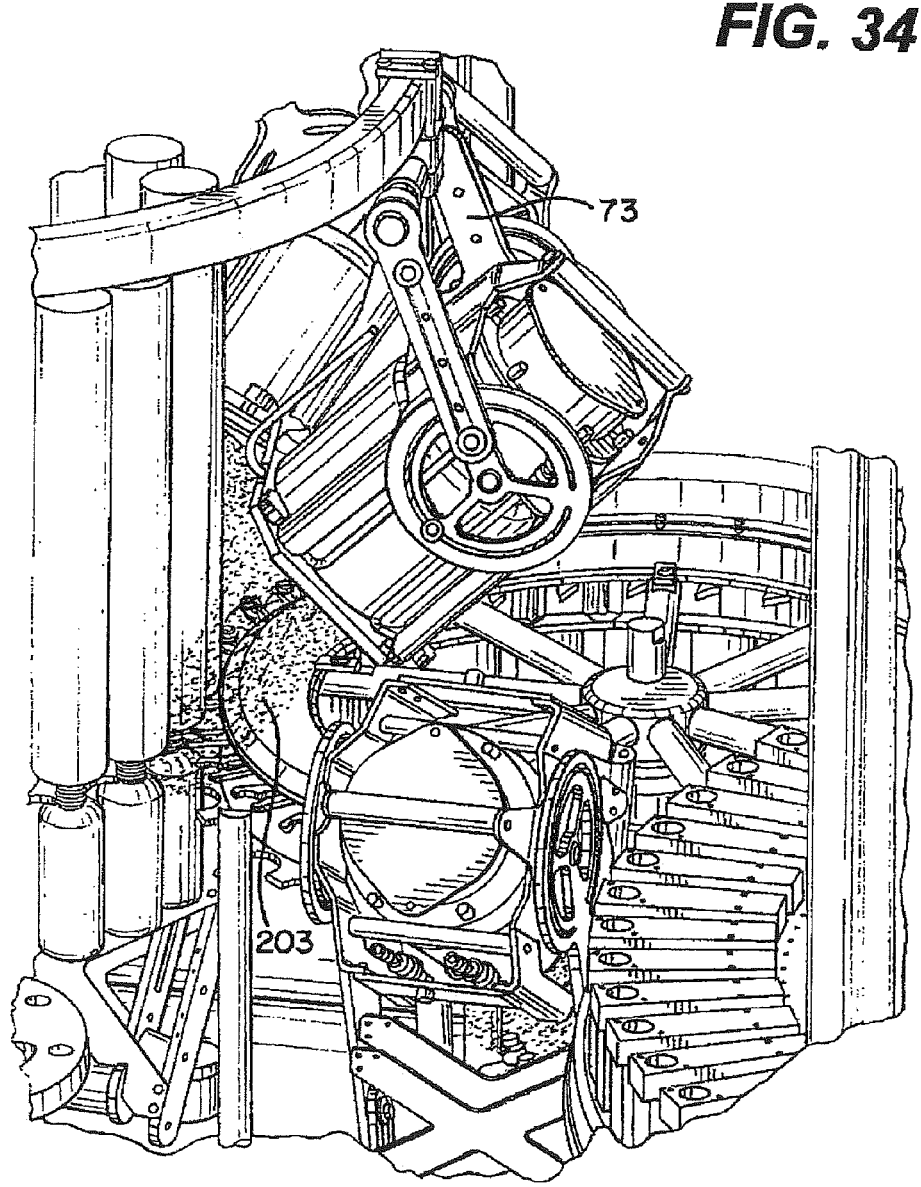
FIG. 34 is another partial perspective view of the capper assembly of the second module.

As can be appreciated from FIGS. 4 and 5, empty containers C, typically in the form of plastic beverage containers are removed from pallets and loaded onto the conveyor 20 by the de-palletizer 22. The conveyor 20 delivers the containers C to the waterless rinser 30 wherein clean, compressed air is delivered to the containers C wherein the containers C are thoroughly rinsed and any contaminants are vacuumed away. The conveyor 20 delivers the containers C to the container sterilizer 32. The container sterilizer 32 may also include ULPA/HEPA filtered air treatment as well as H2O2 treatment on the container C. The high-energy e-beam emitters of the container sterilizer 32 produce an electron field that encompasses the pathway taken by the containers C. As discussed, the container sterilizer 32 may have suitable structure to invert the containers C to assure that all surfaces of the containers 32 are sterilized. As such, once the containers C reach the outlet wheel of the container sterilizer 32, the containers C are in a clean, sterile state. As previously discussed, the container sterilizer 32 utilizes high-energy e-beam emitters in one exemplary embodiment. Other forms of container sterilization could also be used in the first module 12 as desired. The ultimate result of the first module 12 is the delivery of sterile containers C to the second module 12 as shown in FIG. 32.

Operation of the Second Module

As discussed above, before operation of the second module 14, the second module 14 is sterilized using a chemicals and e-beam treatment. Certain components of the system may include built-in systems for such cleaning such as the inlet manifold of the filler wheel air management system. Structures may also be provided to inject cleaning liquids such as water and/or hydrogen peroxide through screens in the air management systems.

Figure 37:
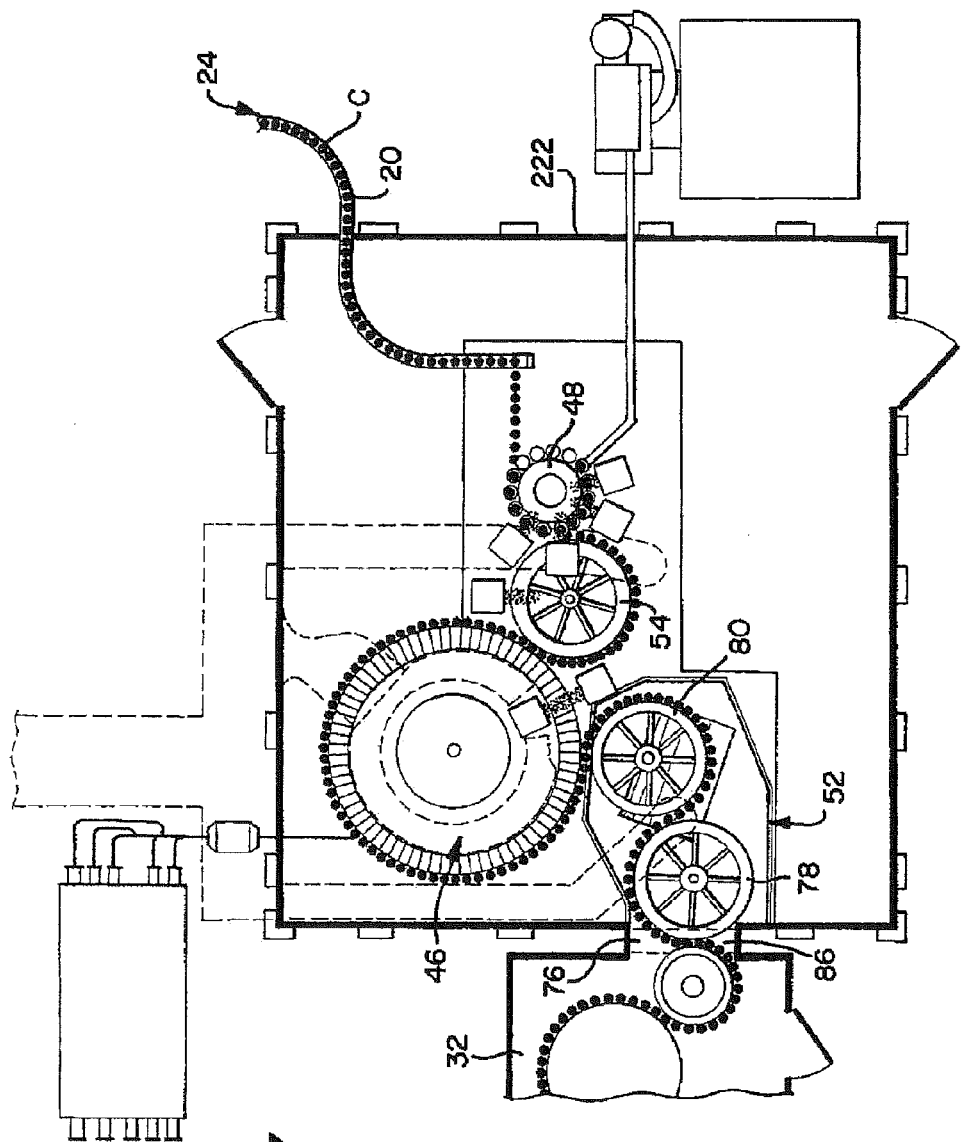
FIGS. 37-40 are schematic plan views of the second module showing operation of the second module.

As further shown in FIG. 37, the containers C are delivered from the first module 12 to the second module 14 at the interface area 86 generally defined by the air lock structure 76 of the isolator assembly 52. Any access windows and doors of the isolator assembly 52 are closed. As is appreciated from FIGS. 11, 11a, and 36, ULPA/HEPA filtered air is delivered to the isolator assembly by the isolation sterile air supply system 242 to maintain a positive air pressure in the isolator assembly 52. As the air lock structure 76 has the open bottom end 94, the supplied air may pass downwards through the open bottom end 94. The supplied air may then pass into the housing enclosure 222 and can be vented as desired as it is understood that the housing enclosure 222 is vented. In sum, positive air pressure is maintained as well as downward air flow to assist in assuring any potential microbes are directed away from the containers C, including the openings of the containers C. The containers C are passed from the outlet wheel of the first module 12 and to the first intake wheel 78 via the grippers 79. The first intake wheel 78 passes the containers C to the second intake wheel 80 via the grippers 81. It is understood that the grippers 79, 81 as well as the environment of the isolator assembly 52 are all in sterile conditions. The second intake wheel 80 then delivers the sterile containers C to the filler assembly 46 through the container outlet opening 106. The ULPA/HEPA air is constantly circulated by the intake wheels 78, 80 and grippers 79, 81 and maintaining sterile conditions. The isolator assembly 52 may be considered passive sterilization is the assembly 52 is initially sterilized and then wherein the air flow assists in maintaining the sterile conditions.

As previously discussed, the container reject mechanism 101 senses the containers C proximate the second intake wheel 80 and determines whether any container C has been damaged during the sterilization process in the first module 12. This can happen, for example, such as if the sterilization process in the sterilizer 32 deformed a wall of the container C making the container C unsuitable for filling and capping. In such case, the container reject mechanism senses the deformed container C and ejects the container C from the grippers 81 and the rejected container C falls to the floor 96 of the isolator assembly 52. In this fashion, the grippers 81 receive a signal to open wherein the grippers 81 drop the container C. The slanted portion 112 of the floor 96 directs the container C to the access door 114. The air cylinder 116 can be actuated to open the access door 114 wherein the rejected containers C can be removed from the isolator assembly 52 and discarded (FIG. 12). It is understood that the system 10 is designed such that if a container C is rejected and leads to a filler valve/gripper on the filler wheel 47 not being loaded with a container C, the filler valve will not be actuated to deliver liquid product etc. As previously discussed, depending on the sizing of the outlet wheel of the first module 12 and the intake wheel of the second module 14, only a single intake wheel in the isolator assembly 52 could be employed.

Figure 38:
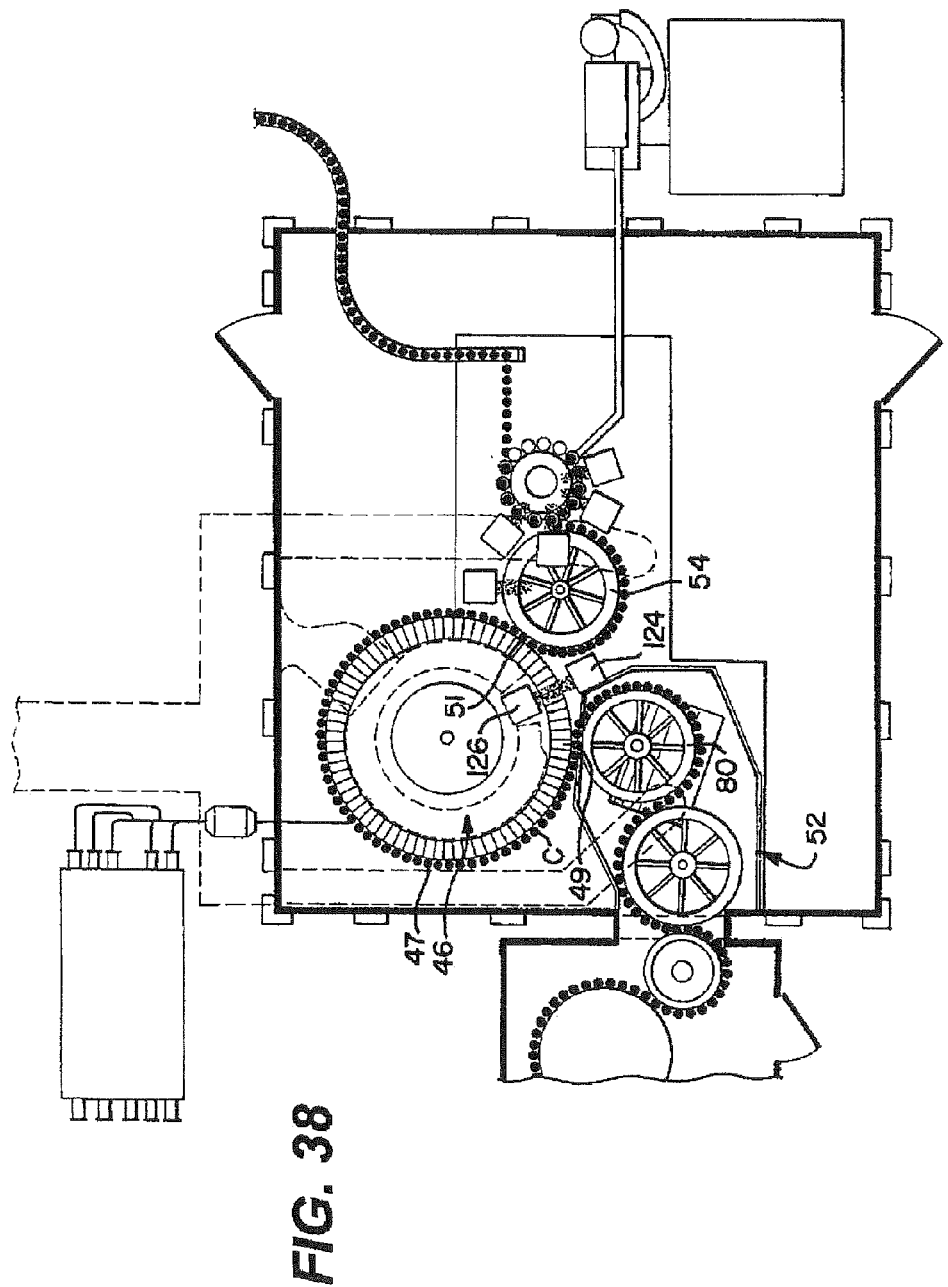

As further shown in FIG. 38, the filler wheel 47 receives the containers C from the second intake wheel 80 at the container inlet portion 49. As such, the grippers 122 on the filler wheel 47 grip the containers C from the grippers 81 on the second intake wheel 80. The containers C are thus positioned below an associated filler valve 120, and the containers C, grippers 81, and filler valves 120 travel in an arcuate path as the filler wheel 47 rotates. Just prior to the transfer from the second intake wheel 80 to the filler wheel 47, the grippers 122 on the filler wheel 47 are sterilized. To this end, the first filler e-beam emitter 124 and the second filler e-beam emitter 126 provide electron fields that overlap one another. (See e.g., FIG. 15a). The electron field is large enough such that the field encompasses the path traveled by the grippers 122 and filler valves 120 of the filler wheel 47. As shown in FIG. 38, it is understood that the e-beam emitters 124, 126 are positioned such that the grippers 122 are sterilized just prior to receiving the sterile containers C from the second intake wheel 80. Moreover, to accomplish this, the e-beam emitters 124, 126 are positioned between the container inlet portion 49 and the container outlet portion 51. The grippers 122 and valves 120 are sterilized as these components will contact the containers C. Thus, sterile conditions continue to be maintained as the grippers 122 and valves 120 are actively re-sterilized upon constant rotation of the filler wheel 47.

Figure 24:
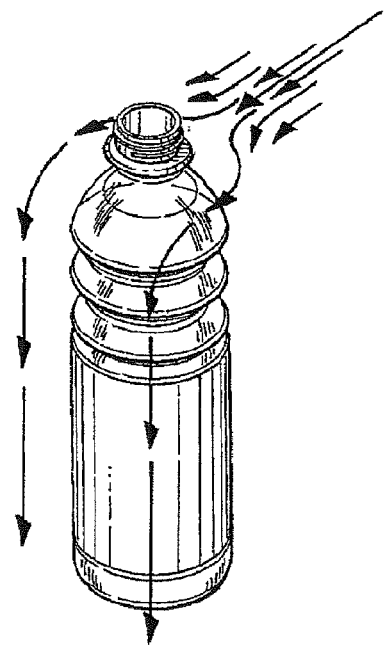
FIG. 24 is a schematic view of an air flow around a container.

Next, the beverage product is injected into the containers by the filler assembly 46. Because of the unique sterilization structures and processes used herein, the product can be delivered generally at ambient temperature and aseptic conditions. Elevated product temperatures are not required. Product is injected into the containers C as the filler wheel 47 rotates around its central axis. In particular, the filler valves 120, which are in fluid communication with the batched liquid product, are activated to begin to fill the containers C. The filler valves 120 fill the containers C as they rotate on the filler wheel 47. As previously discussed, the filler wheel air management system 118 supplies ULPA/HEPA filtered air to the filler wheel 47 during the filling process. The second output 254 (FIG. 36) of the isolation air supply system 242 provides filtered air to the inlet manifold 128 of the filler wheel air management system 118. Thus, the entire curved manifold 128 is filled. The tapered design of the manifold 128 assures a steady supply of filtered air and keeping air velocities constant. As can be appreciated from FIG. 23, the filtered air continues upwards through the intermediate supply section 130 and through the diverging outlet sections 146. The diverging outlet sections 146 assist in creating an air flow to the containers C. The air continues through screen 158 and thus, filtered air is provided into the annular channel 132. As further shown in FIG. 23, the outlet sections 146 and screens 158 are generally positioned proximate the openings of the containers C. The screen 158 provides a certain amount of resistance to the air flow to provide a nice steady air flow into the entire annular channel 132. Because of the structure of the annular channel 132 via the inner annular wall 148 and the outer annular wall 150 air flow is generally directed around the container opening and downwards along the longitudinal axis of the containers C and downwards in the annular channel 132. It is understood that certain gaps remain in the bottom portions of the annular channel 132 wherein the filtered air can escape downwards into the environment of the housing structure 222. Thus, the annular channel 132 is pressurized by the supply of filtered air. FIG. 24 generally shows the air flow about the container C as product is injected into the container. This airflow helps to isolate the container C and further minimize any chance of microbes or other unwanted materials from entering the container C. Air flow is directed generally proximate the neck portion of containers C. As depicted in FIG. 24, air flows at the neck portion, around the outer circumference of the neck portion of the container, and downwards following the path of the outer circumference of the container parallel to the container axis. Thus, positive air pressure is maintained around this portion of the container C and directed downwards away from the openings of the containers C. However, the particular airflow patterns are not critical so as long as a positive air pressure is maintained in the annular channel 132.

Accordingly, the filler grippers 122 are sterilized just prior to engaging a container C in sterile fashion and filtered air is provided about the container C to enhance and maintain sterile conditions as the container C is being filled. Once the container C rotates about the filler wheel 47, the filling process is designed to be complete. The container C can then be passed to the transfer mechanism 54 at the container outlet portion 51.

Figure 39:
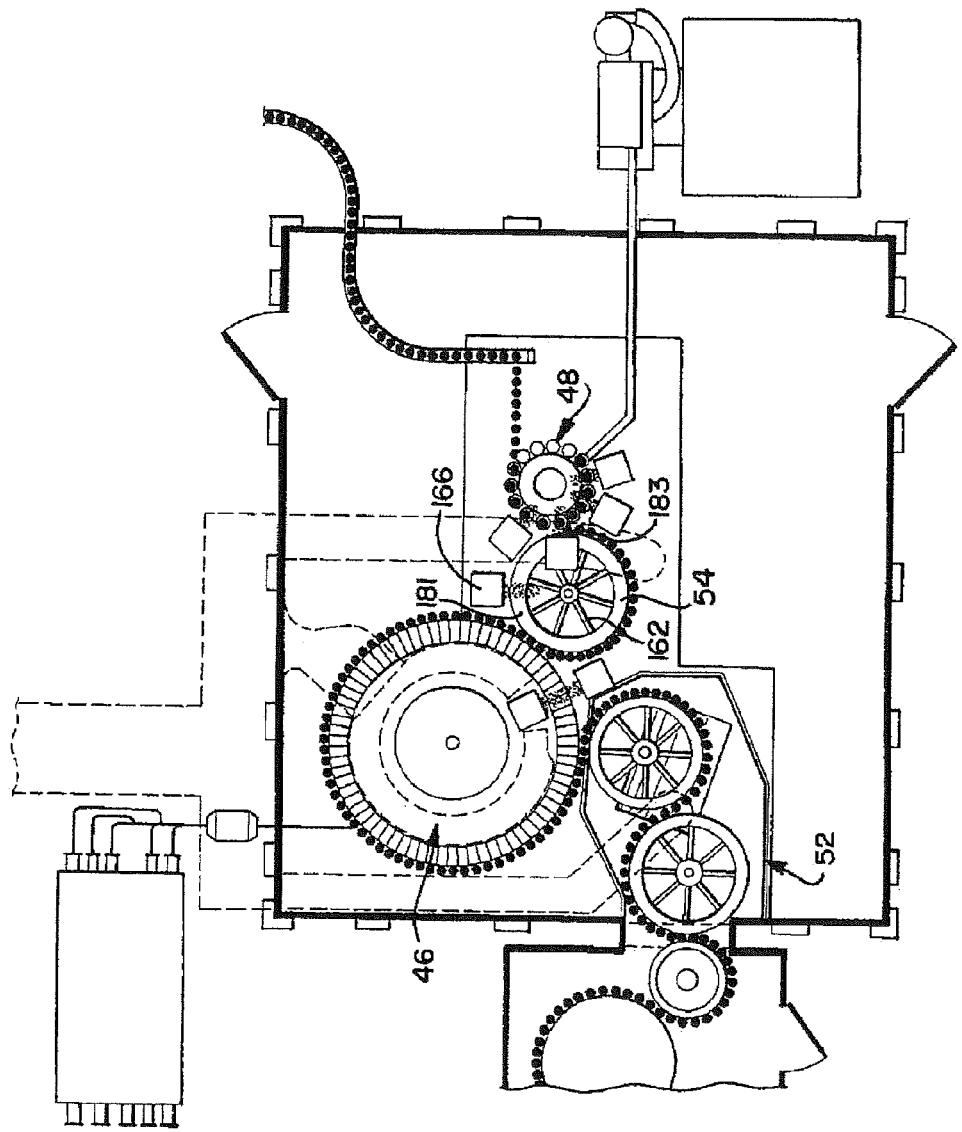

As shown in FIG. 39, the transfer mechanism 54 receives the containers C from the filler wheel 47 at the container inlet portion 181 and transfers the containers C to the capper assembly 48 at the container outlet portion 183. Prior to receiving the filled, open containers C from the filler wheel 47, the grippers 163 of the transfer wheel 162 are sterilized by the transfer wheel e-beam emitter 166 positioned between the container inlet portion 181 and the container outlet portion 183. As shown in FIGS. 11, 11a, and 39, the transfer wheel e-beam emitter 166 is positioned adjacent the transfer wheel 162 and provides a sterile electron beam field that encompasses the path that the grippers 163 occupy as the transfer wheel 162 rotates about its central axis. Accordingly, just prior to the grippers 163 gripping a filled, open container C from the filler wheel 47, the grippers 163 are sterilized by the transfer wheel e-beam emitter 166. Thus, the sterile condition of the container C continues to be maintained.

Figure 27:
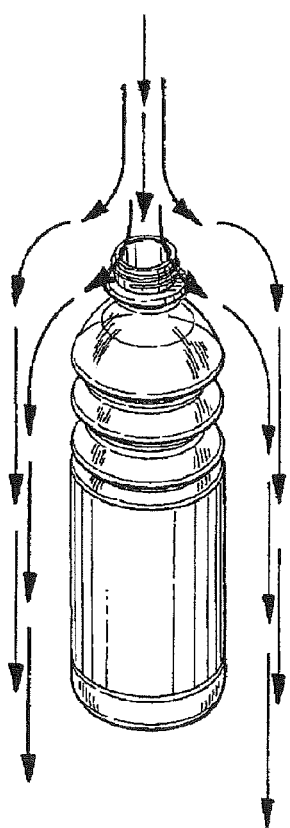
FIG. 27 is a schematic view of downward air flow around the container.

As previously discussed, the transfer mechanism air management system 164 provides ULPA/HEPA filtered air to the containers C at the transfer wheel 162. The third output 256 (FIG. 36) of the isolation sterile air supply system 242 provides sterile air to the inlet duct 168 and diverging outlet ends 172. The filtered air is directed downward through the screen 180 and into the outlet manifold 170. The screen 180 provides a certain amount of resistance to assure flow downwards over the open, filled containers C as they traverse on the transfer wheel 172. It is understood that the air management system 164 has a length generally corresponding to when the transfer wheel grippers 163 engage a container C to the time the grippers 163 pass the containers C to the capper assembly 48. The filtered airflow is directed at the container openings in a downward fashion to form an air curtain and assists in keeping microbes or other contaminants away from the openings of the containers C. FIGS. 26 and 27 show the filtered airflow about the openings of the containers wherein the airflow is directed downwards past the containers C. The filtered airflow is vented to the housing enclosure 222.

Figure 40:
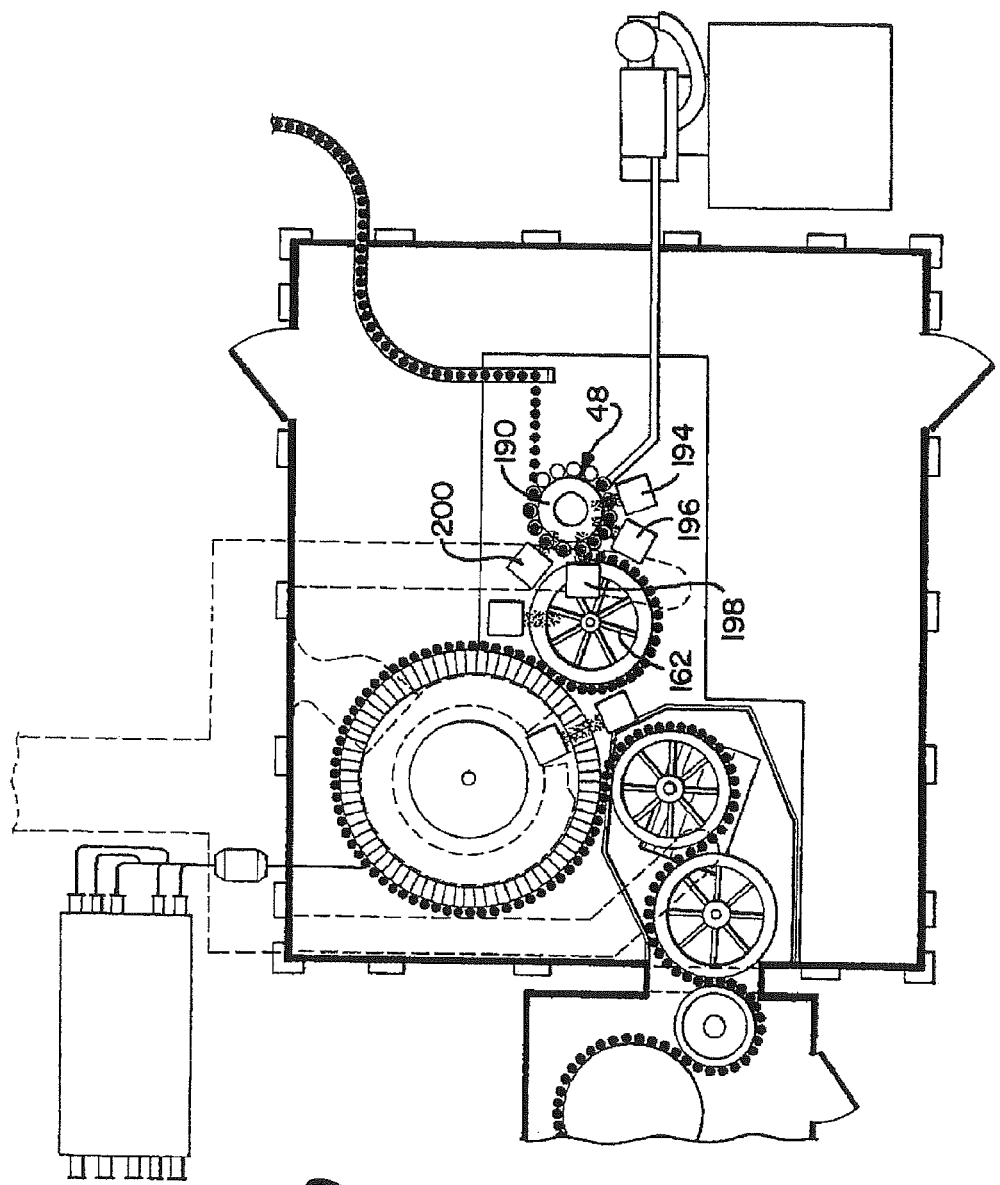

As shown in FIG. 40, the filled containers C are transferred from the transfer wheel 162 to the capper wheel 190 of the capper assembly 48. An additional separator plate may be provided with the transfer wheel 162 to make sure that any e-beam field associated with the capper assembly 48 is not directed into an open filled container C. Capper wheel grippers 191 engage the filled, open containers C. Prior to this engagement, the capper wheel 190 is prepared for capping the containers C with a cap 202. As discussed, the capper wheel 190 has a plurality of capper chucks 193 that will receive a cap 202 to be placed onto a container C. Prior to this operation, however, the caps, 202, capper chucks 193 and capper grippers 191 are sterilized to maintain the sterile conditions of the overall process.

As shown in FIGS. 28, 29, 35, and 40, a first capper wheel e-beam emitter 194 is positioned to focus its electron field to encompass the path traveled by the capper chucks 193. In this fashion, the capper chucks 193 are sterilized prior to receiving a cap 202 at a start position 201. As the capper chucks 193 continue to rotate on the capper wheel 190, the cap loader 192 functions to insert a cap 202 into the capper chuck 193. The cap loader 192 includes a rotating plate having slots to receive caps 202 may be fed to the plate via a cap chute. The cap loader 192 is positioned at an offset location to accommodate the capper wheel e-beam emitters. As further shown in FIG. 29, the cap 202 may extend a short distance beyond the cap chuck 193. Once a cap 202 is loaded onto the cap chuck 193, the second capper wheel e-beam emitter 196 is focused upwardly towards an underside of the cap 202, as shown in FIGS. 31-34. The electron field generated by the second capper wheel e-beam emitter 196 encompasses the path traveled by the capper chuck 193 carrying the cap 202. In this fashion, the underside surface of the cap 202 is sterilized by the second capper wheel e-beam emitter 196 at a cap loaded position 203. As the capper chuck 193 continues to be rotated by the capper wheel 190 along an arcuate path, the capper chuck 193 rotates itself approximately 180 degrees while in the electron beam field generated by the second capper wheel e-beam emitter 196. It is understood that the cap 202 has a depending skirt wherein a portion of the underside surface could be obstructed from penetration by the electron field because of the depending skirt of the cap 202. With the capper chuck rotation 193, this potentially obstructed surface is then rotated 180 degrees where it can confront the second cap e-beam emitter 196. While the cap 202 can be sufficiently sterilized without rotation of the capper chuck 193, the rotating capper chuck 193 within the field of the second capper wheel e-beam emitter 196 further enhances the sterility of the cap 202.

The capper wheel 190 continues to rotate the caps 202 held by a respective capper chuck 193 wherein the transfer wheel 162 passes the open, filled container C to the capper grippers 191 on the capper wheel 190. The capper chuck 193 then rotates the cap 202 onto the filled container C held by the capper grippers 193 moving in a downward direction as indicated by the arrow in FIG. 29. As further shown in FIGS. 29, 35 and 40, during this process, the third capper wheel e-beam emitter 198 and the further capper wheel e-beam emitter 200 generate electron beam sterile fields that encompass the path of the capper wheel 190 and, in particular, the path of the capper chuck 193 with cap 202 as the cap 202 is screwed onto the container C held by the capper gripper 193. As depicted by the arrow in FIG. 29, the capper moves downward to install the cap onto container C. The third and fourth e-beam emitters 198, 200 focus their respective fields on the airspace between the container C and cap 202 as the cap 202 is screwed onto the container C (e.g., below the capper chuck and proximate the capper grippers), thus maintaining the sterility of the capping process at a cap installation position 205. The angle of the third and fourth e-beam emitters 198, 200 allows the airspace and the capper chuck 193 to be sterilized simultaneously. Additionally, after the capper chuck 193 screws the cap 202 onto the container C, the third and the forth e-beam emitters 198, 200 sterilize the outside surface of the cap 202 as the capper chuck 193 is raised off of the cap 202 at a finished position 207.

Once capped, the containers C are further advanced by the capper wheel 190 and then directed to further portions of the conveyor 20 where the containers C are transported out of the second module 14 for further packaging operations 24 (FIGS. 4 and 35) and later shipment.

Thus, as can be appreciated from the above description, the containers C are filled, transferred, and capped in confined hygienic environments and active sterilization zones are provided in the second module 14 during operation. These systems prevent surface contamination and airborne contamination. The overall pathway of the container C is controlled in the filling and capping of the containers C. The components of the system 10 and, in particular, the components of the second module 14, provide a hostile environment for any potential contaminants or microbes. Because the system is treated chemically and with e-beams prior to operation, it initially starts out in a sterile condition. The various e-beam emitters, placed at strategic locations provide active sterilization zones ensuring that sterile conditions are maintained and that the containers C are not contaminated while being handled during the filling, transferring and capping operations. The isolation systems, providing controlled sterile air flow during the handling and filling operations, assist in maintaining the sterile conditions by providing CHE(s) that the containers C pass through while being filled and capped. It is understood that the ULPA/HEPA air is constantly supplied and changed out in the CHE during operation of the system 10. Each of the isolator air management system, the filler wheel air management system, and the local air management system of the transfer wheel can alone or in combination be considered a CHE. The CHE(s) in conjunction with the active sterilization zones all control the environment surrounding the pathway traveled by the container C during the filling, transferring, and capping operations. Accordingly, in one exemplary embodiment, the container C travels in a confined hygienic environment during its movement in the second module 14 from the isolator assembly 52 to the capper assembly 48. With the design of the present system 10, it is appreciated that only critical surfaces are subjected to e-beam sterilization while the product being filled in the containers C is not subjected to any e-beam sterilization or irradiation. With the design of the present system 10, it is understood that various types of beverages can be filled in containers C including low acid and high acid products. In addition, the product being filled in the containers C may be pre-treated as desired such that it has reduced or inhibited microbial growth characteristics.

Alternative Second Module—E-Beam Assembly

In an alternative embodiment, the second module, and the e-beam sterilization unit in particular, can be modified as discussed below. Generally, additional e-beam emitters are utilized and the isolator assembly 52 described above is not utilized. As depicted in FIGS. 43-49, the e-beam sterilization unit can generally include a first intake wheel e-beam emitter F1, a filler wheel e-beam emitter F2, a transfer wheel e-beam emitter F3, a first capper wheel e-beam emitter F4, a second capper wheel e-beam emitter F5, a first cap chute e-beam emitter C1, and a second cap chute e-beam emitter C2. The cap chute 552 can extend from the capper 550.

Again, the e-beam emitters are positioned such that only critical machine surfaces, components, and air immediately surrounding the components are subjected to the e-beams and not the beverage product itself. In one exemplary embodiment, the e-beam assembly is arranged according to the description below. The first transfer wheel e-beam emitter F1 has an e-beam zone located at approximately 9 o'clock on the first transfer wheel 554. The filler wheel e-beam emitter F2 has an e-beam zone located at approximately 5 o'clock on the filler wheel 547. The second transfer wheel e-beam emitter F3 has an e-beam zone located approximately at 12 o'clock on the second transfer wheel 556. The first capper wheel e-beam emitter F4 has an e-beam zone located approximately at 6 o'clock on the capper wheel 557. The second capper wheel e-beam emitter F5 has an e-beam zone located approximately at 2 o'clock on the capper wheel 557, which is proximate to the torque head and air space between the cap and container finish. Again, it is understood that variations of the locations and numbers of the e-beam zones are possible.

Alternative First Transfer Wheel Sterilization

Figure 43:
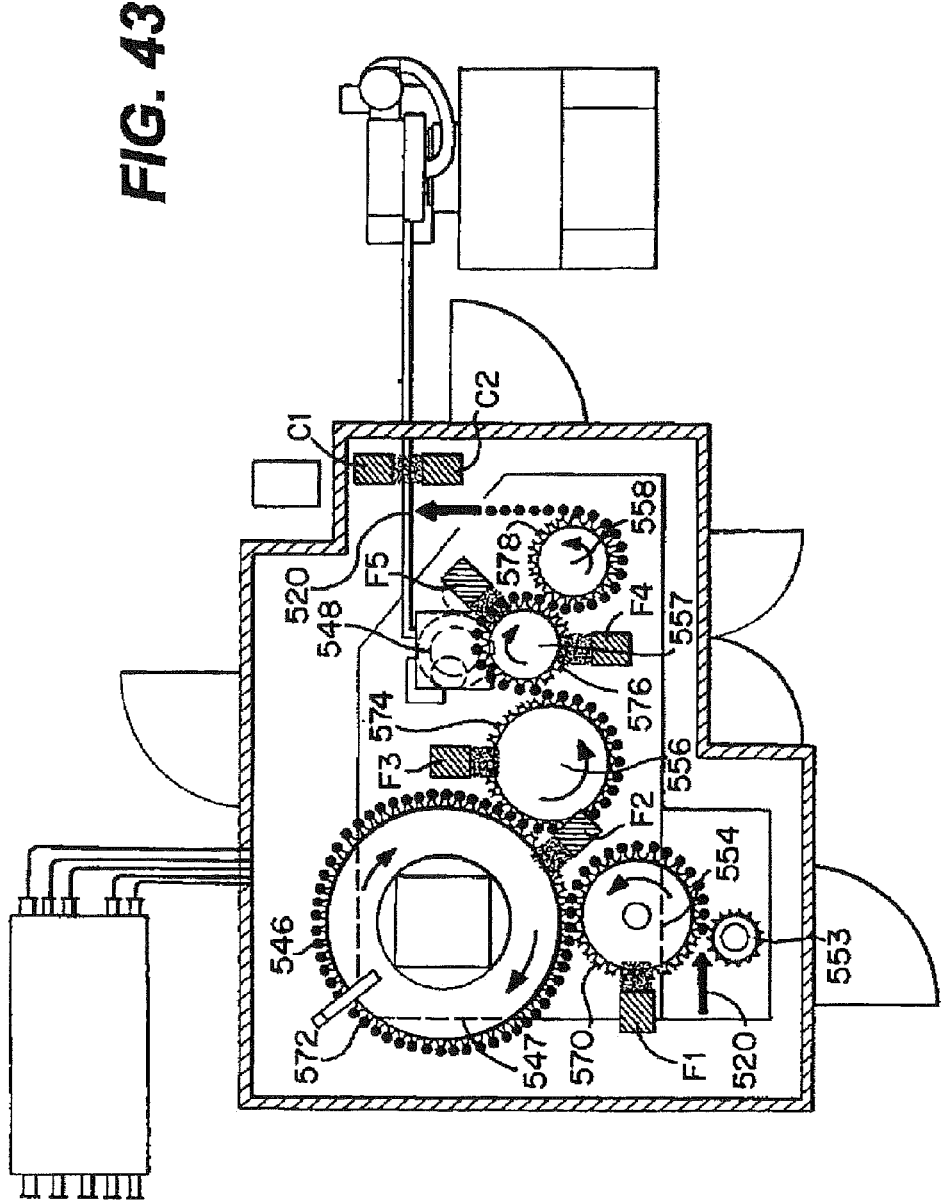
FIGS. 43-49 are schematic plan views of an alternative embodiment of the second module of the system of the present invention.

In this alternative embodiment, as shown in FIG. 43, the isolator is removed from the second module, and the first transfer wheel can be provided with an e-beam emitter F1 to maintain the sterility of the containers. After the sterile containers travel through the airlock structure (as discussed above), the containers are brought into the second module by the intake wheel 553 and transferred to the first transfer wheel 554. Since the first transfer wheel 554 grips the container by its neck, grippers 570 on the first transfer wheel 554 are sterilized prior to receiving the containers C to prevent any microbes that are present on the grippers 570 from contaminating the neck or the mouth of the container, as depicted in FIG. 43. Thus, the grippers 570 located on the first transfer wheel 554 are exposed to the e-beam zone produced by the first transfer wheel e-beam emitter F1. As shown in FIG. 43, the first transfer wheel e-beam emitter F1 provides an electron field that generally encompasses the grippers 570 rotating on the first transfer wheel 554. It is understood that the grippers 570 generally pass into and through the electron field. In one embodiment, the first transfer wheel 554 moves at a rate of approximately 21 rpm (600 bpm) and each neck handling gripper 570 is dosed once every 2.8 seconds to ensure that every container is gripped by a sterilized gripper. After the grippers 570 are exposed to the e-beam zone produced by the first transfer wheel e-beam emitter F1, the grippers 570 receive the containers from the intake wheel 553 of the conveyor 520 that may be considered associated with the first module. The first transfer wheel 554 then delivers the containers to the filler 546.

Alternative Filler Wheel Sterilization

Figure 44:
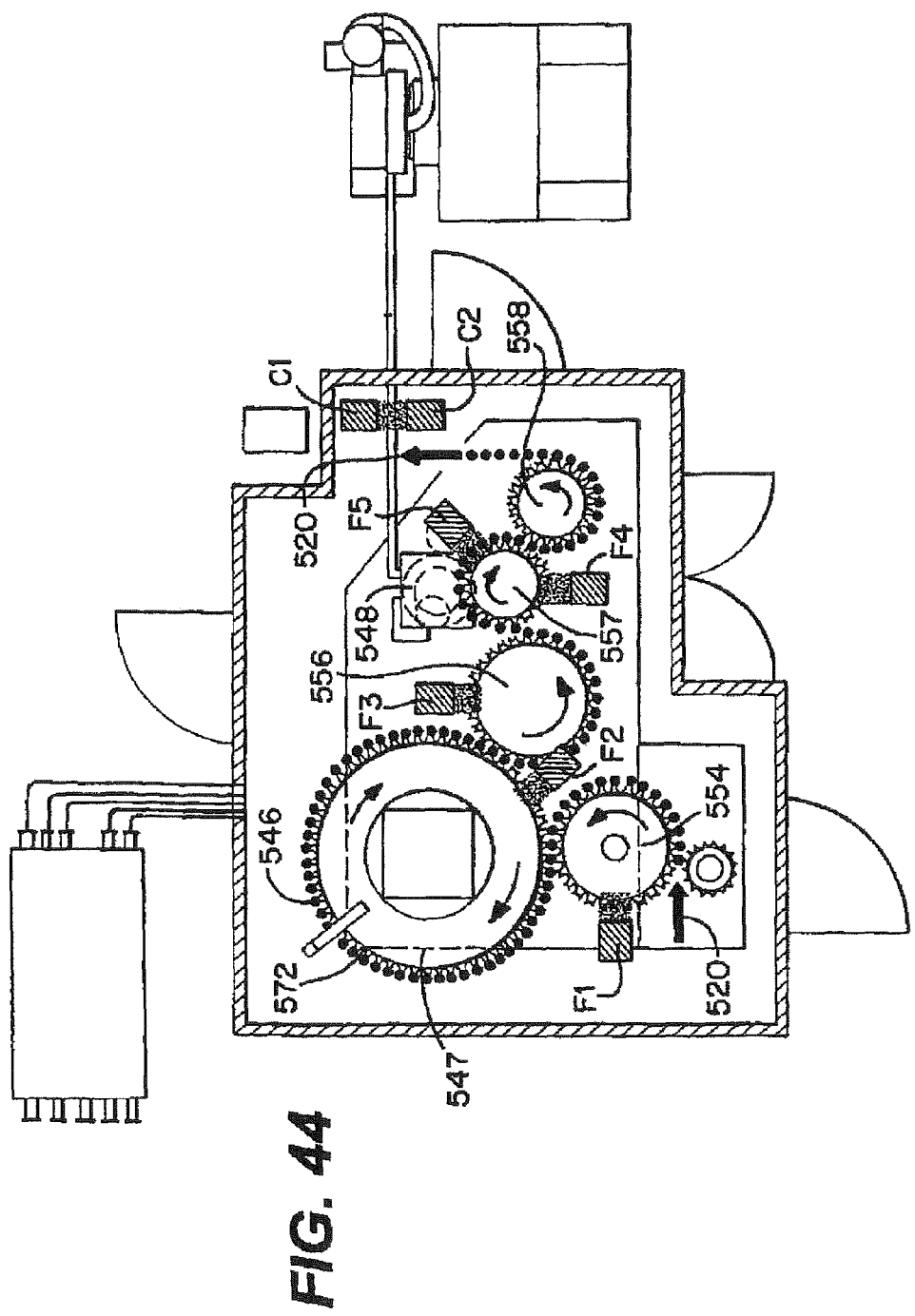
Figure 45:
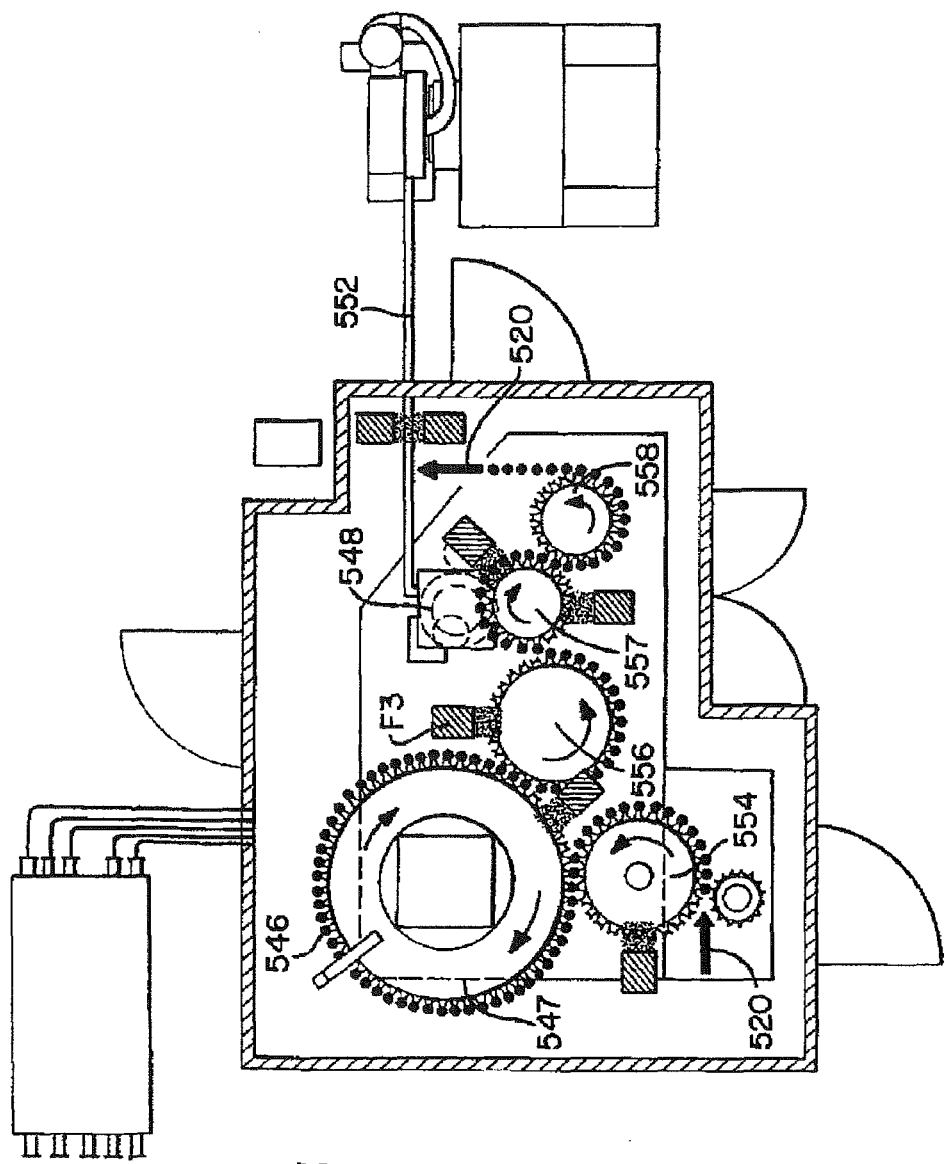
Figure 46:
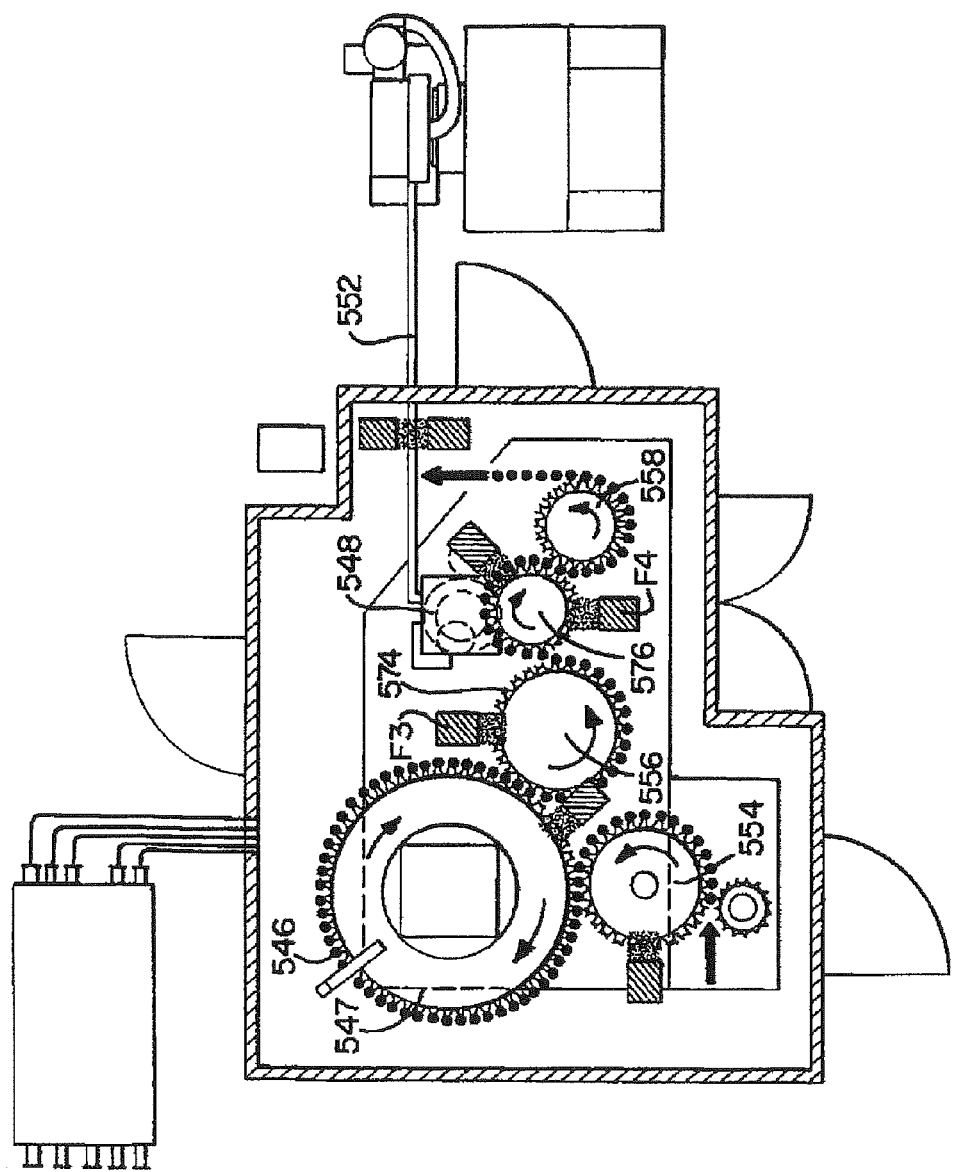
Figure 47:
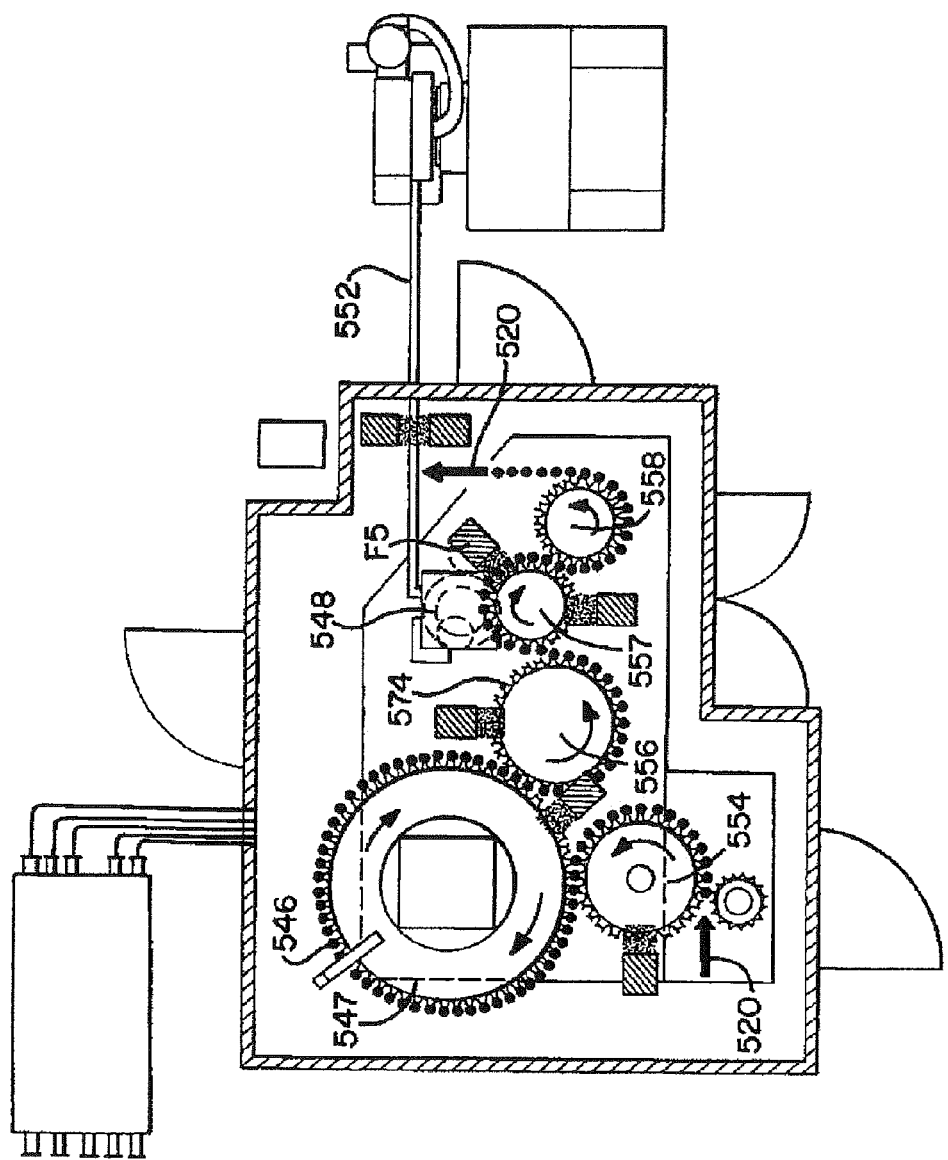
Figure 48:
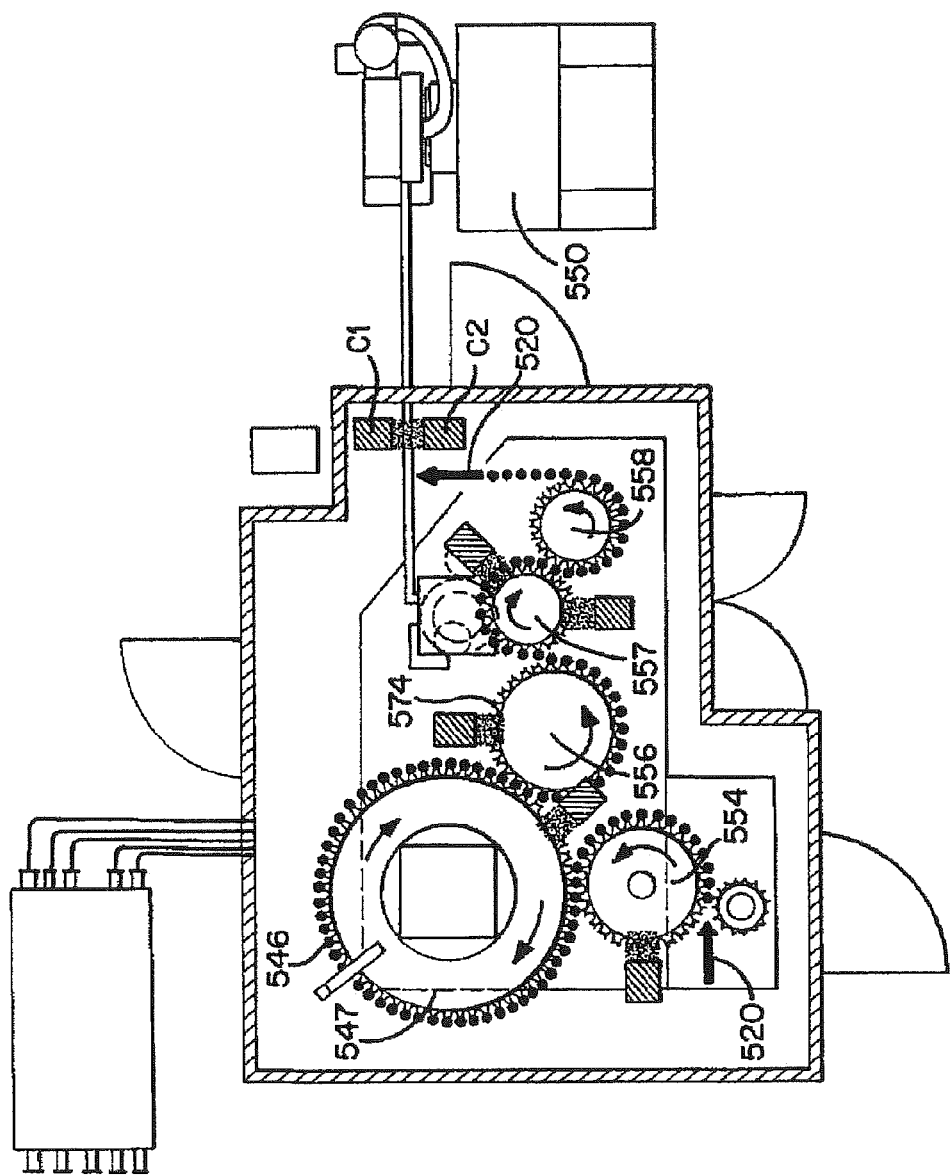
Figure 49:
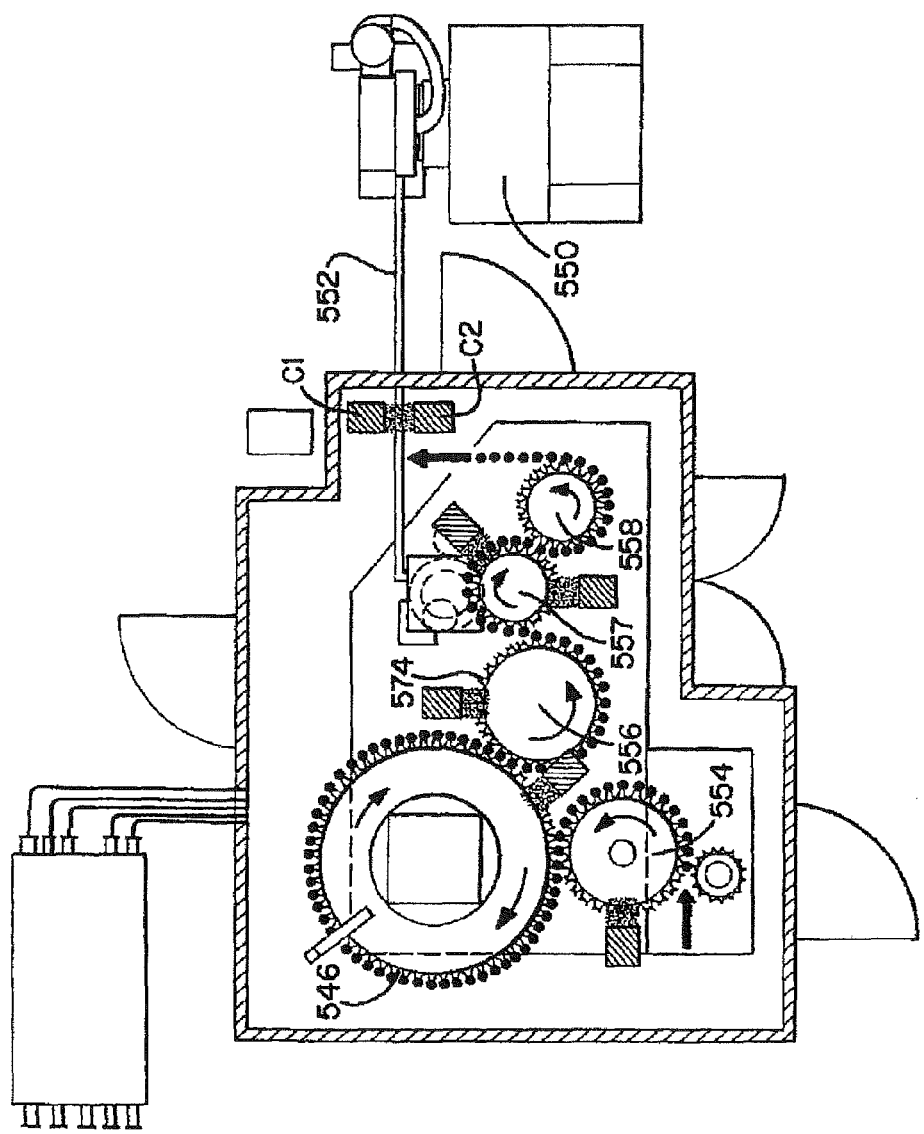

As depicted in FIGS. 44 and 45, before the containers are placed on the filler wheel 547, the filler wheel e-beam emitter F2 sterilizes the filler wheel grippers 572 prior to receiving the containers. In addition, the filler wheel e-beam emitter F2 is positioned such that it also sterilizes the filler valves just before the filler valve heads contact the containers. Because of the degree of impingement at which the filler wheel e-beam emitter F2 is positioned, the filler valves pass through the electron beam field simultaneously with the grippers 572. Any microorganisms, therefore, that might be present on the filler valve heads are killed, and the grippers 572 and the filler valve heads remain sterile. The electron beam zone produced by the filler wheel e-beam emitter F2 fully encompasses the filler valve heads to sterilize all sides prior to filling. By sterilizing the filler valve heads just before each filling event, it is guaranteed that any microorganisms present on the filler valve head are not transferred to the product. By way of example, in a filler with sixty (60) filler valve heads with approximately a seventy-six (76) inch diameter filler wheel, each valve and gripper can be dosed once every 6 seconds by the filler wheel e-beam emitter F2 in order to accomplish sufficient sterilization. Once the containers are filled, the containers are passed off to the second transfer wheel 556.

Alternative Transfer Wheel Sterilization

After the containers have been filled with beverage product they are transferred to the capper via the second transfer wheel 556 to be sealed with a closure. It is necessary to sterilize the grippers 574 holding a filled, open container, and the travel zone just above the containers, so that contamination is not introduced onto the container mouth or into the product. Thus, as shown in FIG. 39, before receiving the container from the filler wheel 547, the e-beam zone produced by the second transfer wheel e-beam emitter F3 sterilizes the grippers 574 located on the second transfer wheel 556. In one embodiment, the second transfer wheel 556 has a diameter of approximately forty (40) inches. At 600 bpm, therefore, each gripper 574 is dosed by the second transfer wheel e-beam emitter F3 approximately once every 2.8 seconds. After sterilization, the grippers 574 on the second transfer wheel 556 receive the containers from the filler 546, and transfer the containers to the capper wheel 557, such that the capper 548 can cap each filled container.

Alternative Air System

Figure 51:
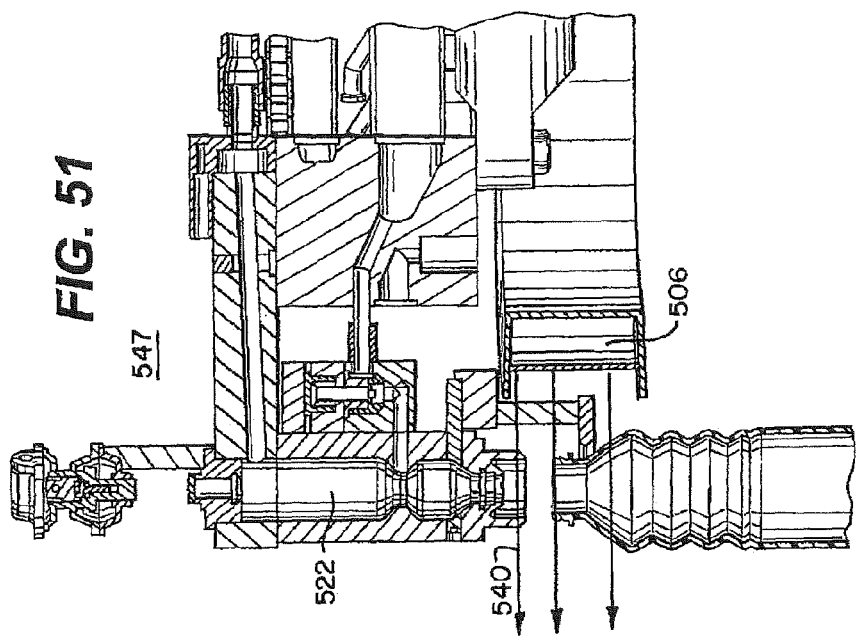
FIGS. 50-53 disclose additional views of the alternative embodiment of the second module of the system of the present invention.
Figure 50:
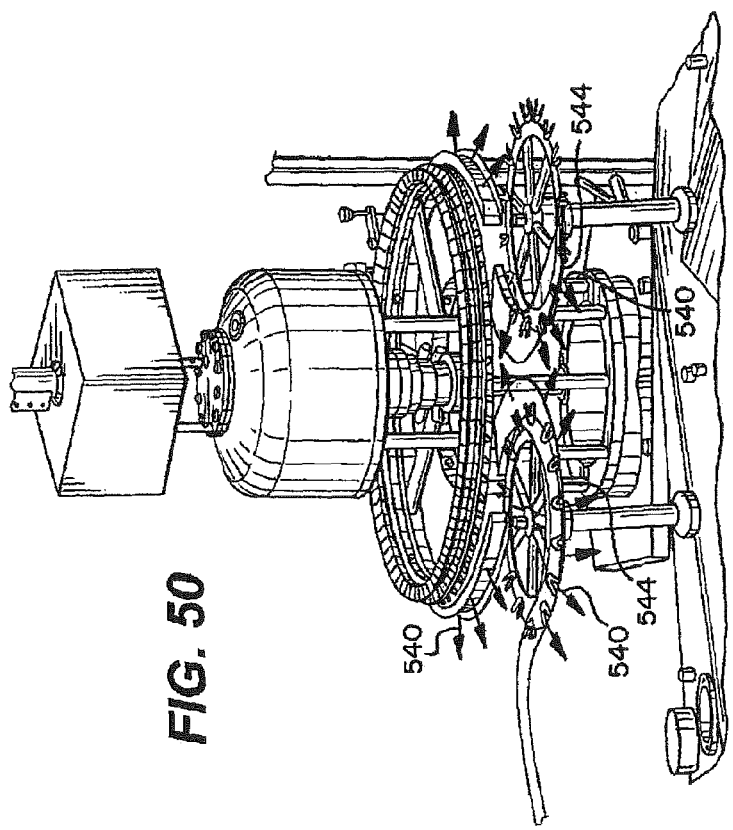
Figure 52:
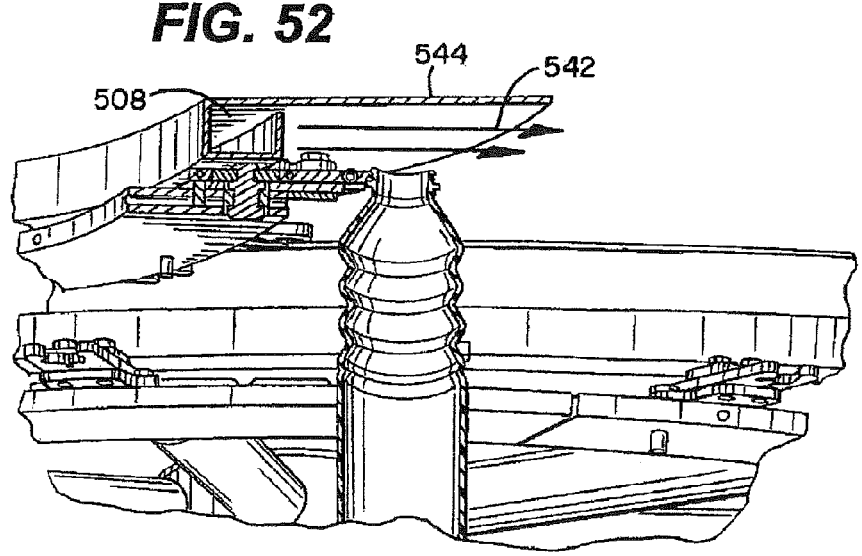

In an alternative embodiment, the first and second transfer wheels and the filler wheel can each be provided with a separate air system. As depicted in FIG. 51, the filler wheel 547 has a channel 506 that supplies ULPA filtered air from behind the filler valves. This creates an even distribution of air 540, moving away from the container finish and preventing contaminants from landing on the container finish, filler valves, or neck grippers. Air 540 is evenly distributed through supply ducts stemming from the center of the filler wheel in a spoke-like pattern, as depicted in FIG. 50. As shown in FIG. 52, the second channel 508 serves the same purpose on the transfer wheels 554, 556, 558. The second channel 508 and channel cover 544 create a steady stream of air over the top of the container, pushing air out from the center of the transfer wheels 554, 556, 558. The second channel 508 is formed such that an air curtain is created on the underside of the channel cover 544. Velocities and volumes of air are such that the currents are greater than the turbulent motion of the rotating filler and transfer wheels. Airflow is created in a radial, outward direction away from the product and the critical container path. A similar method can be used on the capper wheel 557.

FIG. 51 depicts an alternative exemplary method which can be implemented to provide air to the filler wheel. As depicted in FIG. 51, the filler wheel 547 has a first channel 506 that supplies ULPA/HEPA filtered air from behind the filler valves 522. The filler wheel 547 has a channel 506 that supplies ULPA/HEPA filtered air from behind the filler valves. This creates an even distribution of air 540, moving away from the container finish and prevents contaminants from landing on the container finish, filler valves, or neck grippers. Air 540 is evenly distributed through supply ducts stemming from the center of the filler wheel in a spoke-like pattern, as depicted in FIG. 50.

In another exemplary embodiment, as depicted in FIG. 52, the third transfer wheel 556 can include a second channel 508, which supplies ULPA/HEPA filtered air. The second channel 508 serves the same purpose on the transfer wheel 556. The second channel 508 and channel cover 544 create a steady stream of air over the top of the container, pushing air out from the center of the transfer wheel 556. The second channel 508 is formed such that an air curtain is created on the underside of the channel cover 544. Velocities and volumes of air are such that the currents are greater than the turbulent motion of the rotating filler and transfer wheels. Airflow is created in a radial, outward direction away from the product and the critical container path. A similar method is to also be used on the capper wheel 557 if desired.

Figure 53:
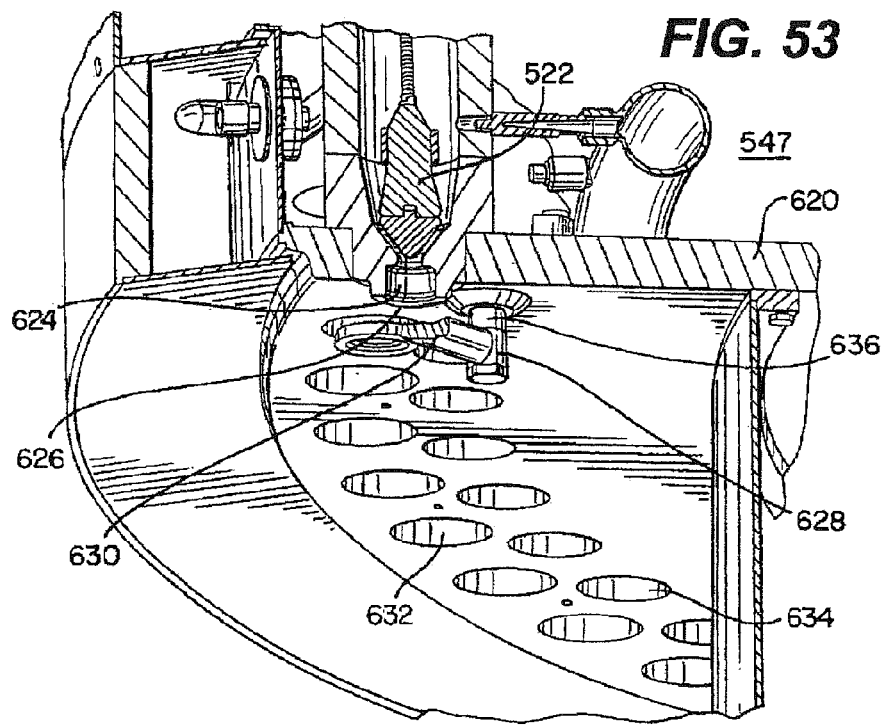

To further reduce contamination, the filling area of the filler wheel 547 can be cleaned in a clean-in-place ("CIP") procedure. As depicted in FIG. 53, the filler wheel 547 also houses a plate 620, which segregates the filler valves 522 and other moving parts from the container filling area 624. The filler valves 522 each have an associated filler port 632. Each filler valve 522 has an associated CIP capping mechanism 628. The CIP capping mechanisms 628 are fixed in each one of ports 634. Each CIP capping mechanism 628 has a CIP cap 626 and a capping arm 630, which is rotatably fixed on a capping post 636. As shown in FIG. 53, the plate 620 is used in the aseptic design to segregate the filler valves 522 and moving parts from the container filling area 624. This division maintains a clean environment for the filling operation, and reduces the parts susceptible to contamination. Enclosing the filler valves 522 also reduces the turbulence caused by rotation of the filler wheel 547, and contributes to greater airflow. The enclosed parts can be accessed for maintenance through a removable cover (not shown). This cold-fill technique is part of the unique active sterilization zone developed under this method.

Active Sterilization Zone Environment

The system of the exemplary embodiment is designed to eliminate microbes that are physically transferred from component to component throughout the filling process and that culture or cultivate on the components of the system. The system utilizes e-beam technology to sterilize the containers, caps, and critical contact surfaces.

The emitters create an "active" sterilization zone such that the containers C remain in a sterilized environment until they exit to final packaging. The e-beams in combination with the air system aid in killing the microbes on the critical contact surfaces of the system. In addition the e-beam generators produce secondary e-beams and X-rays. The e-beams also react with oxygen (O2) and nitrogen to yield nitric acid and ozone ($O_3$). Each of the above (e-beams, air, x-rays, nitric acid, ozone ($O_3$), and secondary e-beams) aid in eliminating microbes in the system by starving the microbes of necessities such as air, water, and other nutrients.

Traditional cold-fill lines, with their passive sterilization techniques, require that all components brought into the environment be pre-sterilized. They rely on this pre-sterilization to prevent any contamination of the aseptic environment. Once the environment has been contaminated, however, making the environment truly aseptic again is very difficult. By having an active sterilization zone, any contaminants that may enter the zone can be immediately sterilized upon contact with critical surfaces, minimizing system downtime and cost.

As can be appreciated with the exemplary embodiments disclosed herein, it is no longer necessary to heat the beverage product and to invert the hot container to sterilize the headspace. Since the containers are not hot, a container cooler is no longer necessary. The removal of these two pieces of equipment further simplifies and streamlines the container filling process. With the system of the exemplary embodiments, containers that were previously filled in a hot-fill process can now be filled at ambient temperatures wherein the product injected into the containers is at ambient temperatures. As such, containers are not required to have as robust a sidewall construction as before. Accordingly, the containers can be made with less material, resulting in significant material cost savings. This also provides more flexibility in container design. In addition, less energy is required as the beverage product no longer needs to be held at the high temperature for as long. Also, the system allows for the sterile filling of containers with the beverage, while not requiring additional preservatives to meet acceptable shelf-life requirements. In addition to the container material savings, other sustainability benefits include water savings, natural gas savings and a reduction of greenhouse gases. The system design further provides that the local filling point of the containers is re-sterilized at each and every filling event. Finally, the e-beam technology provides acceptable dosing in a fraction of a second, thereby providing for an enhanced in-line sterilization and filling process.

Several alternative embodiments and examples have been described and illustrated herein. A person of ordinary skill in the art would appreciate the features of the individual embodiments, and the possible combinations and variations of the components. A person of ordinary skill in the art would further appreciate that any of the embodiments could be provided in any combination with the other embodiments disclosed herein. It is understood that the invention may be embodied in other specific forms without departing from the spirit or central characteristics thereof. The present examples and embodiments, therefore, are to be considered in all respects as illustrative and not restrictive, and the invention is not to be limited to the details given herein. Accordingly, while the specific embodiments have been illustrated and described, numerous modifications come to mind without significantly departing from the spirit of the invention and the scope of protection is only limited by the scope of the accompanying claims.

What is claimed is:

1. An apparatus for receiving a sterile container, delivering the sterile container to a filler assembly, and the sterile filling of the container, the apparatus comprising:
an isolator unit; and
a filler unit;

wherein the isolator unit comprises:

a housing comprising a first side wall having a container inlet opening and second side wall having a container outlet opening, the housing further having an air inlet opening;

a shroud positioned on the exterior of the first side wall around the container inlet opening, the shroud having a horizontal wall, and a first depending wall, a second depending wall, and an open bottom end, wherein the shroud defines an exterior interface area for receiving a sterile container, and wherein a width of the shroud exceeds a height of the shroud, and wherein the height of the shroud exceeds a length of the shroud;

an intake conveyor positioned in the housing, the conveyor adapted to receive the sterile container through the container inlet opening from the interface area and pass the sterile container to the container outlet opening, wherein the intake conveyor comprises an intake wheel having a conveyor gripper, wherein the conveyor gripper is adapted to grip a container delivered from a container sterilizer and pass the container to the container outlet opening; and an air source in communication with the air inlet opening wherein the housing receives air into the inlet opening and wherein the received air passes from the housing to the exterior interface area and out of the open bottom end of the shroud; and wherein the filler unit comprises:

a filler wheel having at least one filler gripper adapted to receive the sterile container in the container outlet opening, and a first filler wheel e-beam unit, wherein the first filler wheel e-beam unit is directed at the at least one filler gripper such that the filler gripper receives e-beam treatment prior to receiving the sterile container, the filler wheel configured to fill the sterile container with a product;

a local air management system operably associated with the filler wheel, wherein the filler wheel localized air management system comprises an inlet manifold, an intermediate supply section, and a generally annular channel that defines a pathway for the sterile container.

2. The apparatus of claim 1 wherein the air inlet opening is positioned on a ceiling of the housing.

3. The apparatus of claim 1 wherein the air source is filtered.

4. The apparatus of claim 3 wherein the air source is ULPA/HEPA filtered air.

5. The apparatus of claim 1 wherein the intake conveyor comprises a first intake wheel operably associated with a second intake wheel, the first intake wheel adapted to receive the container from a container sterilizer and further adapted to pass the container to the second intake wheel wherein the second intake wheel is adapted to pass the container to the container outlet opening.

6. The apparatus of claim 1 wherein the housing has an access door.

7. The apparatus of claim 6 wherein the intake conveyor has a container reject mechanism wherein unacceptable containers are removed from the conveyor and can be accessed through the access door.

8. The apparatus of claim 6 further comprising an air cylinder having one end connected to the housing and another end connected to the access door, the air cylinder being operable to open and close the access door.

9. The apparatus of claim 7 wherein the housing has a floor wherein a portion of the floor is slanted towards the access door.

10. The apparatus of claim 1 wherein the housing comprises at least one window and wherein the at least one window permits access to the intake conveyor.

11. The apparatus of claim 10 wherein the at least one window includes a hinge for opening the at least one window to permit access to the intake conveyor.

12. The apparatus of claim 10 wherein the at least one window further comprises a seal placed around a perimeter of the at least one window.

13. The apparatus of claim 10 wherein the at least one window further comprises a lock.

* * * * *